United States Patent
Demarais et al.

(10) Patent No.: US 8,145,317 B2
(45) Date of Patent: *Mar. 27, 2012

(54) METHODS FOR RENAL NEUROMODULATION

(75) Inventors: Denise Demarais, Los Gatos, CA (US); Hanson Gifford, III, Woodside, CA (US); Mark Deem, Mountain View, CA (US); Douglas Sutton, Pacifica, CA (US); Howard R. Levin, Teaneck, NJ (US); Mark Gelfand, New York, NY (US)

(73) Assignee: Ardian, Inc., Mountain View, CA (US)

( * ) Notice: Subject to any disclaimer, the term of this patent is extended or adjusted under 35 U.S.C. 154(b) by 1017 days.

This patent is subject to a terminal disclaimer.

(21) Appl. No.: 11/368,577

(22) Filed: Mar. 6, 2006

(65) Prior Publication Data

US 2006/0276852 A1    Dec. 7, 2006

Related U.S. Application Data

(63) Continuation-in-part of application No. 10/408,665, filed on Apr. 8, 2003, now Pat. No. 7,162,303, which is a continuation-in-part of application No. 11/133,925, filed on May 20, 2005, which is a continuation of application No. 10/900,199, filed on Jul. 28, 2004, now Pat. No. 6,978,174, which is a continuation-in-part of application No. 10/408,665, filed on Apr. 8, 2003, now Pat. No. 7,162,303, application No. 11/368,577, which is a continuation-in-part of application No. 11/189,563, filed on Jul. 25, 2005, which is a continuation-in-part of application No. 11/129,765, filed on May 13, 2005, now Pat. No. 7,653,438, application No. 11/368,577, which is a continuation-in-part of application No. 11/266,993, filed on Nov. 4, 2005, now Pat. No. 7,756,583, and a continuation-in-part of application No. 11/363,867, filed on Feb. 27, 2006, now Pat. No. 7,620,451, and a continuation-in-part of application No. 11/189,563, filed on Jul. 25, 2005, and a continuation-in-part of application No. 11/266,993, filed on Nov. 4, 2005, now Pat. No. 7,756,583.

(60) Provisional application No. 60/442,970, filed on Jan. 29, 2003, provisional application No. 60/415,575, filed on Oct. 3, 2002, provisional application No. 60/370,190, filed on Apr. 8, 2002, provisional application No. 60/616,254, filed on Oct. 5, 2004, provisional application No. 60/624,793, filed on Nov. 2, 2004, provisional application No. 60/813,589, filed on Dec. 29, 2005.

(51) Int. Cl.
*A61N 1/00* (2006.01)
*A61F 7/00* (2006.01)
*A61K 9/22* (2006.01)

(52) U.S. Cl. .................. 607/44; 607/99; 604/891.1

(58) Field of Classification Search .................. 607/40, 607/44, 96, 98, 133, 99, 118
See application file for complete search history.

(56) References Cited

U.S. PATENT DOCUMENTS

| | | |
|---|---|---|
| 2,130,758 A | 9/1938 | Rose |
| 2,276,995 A | 3/1942 | Milinowski |
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler |
| 3,897,789 A | 8/1975 | Blanchard |
| 3,911,930 A | 10/1975 | Hagfors et al. |

| Patent No. | Date | Inventor |
|---|---|---|
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,602,624 A | 7/1986 | Naples et al. |
| 4,608,985 A | 9/1986 | Crish et al. |
| 4,649,936 A | 3/1987 | Ungar et al. |
| 4,671,286 A | 6/1987 | Renault |
| 4,674,482 A | 6/1987 | Waltonen et al. |
| 4,692,147 A | 9/1987 | Duggan |
| 4,715,852 A | 12/1987 | Reinicke et al. |
| 4,774,967 A | 10/1988 | Zanakis |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,976,711 A | 12/1990 | Parins et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,019,034 A | 5/1991 | Weaver et al. |
| 5,057,318 A | 10/1991 | Magruder et al. |
| 5,058,584 A | 10/1991 | Bourgeois |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,304,120 A | 4/1994 | Crandell et al. |
| 5,304,206 A | 4/1994 | Baker |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,351,394 A | 10/1994 | Weinberg |
| 5,358,514 A | 10/1994 | Schulman et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,423,744 A | 6/1995 | Gencheff et al. |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,470,352 A | 11/1995 | Rappaport |
| 5,472,406 A | 12/1995 | de la Torre et al. |
| 5,478,303 A | 12/1995 | Foley-Nolan et al. |
| 5,484,400 A | 1/1996 | Edwards et al. |
| 5,494,822 A | 2/1996 | Sadri |
| 5,498,238 A | 3/1996 | Shapland et al. |
| 5,499,971 A | 3/1996 | Shapland et al. |
| 5,505,700 A | 4/1996 | Leone et al. |
| 5,507,724 A | 4/1996 | Hofmann et al. |
| 5,507,791 A | 4/1996 | Sit'ko |
| 5,531,778 A | 7/1996 | Maschino et al. |
| 5,540,730 A | 7/1996 | Terry, Jr. et al. |
| 5,540,734 A | 7/1996 | Zabara |
| 5,553,611 A | 9/1996 | Budd et al. |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens |
| 5,584,863 A | 12/1996 | Rauch et al. |
| 5,589,192 A | 12/1996 | Okabe et al. |
| 5,599,345 A | 2/1997 | Edwards et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,672,174 A | 9/1997 | Gough et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,722,401 A | 3/1998 | Pietroski et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,772,590 A | 6/1998 | Webster, Jr. |
| 5,792,187 A | 8/1998 | Adams |
| 5,800,464 A | 9/1998 | Kieval |
| 5,807,306 A | 9/1998 | Shapland et al. |
| 5,810,802 A | 9/1998 | Panescu et al. |
| 5,814,079 A | 9/1998 | Kieval |
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |
| 5,861,021 A | 1/1999 | Thome et al. |
| 5,865,787 A | 2/1999 | Shapland et al. |
| 5,871,449 A | 2/1999 | Brown |
| 5,891,181 A | 4/1999 | Zhu |
| 5,906,636 A | 5/1999 | Casscells, III et al. |
| 5,906,817 A | 5/1999 | Moullier et al. |
| 5,913,876 A | 6/1999 | Taylor et al. |
| 5,916,154 A | 6/1999 | Hobbs et al. |
| 5,916,239 A | 6/1999 | Geddes et al. |
| 5,919,187 A | 7/1999 | Guglielmi et al. |
| 5,924,997 A | 7/1999 | Campbell |

| | | | |
|---|---|---|---|
| 5,928,272 A | 7/1999 | Adkins et al. | |
| 5,935,075 A | 8/1999 | Casscells et al. | |
| 5,944,710 A | 8/1999 | Dev et al. | |
| 5,954,719 A | 9/1999 | Chen et al. | |
| 5,983,131 A | 11/1999 | Weaver et al. | |
| 5,983,141 A | 11/1999 | Sluijter et al. | |
| 6,006,134 A | 12/1999 | Hill et al. | |
| 6,009,877 A | 1/2000 | Edwards | |
| 6,010,613 A | 1/2000 | Walters et al. | |
| 6,026,326 A | 2/2000 | Bardy | |
| 6,041,252 A | 3/2000 | Walker et al. | |
| 6,051,017 A | 4/2000 | Loeb et al. | |
| 6,058,328 A | 5/2000 | Levine et al. | |
| 6,058,331 A | 5/2000 | King | |
| 6,066,134 A | 5/2000 | Eggers et al. | |
| 6,073,048 A | 6/2000 | Kieval et al. | |
| 6,077,227 A | 6/2000 | Miesel et al. | |
| 6,086,527 A | 7/2000 | Talpade | |
| 6,117,101 A | 9/2000 | Diederich et al. | |
| 6,122,548 A | 9/2000 | Starkebaum et al. | |
| 6,123,718 A | 9/2000 | Tu et al. | |
| 6,135,999 A | 10/2000 | Fanton et al. | |
| 6,146,380 A | 11/2000 | Racz et al. | |
| 6,161,048 A | 12/2000 | Sluijter et al. | |
| 6,171,306 B1 | 1/2001 | Swanson et al. | |
| 6,178,349 B1 | 1/2001 | Kieval | |
| 6,190,353 B1 | 2/2001 | Makower et al. | |
| 6,192,889 B1 | 2/2001 | Morrish | |
| 6,205,361 B1 | 3/2001 | Kuzma et al. | |
| 6,208,894 B1 | 3/2001 | Schulman et al. | |
| 6,214,032 B1 | 4/2001 | Loeb et al. | |
| 6,219,577 B1 | 4/2001 | Brown, III et al. | |
| 6,224,592 B1 | 5/2001 | Eggers et al. | |
| 6,238,702 B1 | 5/2001 | Berde et al. | |
| 6,245,026 B1 | 6/2001 | Campbell et al. | |
| 6,246,912 B1 | 6/2001 | Sluijter | |
| 6,251,130 B1 | 6/2001 | Dobak, III et al. | |
| 6,254,598 B1 | 7/2001 | Edwards et al. | |
| 6,258,087 B1 | 7/2001 | Edwards et al. | |
| 6,259,952 B1 | 7/2001 | Sluijter et al. | |
| 6,269,269 B1 | 7/2001 | Ottenhoff et al. | |
| 6,272,377 B1 | 8/2001 | Sweeney et al. | |
| 6,272,383 B1 | 8/2001 | Grey et al. | |
| 6,273,886 B1 | 8/2001 | Edwards et al. | |
| 6,280,377 B1 | 8/2001 | Talpade | |
| 6,287,304 B1 | 9/2001 | Eggers et al. | |
| 6,287,608 B1 | 9/2001 | Levin et al. | |
| 6,292,695 B1 | 9/2001 | Webster, Jr. et al. | |
| 6,304,777 B1 | 10/2001 | Ben-Haim et al. | |
| 6,304,787 B1 | 10/2001 | Kuzma et al. | |
| 6,306,423 B1 | 10/2001 | Donovan et al. | |
| 6,322,558 B1 | 11/2001 | Taylor et al. | |
| 6,322,559 B1 | 11/2001 | Daulton et al. | |
| 6,326,020 B1 | 12/2001 | Kohane et al. | |
| 6,326,177 B1 | 12/2001 | Schoenbach et al. | |
| 6,328,699 B1 | 12/2001 | Eigler et al. | |
| 6,334,069 B1 | 12/2001 | George et al. | |
| 6,347,247 B1 | 2/2002 | Dev et al. | |
| 6,353,763 B1 | 3/2002 | George et al. | |
| 6,356,786 B1 | 3/2002 | Rezai et al. | |
| 6,356,787 B1 | 3/2002 | Rezai et al. | |
| 6,366,808 B1 | 4/2002 | Schroeppel et al. | |
| 6,366,815 B1 | 4/2002 | Haugland et al. | |
| 6,393,324 B2 | 5/2002 | Gruzdowich et al. | |
| 6,400,982 B2 | 6/2002 | Sweeney et al. | |
| 6,405,079 B1 | 6/2002 | Ansarinia | |
| 6,405,732 B1 | 6/2002 | Edwards et al. | |
| 6,413,255 B1 | 7/2002 | Stern | |
| 6,415,183 B1 | 7/2002 | Scheiner et al. | |
| 6,415,187 B1 | 7/2002 | Kuzma et al. | |
| 6,438,423 B1 | 8/2002 | Rezai et al. | |
| 6,442,424 B1 | 8/2002 | Ben-Haim et al. | |
| 6,449,507 B1 | 9/2002 | Hill et al. | |
| 6,450,942 B1 | 9/2002 | Lapanashvili et al. | |
| 6,461,314 B1 | 10/2002 | Pant et al. | |
| 6,464,687 B1 | 10/2002 | Ishikawa et al. | |
| 6,473,644 B1 | 10/2002 | Terry, Jr. et al. | |
| 6,482,619 B1 | 11/2002 | Rubinsky et al. | |
| 6,506,189 B1 | 1/2003 | Rittman, III et al. | |
| 6,508,774 B1 | 1/2003 | Acker et al. | |
| 6,514,226 B1 | 2/2003 | Levin et al. | |
| 6,516,211 B1 | 2/2003 | Acker et al. | |
| 6,517,811 B2 | 2/2003 | John et al. | |
| 6,522,926 B1 | 2/2003 | Kieval et al. | |
| 6,522,932 B1 | 2/2003 | Kuzma et al. | |
| 6,524,607 B1 | 2/2003 | Goldenheim et al. | |
| 6,534,081 B2 | 3/2003 | Goldenheim et al. | |
| 6,536,949 B1 | 3/2003 | Heuser | |
| 6,564,096 B2 | 5/2003 | Mest | |
| 6,571,127 B1 | 5/2003 | Ben-Haim et al. | |
| 6,592,567 B1 | 7/2003 | Levin et al. | |
| 6,599,256 B1 | 7/2003 | Acker et al. | |
| 6,600,954 B2 | 7/2003 | Cohen et al. | |
| 6,600,956 B2 | 7/2003 | Maschino et al. | |
| 6,601,459 B1 | 8/2003 | Jenni et al. | |
| 6,605,084 B2 | 8/2003 | Acker et al. | |
| 6,613,045 B1 | 9/2003 | Laufer et al. | |
| 6,615,071 B1 | 9/2003 | Casscells, III et al. | |
| 6,616,624 B1 | 9/2003 | Kieval | |
| 6,620,151 B2 | 9/2003 | Blischak et al. | |
| 6,622,041 B2 | 9/2003 | Terry, Jr. et al. | |
| 6,622,731 B2 | 9/2003 | Daniel et al. | |
| 6,635,054 B2 | 10/2003 | Fjield et al. | |
| 6,654,636 B1 | 11/2003 | Dev et al. | |
| 6,666,845 B2 | 12/2003 | Hooper et al. | |
| 6,669,655 B1 | 12/2003 | Acker et al. | |
| 6,671,556 B2 | 12/2003 | Osorio et al. | |
| 6,672,312 B2 | 1/2004 | Acker | |
| 6,676,657 B2 | 1/2004 | Wood | |
| 6,681,136 B2 | 1/2004 | Schuler et al. | |
| 6,684,105 B2 | 1/2004 | Cohen et al. | |
| 6,690,971 B2 | 2/2004 | Schauerte et al. | |
| 6,692,738 B2 | 2/2004 | MacLaughlin et al. | |
| 6,697,670 B2 | 2/2004 | Chomenky et al. | |
| 6,718,208 B2 | 4/2004 | Hill et al. | |
| 6,735,471 B2 | 5/2004 | Hill et al. | |
| 6,738,663 B2 | 5/2004 | Schroeppel et al. | |
| 6,749,598 B1 | 6/2004 | Keren et al. | |
| 6,786,904 B2 | 9/2004 | Doscher et al. | |
| 6,795,728 B2 | 9/2004 | Chornenky et al. | |
| 6,845,267 B2 | 1/2005 | Harrison et al. | |
| 6,850,801 B2 | 2/2005 | Kieval et al. | |
| 6,862,479 B1 | 3/2005 | Whitehurst et al. | |
| 6,865,416 B2 | 3/2005 | Dev et al. | |
| 6,885,888 B2 | 4/2005 | Rezai | |
| 6,916,656 B2 | 7/2005 | Walters et al. | |
| 6,927,049 B2 | 8/2005 | Rubinsky et al. | |
| 6,936,047 B2 | 8/2005 | Nasab et al. | |
| 6,939,345 B2 | 9/2005 | KenKnight et al. | |
| 6,939,346 B2 | 9/2005 | Kannenberg et al. | |
| 6,958,060 B2 | 10/2005 | Mathiesen et al. | |
| 6,969,388 B2 | 11/2005 | Goldman et al. | |
| 6,972,013 B1 | 12/2005 | Zhang et al. | |
| 6,978,174 B2 | 12/2005 | Gelfand et al. | |
| 6,985,774 B2 | 1/2006 | Kieval et al. | |
| 6,994,700 B2 | 2/2006 | Elkins et al. | |
| 6,994,706 B2 | 2/2006 | Chornenky et al. | |
| 7,004,911 B1 | 2/2006 | Tu et al. | |
| 7,054,685 B2 | 5/2006 | Dimmer et al. | |
| 7,063,679 B2 | 6/2006 | Maguire et al. | |
| 7,081,114 B2 | 7/2006 | Rashidi | |
| 7,081,115 B2 | 7/2006 | Taimisto | |
| 7,083,614 B2 | 8/2006 | Fjield et al. | |
| 7,122,019 B1 | 10/2006 | Kesten et al. | |
| 7,155,284 B1 | 12/2006 | Whitehurst et al. | |
| 7,191,015 B2 | 3/2007 | Lamson et al. | |
| 7,373,204 B2 | 5/2008 | Gelfand et al. | |
| 7,444,183 B2 | 10/2008 | Knudson et al. | |
| 2001/0044596 A1 | 11/2001 | Jaafar | |
| 2002/0002329 A1 | 1/2002 | Avitall | |
| 2002/0026222 A1 | 2/2002 | Schauerte et al. | |
| 2002/0026228 A1 | 2/2002 | Schauerte | |
| 2002/0032468 A1 | 3/2002 | Hill et al. | |
| 2002/0038137 A1 | 3/2002 | Stein | |
| 2002/0040204 A1 | 4/2002 | Dev et al. | |
| 2002/0045853 A1 | 4/2002 | Dev et al. | |
| 2002/0065541 A1 | 5/2002 | Fredricks et al. | |
| 2002/0072782 A1 | 6/2002 | Osorio et al. | |

| | | |
|---|---|---|
| 2002/0107553 A1 | 8/2002 | Hill et al. |
| 2002/0116030 A1 | 8/2002 | Rezai |
| 2002/0120304 A1 | 8/2002 | Mest |
| 2002/0165532 A1 | 11/2002 | Hill, et al. |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183682 A1 | 12/2002 | Darvish et al. |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0018367 A1 | 1/2003 | DiLorenzo |
| 2003/0040774 A1 | 2/2003 | Terry et al. |
| 2003/0045909 A1 | 3/2003 | Gross et al. |
| 2003/0050681 A1 | 3/2003 | Pianca et al. |
| 2003/0055422 A1 | 3/2003 | Lesh |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0100924 A1 | 5/2003 | Foreman et al. |
| 2003/0120270 A1 | 6/2003 | Acker |
| 2003/0125790 A1 | 7/2003 | Fastovsky et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0181963 A1 | 9/2003 | Pellegrino et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0199863 A1 | 10/2003 | Swanson et al. |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0127942 A1 | 7/2004 | Yomtov et al. |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0215186 A1 | 10/2004 | Cornelius et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0187579 A1 | 8/2005 | Danek et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2005/0288730 A1 | 12/2005 | Deem et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0089674 A1 | 4/2006 | Walters et al. |
| 2006/0095029 A1 | 5/2006 | Young et al. |
| 2006/0100667 A1 | 5/2006 | Machado et al. |
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0265015 A1 | 11/2006 | Demarais et al. |
| 2007/0066972 A1 | 3/2007 | Ormsby et al. |
| 2007/0142864 A1 | 6/2007 | Libbus et al. |
| 2007/0156200 A1 | 7/2007 | Kornet et al. |
| 2007/0208382 A1 | 9/2007 | Yun |
| 2007/0265687 A1 | 11/2007 | Deem et al. |
| 2007/0282376 A1 | 12/2007 | Shuros et al. |
| 2007/0282407 A1 | 12/2007 | Demarais et al. |
| 2007/0288070 A1 | 12/2007 | Libbus et al. |
| 2008/0004673 A1 | 1/2008 | Rossing et al. |
| 2008/0015659 A1 | 1/2008 | Zhang et al. |
| 2008/0039904 A1 | 2/2008 | Bulkes et al. |
| 2008/0091255 A1 | 4/2008 | Caparso et al. |
| 2008/0140150 A1 | 6/2008 | Zhou et al. |
| 2008/0213331 A1 | 9/2008 | Gelfand et al. |
| 2008/0255642 A1 | 10/2008 | Zarins et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2010/0010567 A1 | 1/2010 | Deem et al. |
| 2010/0057150 A1 | 3/2010 | Demarais et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0174282 A1 | 7/2010 | Demarais et al. |

| | | | |
|---|---|---|---|
| 2010/0191112 | A1 | 7/2010 | Demarais et al. |
| 2010/0222851 | A1 | 9/2010 | Deem et al. |
| 2010/0222854 | A1 | 9/2010 | Demarais et al. |
| 2010/0268307 | A1 | 10/2010 | Demarais et al. |
| 2011/0137298 | A1 | 6/2011 | Nguyen et al. |

FOREIGN PATENT DOCUMENTS

| | | | |
|---|---|---|---|
| DE | 3151180 A1 | 8/1982 | |
| EP | 0811395 A2 | 6/1997 | |
| EP | 1598024 | 11/2005 | |
| EP | 2092957 A1 | 8/2009 | |
| WO | WO-85/01213 | 3/1985 | |
| WO | WO-91/04725 | 4/1991 | |
| WO | WO9220291 | 11/1992 | |
| WO | WO-9220291 A1 | 11/1992 | |
| WO | WO-93/02740 | 2/1993 | |
| WO | WO-93/07803 | 4/1993 | |
| WO | WO-94/00188 | 1/1994 | |
| WO | WO-94/11057 A1 | 5/1994 | |
| WO | WO9411057 | 5/1994 | |
| WO | WO-96/04957 | 1/1995 | |
| WO | WO-/95/25472 A1 | 9/1995 | |
| WO | WO-95/25472 A1 | 9/1995 | |
| WO | WO-95/33514 | 12/1995 | |
| WO | WO-96/00039 A1 | 1/1996 | |
| WO | WO9600039 | 1/1996 | |
| WO | WO-96/11723 | 4/1996 | |
| WO | WO-97/13550 | 4/1997 | |
| WO | WO-9713463 A1 | 4/1997 | |
| WO | WO-9736548 A1 | 10/1997 | |
| WO | WO-97/49453 | 12/1997 | |
| WO | WO-98/37926 | 9/1998 | |
| WO | WO-/98/42403 A1 | 10/1998 | |
| WO | WO-98/43700 | 10/1998 | |
| WO | WO-98/43701 | 10/1998 | |
| WO | WO-98/48888 | 11/1998 | |
| WO | WO-99/33407 | 7/1999 | |
| WO | WO-99/51286 | 10/1999 | |
| WO | WO-99/52424 | 10/1999 | |
| WO | WO-01/26729 | 4/2001 | |
| WO | WO-0122897 A1 | 4/2001 | |
| WO | WO-0170114 A1 | 9/2001 | |
| WO | WO-02/09808 | 2/2002 | |
| WO | WO-02/26314 | 4/2002 | |
| WO | WO-02/053207 | 7/2002 | |
| WO | WO-02/070039 A2 | 9/2002 | |
| WO | WO-02/070047 | 9/2002 | |
| WO | WO-02/085448 | 10/2002 | |
| WO | WO02085192 | 10/2002 | |
| WO | WO-03/018108 | 3/2003 | |
| WO | WO-03/028802 | 4/2003 | |
| WO | WO-03/063692 | 8/2003 | |
| WO | WO-03/071140 A2 | 8/2003 | |
| WO | WO-03/076008 | 9/2003 | |
| WO | WO-03/082080 | 10/2003 | |
| WO | WO-03/082403 | 10/2003 | |
| WO | WO-2004/026370 | 4/2004 | |
| WO | WO-2004/026371 | 4/2004 | |
| WO | WO-2004/026374 | 4/2004 | |
| WO | WO-2004/030718 | 4/2004 | |
| WO | WO-2004/032791 | 4/2004 | |
| WO | WO-2004/107965 | 12/2004 | |
| WO | WO-2005014100 | 2/2005 | |
| WO | WO-2005016165 | 2/2005 | |
| WO | WO 2005/032646 | 4/2005 | |
| WO | WO-2005032646 | 4/2005 | |
| WO | WO-2005/065284 | 7/2005 | |
| WO | WO-2005/084389 A2 | 9/2005 | |
| WO | WO-2005/097256 A2 | 10/2005 | |
| WO | WO-2005/110528 A1 | 11/2005 | |
| WO | WO-2005/123183 | 12/2005 | |
| WO | WO-2006/007048 A2 | 1/2006 | |
| WO | WO-2006018528 A1 | 2/2006 | |
| WO | WO-2006/031899 A2 | 3/2006 | |
| WO | WO-2006022790 A1 | 3/2006 | |
| WO | WO-2006041847 | 4/2006 | |
| WO | WO-2006041881 | 4/2006 | |
| WO | WO-2007008954 A2 | 1/2007 | |
| WO | WO-2007035537 | 3/2007 | |
| WO | WO-2007078997 A2 | 7/2007 | |
| WO | WO-2007086965 | 8/2007 | |
| WO | WO-2007103879 | 9/2007 | |
| WO | WO-2007103881 | 9/2007 | |
| WO | WO-2007121309 | 10/2007 | |
| WO | WO-2007146834 | 12/2007 | |
| WO | WO-2008003058 | 1/2008 | |
| WO | WO-2008061150 | 5/2008 | |
| WO | WO-2008061152 | 5/2008 | |
| WO | WO-2008070413 | 6/2008 | |
| WO | WO2010078175 | 7/2010 | |
| WO | WO-2010078175 A1 | 7/2010 | |

OTHER PUBLICATIONS

"Renal Sympathetic—Nerve Ablation for Uncontrolled Hypertension". Krum et al. New England Journal of Med. 361;9.*
"Catheter-Based Sympathetic Renal Denervation" Rocha-Singh, Endovascular Today, Aug. 2009.*
"Catheter-based renal sympathetic denervation for resistant hypertension: a multicentre saftery and proof of principle cohort study." Krum et al. www.thelancet.com, Mar. 30, 2009.*
U.S. Appl. No. 11/504,117, Demarais et al.
U.S. Appl. No. 11/599,649, Demarais et al.
U.S. Appl. No. 11/599,723, Demarais et al.
U.S. Appl. No. 11/599,882, Demarais et al.
U.S. Appl. No. 11/599,890, Demarais et al.
U.S. Appl. No. 11/688,178, Levin et al.
U.S. Appl. No. 10/408,665, filed Apr. 8, 2003, Levin et al.
U.S. Appl. No. 10/900,199, filed Jul. 28, 2004, Gelfand.
U.S. Appl. No. 11/129,765, filed May 13, 2005, Deem.
U.S. Appl. No. 11/133,925, filed May 20, 2005, Gelfand.
U.S. Appl. No. 11/144,173, filed Jun. 3, 2005, Levin et al.
U.S. Appl. No. 11/144,298, filed Jun. 3, 2005, Levin et al.
U.S. Appl. No. 11/145,122, filed Jun. 3, 2005, Levin et al.
U.S. Appl. No. 11/189,563, filed Jul. 25, 2005, Deem.
U.S. Appl. No. 11/233,814, Denise Demarais.
U.S. Appl. No. 11/252,462, Denise Demarais.
U.S. Appl. No. 11/266,993, Demarais.
U.S. Appl. No. 11/324,188, Denise Demarais.
U.S. Appl. No. 11/363,867, Denise Demarais.
U.S. Appl. No. 11/368,577, Demarais.
U.S. Appl. No. 11/368,809, Denise Demarais.
U.S. Appl. No. 11/368,836, Demarais.
U.S. Appl. No. 11/368,949, Denise Demarais.
U.S. Appl. No. 11/368,971, Denise Demarais.
"2003 European Society of Hypertension—European Society of Cardiology guidelines for the management of arterial hypertension," Journal of Hypertension 2003, vol. 21, No. 6, pp. 1011-1053.
"Advanced Neuromodulation Systems' Comparison Chart," 1 page.
"Advances in the role of the sympathetic nervous system in cardiovascular medicine," 2001 SNS Report, No. 3, Springer, published with an educational grant from Servier, pp. 1-8.
"Cardiac Glycosides," Heart Disease—A Text Book of Cardiovascular Medicine vol. 2, Edited by Eugene Braunwald, 5th Edition, WB Saunders Company, pp. 480-481.
"Clinical Trials in Hypertension and Renal Diseases," Slide Source, www.hypertensiononline.org, 33 pages.
"ECM 830 Specifications Sheet," tech@genetronics.com, 20-001796-01 Rev D, 2 pages.
"Effects of Renal Failure on the Cardiovascular System," 5th Edition Heart Disease, A Textbook of Cardiovascular Medicine, vol. 2, Edited by Eugene Braunwald, W.B. Saunders Company, pp. 1923-1925.
"Electropermeabilization (Electroporation)," Cyto Pulse Sciences Inc., http://www.cytopulse.com/electroporation.html (last accessed Mar. 3, 2005), 3 pages.
"Electroporation based Technologies and Treatments," ESPE Newsletter No. 6, QLK 02002-2003, Jan. 2005, www.cliniporator.com, 4 pages.
"End-stage renal disease payment policies in traditional Medicare," Report to the Congress: Medicare Payment Policy, Mar. 2001, Medpac, pp. 123-138.
"Epidemiology of Renal Disease in Hypertension," slide presentation by hypertensiononline.org, 21 pages.

"Fact Book Fiscal Year 2003," National Institutes of Health National Heart, Lung, and Blood Institute, Feb. 2004, 197 pages.

"Heart Disease and Stroke Statistics—2004 update," American Heart Association, American Stroke Association, Dallas, Texas, ©2003 American Heart Association, 52 pages.

"Hypertension and Renal Disease: Mechanisms," Slide Show by www.hypertensiononline.org, 22 pages.

"Hypertension Incidence and Prevalence, Age Specific Rates, by Gender, B.C., 2001/2002," Graph., Chronic Disease Management, May 2003, British Columbia Ministry of Health Services, 1 page.

Implantable Pump—The Medtronic MiniMed 2007 Implantable Insulin Pump System, Medtronic MiniMed 2004, 4 pages.

"Infumedics Inc.," Background and products paper and comparison of Medtronic SynchroMed II and Infumedics Prometra pumps, 3 pages.

"Introduction to Autonomic Pharmacology," Chapter 3, Part 2 Autonomic Pharmacology, pp. 18-26.

"Market for infusion pumps grows with an aging population," NWL 97-01, The BBI Newsletter, vol. 20, No. 2, Feb. 1, 1997, American Health Consultants Inc., 6 pages.

"PHCL 762 Pharmacology of the Autonomic Nervous System," Chapter 2 and 6.8 in Mosby, http://www.kumc.edu/research/medicine/pharmacology/CAl/phcl762.html, last accessed Aug. 24, 2004, 14 pages.

"Programmable Infusion System," Pumps and Pump Selection, Medtronic Pain Therapies, Medtronic, Inc. Sep. 5, 2001, 2 pages.

"Pulmonary Concepts in Critical Care Breath Sounds," http://mbob.tripod.com/breath.htm, last accessed Aug. 23, 2004, 5 pages.

"Pulmonary Function Testing," http://jan.ucc.nau.edu/~daa/lecture/pft.htm, last accessed Aug. 23, 2004, 8 pages.

"Renal Parenchymal Disease," Ch. 26, 5th Edition Heart Disease, A Textbook of Cardiovascular Medicine vol. 2, Edited by Eugene Braunwald, WB Saunders Company, pp. 824-825.

"Sensorcaine-MPF Spinal Injection," informational document, AstraZeneca 2001, 2 pages.

"Summary," Critical Reviews in Biomedical Engineering, vol. 17, Issue 5, 1989, pp. 515-529.

"The Antihypertensive and Lipid-Lowering Treatment to Prevent Heart Attack Trial," ALLHAT Research Group, JAMA 2002, vol. 288, pp. 2981-2997.

Aars, H. And S. Akre, "Reflex Changes in Sympathetic Activity and Arterial Blood Pressure Evoked by Afferent Stimulation of the Renal Nerve," Feb. 26, 1999, Acta Physiol. Scand., vol. 78, 1970, pp. 184-188.

Abramov, G.S. et al., "Alteration in sensory nerve function following electrical shock," Burns vol. 22, No. 8, ©1996 Elsevier Science Ltd., pp. 602-606.

Achar, Suraj, M.D. and Suriti Kundu, M.D., "Principles of Office Anesthesia: Part I. Infiltrative Anesthesia," Office Procedures, American Family Physician, Jul. 1, 2002, vol. 66, No. 1, pp. 91-94.

Agnew, William F. et al., "Evolution and Resolution of Stimulation-Induced Axonal Injury in Peripheral Nerve," May 21, 1999, Muscle and Nerve, vol. 22, Oct. 1999, ©1999 John Wiley & Sons, pp. 1393-1402.

Ahadian, Farshad M., M.D., "Pulsed Radiofrequency Neurotomy: Advances in Pain Medicine," Current Pain and Headache Reports 2004, vol. 8, © 2004 Current Science Inc., pp. 23-30.

Alford, J.Winslow, M.D. and Paul. D. Fadale, M.D., "Evaluation of Postoperative Bupivacaine Infusion for Pain Management After Anterior Cruciate Ligament Reconstruction," The Journal of Arthroscopic and Related Surgery October, vol. 19, No. 8, © 2003 Arthroscopy Association of North America, pp. 855-861.

Andrews, B.T. et al., "The use of surgical sympathectomy in the treatment of chronic renal pain," Mar. 5, 1997, British Journal of Urology, vol. 80, © 1997 British Journal of Urology, pp. 6-10.

Antman, Elliott M. and Eugene Braunwald, "Chapter 37~Acute Myocardial Infarction," Heart Disease—A Textbook of Cardiovascular Medicine, 5th Edition, vol. 2, 1997, Edited by Eugene Braunwald, pp. 1184-1288.

Archer, Steffan et al., "Cell Reactions to Dielectrophoretic Manipulation," Mar. 1, 1999, Biochemical and Biophysical Research Communications, 1999 Academic Press, pp. 687-698.

Arias, Manuel J., M.D., "Percutaneous Radio Frequency Thermocoagulation with Low Temperature in the Treatment of Essential Glossopharyngeal Neuralgia," Surg. Neurol. 1986, vol. 25, © 1986 Elsevier Science Publishing Co. Inc., pp. 94-96.

Aronofsky, David H., D.D.S., "Reduction of dental postsurgical symptoms using nonthermal pulsed high-peak-power electromagnetic energy," Oral Surg., Nov. 1971, vol. 32, No. 5, pp. 688-696.

Aspelin, Peter, M.D., Ph.D. et al, "Nephrotoxic Effects in High-Risk Patients Undergoing Angiography," Feb. 6, 2003, New England Journal of Medicine 2003, vol. 348, No. 6, 2003 Massachusetts Medical Society, pp. 491-499.

Augustyniak, Robert A. et al., "Sympathetic Overactivity as a Cause of Hypertension in Chronic Renal Failure," Aug. 14, 2001, Journal of Hypertension, 2002, vol. 20, 2002 Lippincott Williams & Wilkins, pp. 3-9.

Awwad, Ziad M., FRCS and Bashir A. Atiyat, GBA, JBA, "Pain relief using continuous bupivacaine infusion in the paravertebral space after loin incision," May 15, 2004, Saudi Med. J. 2004, vol. 25, No. 10, pp. 1369-1373.

Badyal, D.K., H. Lata and A.P. Dadhich, "Animal Models of Hypertension and Effect of Drugs," Aug. 19, 2003, Indian Journal of Pharmacology 2003, vol. 35, pp. 349-362.

Baker, Carol E. et al., "Effect of pH of Bupivacaine on Duration of Repeated Sciatic Nerve Blocks in the Albino Rat," Anesth. Analg. 1991, vol. 72, © 1991 The International Anesthesia Research Society, pp. 773-778.

Balazs, Tibor, "Development of Tissue Resistance to Toxic Effects of Chemicals," Jan. 26, 1974, Toxicology, vol. 2, ©1974 Elsevier/North Holland, Amsterdam, pp. 247-255.

Barrett, Carolyn J. et al., "Long-term control of renal blood flow: what is the role of renal nerves?" Jan. 4, 2001, Am. J. Physiol. Regulatory Integrative Comp. Physiol. 2001, vol. 280, © 2001 the American Physiological Society, pp. R1534-R1545.

Barrett, Carolyn J. et al., "What Sets the Long-Term Level of Renal Sympathetic Nerve Activity?," May 12, 2003, Integrative Physiology, Circulation Research 2003, vol. 92, © 2003 American Heart Association, pp. 1330-1336.

Bassett, C. Andrew L. et al., "Augmentation of Bone Reapair by Inductively Coupled Electromagnetic Fields," May 3, 1974, Science, vol. 184, pp. 575-577.

Bassett, C. Andrew L., "Fundamental and Practical Aspects of Therapeutic Uses of Pulsed Electromagnetic Fields (PEMFs)," Critical Reviews in Biomedical Engineering, vol. 17, No. 5, 1989, pp. 451-514.

Beebe, Stephen J. et al., "Nanosecond Pulsed Electric Field (nsPEF) Effects on Cells and Tissues: Apoptosis Induction and Tumor Growth Inhibition," Oct. 11, 2001, IEEE Transactions on Plasma Science, vol. 30, No. 1, Feb. 2002, © 2002 IEEE, pp. 286-292.

Beebe, Stephen J. et al., "Nanosecond pulsed electric fields modulate cell function through intracellular signal transduction mechanisms," Apr. 8, 2004, Physiological Measurement, vol. 25, © 2004 IOP Publishing Ltd., pp. 1077-1093.

Berde, Charles and Gary R. Strichartz, "Local Anesthetics," Anesthesia, Chapter 13, 5th addition, Churchill-Livingston, Philadelphia 2000, pp. 491-521.

Bhadra, Niloy and Kevin L. Kilgore, "Direct Current Electrical Conduction Block of Peripheral Nerve," Feb. 25, 2004, IEEE Transactions on Neural Systems and Rehabilitation Engineering, vol. 12, No. 3, Sep. 2004, pp. 313-324.

Bhatt, Deepak L. et al., "Rhabdomyolysis Due to Pulsed Electric Fields," May 11, 1989, Plastic and Reconstructive Surgery Jul. 1990, pp. 1-11.

Bigler, D. et al., "Tachyphylaxis during postoperative epidural analgesia—new insights," Apr. 15, 1987, Letter to the Editor, Acta Anesthesiol. Scand. 1987, vol. 31, pp. 664-665.

Binder, Allan et al., "Pulsed Electromagnetic Field Therapy of Persistent Rotator Cuff Tendinitis," The Lancet, Saturday Mar. 31, 1984, The Lancet Ltd., pp. 695-698.

Black, Henry R., M.D., "Resistant Hypertension 2004," presentation at Rush University Medical Center, Jul. 15, 2004, 40 pages.

Blad, B., et al., "An Electrical Impedance index to Assess Electroporation in Tissue," Tissue and Organ (Therapy) 2001, Oslo, pp. 31-34.

Blair, M.L. et al., "Sympathetic activation cannot fully account for increased plasma renin levels during water deprivation," Sep. 23, 1996, Am J Physiol 1997, vol. 272, © 1997 the American Physiological Society, pp. R1197-R1203.

Blomberg, Sture G., M.D., Ph.D., "Long-Term Home Self-Treatment with High Thoracic Epidural Anesthesia in Patients with Severe Coronary Artery Disease," Mar. 29, 1994, Anesth. Analg. 1994, vol. 79, © 1994 International Anesthesia Research Society, pp. 413-421.

Cahana, A. et al., "Acute Differential Modulation of Synaptic Transmission and Cell Survival During Exposure to Pulsed and Continuous Radiofrequency Energy," The Journal of Pain, May 2003, vol. 4, No. 4, © 2003 by the American Pain Society, pp. 197-202.

Cahana, Alex, M.D., "Pulsed Radiofrequency: A Neurobiologic and Clinical Reality," May 17, 2005, Anesthesiology 2005, vol. 103, No. 6, Dec. 2005 © 2005 American Society of Anesthesiologists, Inc., Lippincott Williams & Wilkins, Inc., p. 1311.

Calaresu, F.R. et al., "Haemodynamic Responses and Renin Release During Stimulation of Afferent Renal Nerves in the Cat," Aug. 12, 1975, J. Physiol. 1976, vol. 255, pp. 687-700.

Campese, V.M. et al., "Renal Afferent Denervation Prevents the Progression of Renal Disease in the Renal Ablation Model of Chronic Renal Failure in the Rat," Jun. 13, 1995, American Journal of Kidney Diseases 1995, vol. 26, No. 5, 1995 the National Kidney Foundation, Inc., pp. 861-865.

Campese, V.M., "A new model of neurogenic hypertension caused by renal injury: pathophysiology and therapeutic implications," Clin. Exp. Nephrol 2003, vol. 7, © 2003 Japanese Society of Nephroloogy, pp. 167-171.

Campese, V.M., "Neurogenic factors and hypertension in chronic renal failure," Journal of Nephrology, vol. 10, No. 4, © 1997 Societa Italiana di Nefrologia, pp. 184-187.

Carls, G., et al., "Electrical and magnetic stimulation of the intercostal nerves: a comparative study," Electromyogr. clin. Neurophysiol., vol. 37, 1997, pp. 509-512.

Carlson, Scott H. and J. Michael Wyss, "e-Hyertension, Opening New Vistas," Introductory Commentary, Hypertension 2000, vol. 35, American Heart Association, Inc., 2000, p. 538.

Chang, Donald C., "Cell poration and cell fusion using an oscillating electric field," Biophysical Journal, vol. 56, Oct. 1989, Biophysical Society, pp. 641-652.

Chobanian, Aram V. et al., "Seventh Report of the Joint National Committee on Prevention, Detection, Evaluation, and Treatment of High Blood Pressure," Nov. 6, 2003, Hypertension 2003, vol. 42, © 2003 American Heart Association, Inc., pp. 1206-1252.

Codman 3000, Implantable Constant-Flow Infusion Pump Pamphlet, For Continuous Intrathecal Drug Delivery, 2 pages.

Conradi, E., Ines Helen Pages, "Effects of Continuous and Pulsed Microwave Irradiation on Distribution of Heat in the Gluteal Region of Minipigs," Scand. J. Rehab. Med., vol. 21, 1989, pp. 59-62.

Converse Jr., R.L. et al., "Sympathetic Overactivity in Patients with Chronic Renal Failure," New England Journal of Medicine, Dec. 31, 1992, vol. 327 (27), pp. 1912-1918.

Cosman, Eric R., Jr. et al., "Electric and Thermal Field Effects in Tissue Around Radiofrequency Electrodes," Pain Medicine, vol. 6, No. 6, 2005, American Academy of Pain Medicine, pp. 405-424.

Cosman, Eric R., Ph.D., "A Comment on the History of the Pulsed Radiofrequency Technique for Pain Therapy," Anesthesiology Dec. 2005, vol. 103, No. 6, © 2005 American Society of Anesthesiologists, Inc. Lippincott Williams & Wilkins, Inc., p. 1312.

Crawford, William H. et al., "Pulsed Radio Frequency Therapy of Experimentally Induced Arthritis in Ponies," Dec. 18, 1989, Can. J. Vet. Res. 1991, vol. 55, pp. 76-85.

Dahm, Peter et al., "Efficacy and Technical Complications of Long-Term Continuous Intraspinal Infusions of Opioid and/or Bupivacaine in Refractory Nonmalignant Pain . . . ," Oct. 6, 1997, The Clinical Journal of Pain 1998, vol. 14, No. 1, © 1998 Lippincott-Raven Publishers, pp. 4-16.

Dahm, Peter O. et al., "Long-Term Intrathecal Infusion of Opioid and/or Bupivacaine in the Prophylaxis and Treatment of Phantom Limb Pain," Neuromodulation 1998, vol. 1, No. 3, © 1998 International Neuromodulation Society, pp. 111-128.

Dang, Nicholas C. et al., "A Novel Approach to Increase Total Urine Output in Heart Failure: Renal Nerve Blockade," ACC 2005 poster, 1 page.

Davalos, R. et al., "Electrical Impedance Tomography for Imaging Tissue Electroporation," Jul. 25, 2003, IEEE Transactions on Biomedical Engineering, vol. 51, No. 5, May 2004, IEEE 2004, pp. 761-767.

Davalos, R.V. et al., "Tissue Ablation with Irreversible Electroporation," Sep. 7, 2004, Annals of Biomedical Engineering, vol. 33, No. 2, © 2005 Biomedical Engineering Society, pp. 223-231.

De Leeuw, Peter W. et al., "Renal Vascular Tachyphylaxis to Angiotensin II: Specificity of the Response for Angiotensin," Dec. 28, 1981, Life Sciences, vol. 30, © 1982 Pergamon Press Ltd., pp. 813-819.

Deng, Jingdong et al., "The Effects of Intense Submicrosecond Electrical Pulses on Cells," Nov. 26, 2002, Biophysical Journal, vol. 84, Apr. 2003, © 2003 Biophysical Society, pp. 2709-2714.

Denton, Kate M. et al., "Differential Neural Control of Glomerular Ultrafiltration," Jan. 30, 2004, Proceedings of the Australian Physiological and Pharmacological Society Symposium: Hormonal, Metabolic and Neural Control of the Kidney, Clinical and Experimental Pharmacology and Physiology (2004), 31, pp. 380-386.

Dev, Nagendu B., Ph.D. et al., "Intravascular Electroporation Markedly Attenuates Neointima Formation After Balloon Injury of the Carotid Artery in the Rat," Journal of Interventional Cardiology, vol. 13, No. 5, 2000, pp. 331-338.

Dev, Nagendu B., Ph.D. et al., "Sustained Local Delivery of Heparin to the Rabbit Arterial Wall With an Electroporation Catheter," May 5, 1998, Catheterization and Cardiovascular Diagnosis 1998, vol. 45, © 1998 Wiley-Liss Inc., pp. 337-345.

DiBona, G., "Neural Control of the Kidney: Functionally Specific Renal Sympathetic Nerve Fibers," Starling Lecture, Am J Physiol Regulatory Integrative Comp Physiol 2000, 279, 2000 The American Physiological Society, pp. R1517-R1524.

Dibona, Gerald F., "Sympathetic Nervous System and the Kidney in Hypertension," Current Opinion in Nephrology and Hypertension 2002, vol. 11, 2002 Lippincott Williams & Wilkins, pp. 197-200.

Dibona, Gerald F. and Linda L. Sawin, "Role of renal nerves in sodium retention of cirrhosis and congestive heart failure," Sep. 27, 1990, Am J Physiol 1991, vol. 260, © 1991 the American Physiological Society, pp. R298-R305.

Dibona, Gerald F. and Ulla C. Kopp, "Neural Control of Renal Function," Physiological Reviews Jan. 1997, vol. 77, No. 1, © 1997 American Physiological Society, pp. 75-197.

Dibona, Gerald F. and Ulla C. Kopp, "Role of the Renal Sympathetic Nerves in Pathophysiological States," Neural Control of Renal Function, vol. 77, pp. 142-197.

Dibona, Gerald F., "Functionally Specific Renal Sympathetic Nerve Fibers: Role in Cardiovascular Regulation," Mar. 6, 2001, American Journal of Hypertension 2001, vol. 14, 2001 American Journal of Hypertension, Ltd. Published by Elsevier Science Inc., pp. 163S-170S.

Dibona, Gerald F., "Nervous Kidney—Interaction Between Renal Sympathetic Nerves and the Renin-Angiotensin System in the Control of Renal Function," Jun. 21, 2000, Hypertension 2000, vol. 36, 2000 American Heart Association, Inc., pp. 1083-1088.

Dibona, Gerald F., "Neural Control of the Kidney—Past, Present, and Future," Nov. 4, 2002, Novartis Lecture, Hypertension 2003, vol. 41, part 2, © 2002 American Heart Association, pp. 621-624.

Dibona, Gerald F., "Peripheral and Central Interactions between the Renin-Angiotensin System and the Renal Sympathetic Nerves in Control of Renal Function," Annals New York Academy of Sciences, pp. 395-406.

Dibona, Gerald F., "Renal Innervation and Denervation: Lessons from Renal Transplantation Reconsidered," Artificial Organs, vol. 11, No. 6, Raven Press Ltd., © 1987 International Society for Artificial Organs, pp. 457-462.

Dibona, Gerald F., "The Sympathetic Nervous System and Hypertension," Dec. 4, 2003, Hypertension Highlights, Hypertension Feb. 2004, vol. 43, © 2004 American Heart Association, pp. 147-150.

Dibona, Gerald F., L.L. Sawin, "Effect of renal denervation on dynamic autoregulation of renal blood flow," Feb. 12, 2004, Am J Physiol Renal Physiol 286, pp. F1209-F1218.

Dibona, Gerald F., Susan Y. Jones, "Dynamic Analysis of Renal Nerve Activity Responses to Baroreceptor Denervation in Hypertensive Rats," Sep. 19, 2000, Hypertension Apr. 2001, © 2001 American Heart Association, pp. 1153-1163.

Dorros, Gerald, M.D., "Renal Artery Stenting State of the Art," presentation, TCT, Washington D.C., Sep. 2003, 27 pages.

Dueck, Ron, M.D., "Noninvasive Cardiac Output Monitoring," The Cardiopulmonary and Critical Care Journal, Chest, vol. 120, sec. 2, Aug. 2001, American College of Chest Physicians 2005, pp. 339-341, 5 pages.

Dunn, Matthew D. et al., "Laparoscopic Nephrectomy in Patients With End-Stage Renal Disease and Autosomal Dominant Polycystic Kidney Disease," Oct. 25, 1999, American Journal of Kidney Diseases Apr. 2000, vol. 35, No. 4, © 2000 National Kidney Foundation, Inc., pp. 720-725.

Durand, D.M., "Electrical Field Effects in Hyperexcitable Neural Tissue: A Review," Radiation Protection Dosimetry, vol. 106, No. 4, 2003, Nuclear Technology Publishing, pp. 325-331.

Erdine, Serap and Alev Arat-Ozkan, "Resistant Hypertension," European Society of Hypertension Scientific Newsletter: Update on Hypertension Management, 2003, vol. 4, No. 15, 2 pages.

Fareed, Jawad, Ph.D. et al., "Some Objective Considerations for the Use of Heparins and Recombinant Hirudin in Percutaneous Transluminal Coronary Angioplasty," Seminars in Thrombosis and Hemostasis 1991, vol. 17, No. 4, © 1991 Thieme Medical Publishers, Inc., pp. 455-470.

Ferguson, D.R. et al., "Responses of the pig isolated renal artery to transmural electrical stimulation and drugs," Dec. 7, 1984, Br. J. Pharmac. 1985, vol. 84, © 1985 The Macmillan Press Ltd., pp. 879-882.

Fernandez-Ortiz, Antonio et al., "A New Approach for Local Intravascular Drug Deliver—Iontophoretic Balloon,," Intravascular Iontophoretic Local Delivery, Circulation, vol. 89, No. 4, Apr. 1994, pp. 1518-1522.

Fields, Larry E. et al, "The Burden of Adult Hypertension in the United States 1999 to 200—A Rising Tide," May 18, 2004, © 2004 the American Heart Association, Hypertension Oct. 2004, pp. 1-7.

Freeman, Scott A. et al., "Theory of Electroporation of Planar Bilayer Membranes: Predictions of the Aqueous Area, Change in Capacitance, and Pore-Pore Separation," Feb. 23, 1994, Biophysical Journal, Jul. 1994, vol. 67, © 1994 by the Biophysical Society, pp. 42-56.

Fukuoka, Yuko et al., "Imaging of neural conduction block by neuromagnetic recording," Oct. 16, 2002, Clinical Neurophysiology 2002, vol. 113, © 2002 Elsevier Science Ireland Ltd., pp. 1985-1992.

Gami, Apoor S., M.D. and Vesna D. Garovic, M.D., "Contrast Nephropathy After Coronary Angiography," Mayo Clin Proc. 2004, vol. 79, 2004 Mayo Foundation for Medical Education and Research, pp. 211-219.

Gattone II, Vincent H. et al., "Contribution of Renal Innervation to Hypertension in Polycystic Kidney Disease in the Rat," University of Chicago Section of Urology, 16 pages.

Gaylor, D.C. et al., "Significance of Cell Size and Tissue Structure in Electrical Trauma," Jan. 26, 1998, J. Theor. Biol. 1988, vol. 133, © 1988 Academic Press Limited, pp. 223-237.

Gehl, Julie et al., "In vivo electroporation of skeletal muscle: threshold, efficacy and relation to electric field distribution," Biochimica et Biophysica Acta, 1428, 1999, Elsevier Science B.V. 1999, pp. 233-240.

Ghoname, El-sayed A. et al., "Percutaneous electrical nerve stimulation: an alternative to TENS in the management of sciatica," Apr. 26, 1999, Pain 1999, vol. 83, © 1999 International Association for the Study of Pain / Published by Elsevier Science B.V., pp. 193-199.

Gimple, M.D., Lawrence et al., "Effect of Chronic Subcutaneous or Intramural Administration of Heparin on Femoral Artery Restenosis After Balloon Angioplasty in Hypercholesterolemic Rabbits" Laboratory Investigation, Circulation, vol. 86, No. 5, Nov. 1992, pp. 1536-1546.

Goldberger, Jeffrey J. et al., "New technique for vagal nerve stimulation," Jun. 2, 1999, Journal of Neuroscience Methods 91, © 1999 Elsevier Science B.V., pp. 109-114.

Gorbunov, F.E. et al., "The Use of Pulsed and Continuous Short Wave Diathermy (Electric Field) in Medical Rehabilitation of the Patients with Guillain-Barre Syndrome and Other Peripheral Myelinopathies," May 6, 1994, 5 pages (most of article in Russian language).

Greenwell, T.J. et al., "The outcome of renal denervation for managing loin pain haematuria syndrome," Oct. 30, 2003, Institute of Urology and Nephrology, London, UK, © 2004 BJU International, 4 pages.

Gruberg, Luis, M.D. et al., "The Prognostic Implications of Further Renal Function Deterioration Within 48 h of Interventional Coronary Procedures in Patients with Pre-existent Chronic Renal Insufficiency," Jun. 19, 2000, Journal of the American College of Cardiology 2000, vol. 36, No. 5, © 2000 by the American College of Cardiology, pp. 1542-1548.

Hajjar, Ihab, M.D., M.S. and Theodore A. Kotchen, M.D., "Trends in Prevalence, Awareness, Treatment, and Control of Hypertension in the United States, 1988-2000," JAMA, Jul. 9, 2003, vol. 290, No. 2, pp. 199-206.

Hamza, M.D., Mohamed A. et al., "Effect of the Duration of Electrical Stimulation on the Analgesic Response in Patients with Low Back Pain," Anesthesiology, vol. 91, No. 6, Dec. 1999, © 1999 American Society of Anesthesiologists, Inc., pp. 1622-1627.

Han, Hyo-Kyung and Gordon L. Amidon, "Targeted Prodrug Design to Optimize Drug Delivery," Mar. 21, 2000, AAPS Pharmsci. 2000, vol. 2, No. 1, article 6, pp. 1-11.

Heida, Tjitske et al., "Investigating Membrane Breakdown of Neuronal Cells Exposed to Nonuniform Electric Fields by Finite-Element Modeling and Experiments," May 9, 2002. IEEE Transactions on Biomedical Engineering, vol. 49, No. 10, Oct. 2002, © 2002 IEEE, pp. 1195-1203.

Higuchi, Yoshinori, M.D., Ph.D. et al., "Exposure of the Dorsal Root Ganglion in Rats to Pulsed Radiofrequency Currents Activates Dorsal Horn Lamina I and II Neurons," Dec. 4, 2001, Experimental Studies, Neurosurgery, vol. 50, No. 4, Apr. 2002, pp. 850-856.

Hildebrand, Keith R., D.V.M., Ph.D. et al., "Stability, Compatibility, and Safety of Intrathecal Bupivacaine Administered Chronically via an Implantable Delivery System," May 18, 2001, The Clinical Journal of Pain, vol. 17, No. 3, © 2001 Lippincott Williams & Wilkins Inc., pp. 239-244.

Hing, Esther, M.P.H. and Kimberly Middleton, B.S.N., M.P.H., "National Hospital Ambulatory Medical Care Survey: 2001 Outpatient Department Summary," Aug. 5, 2003, Advance Data From Vital and Health Statistics, No. 338, CDC, 32 pages.

Hopp, Francis A. and Jeanne L. Seagard, "Respiratory Responses to Selective Blockade of Carotid Sinus Baroreceptors in the Dog," Jun. 22, 2005, Am J Physiol Regul Integr Comp Physiol 1998, vol. 275, 2005 American Physiological Society, pp. R10-R18.

Norwich, Tamara, M.D., "New Advances in the Diagnosis and Management of Acute Decompensated Heart Failure," the Heart.org Satellite program, Rapid Review, CME Symposium presented on Nov. 8, 2004 at the Sheraton New Orleans Hotel, 4 pages.

Huang, Wann-Chu et al. "Renal Denervation Prevents and Reverses Hyperinsulinemia-Induced Hypertension in Rats," Mar. 25, 1998, Hypertension 1998, vol. 32, 1998 American Heart Association, Inc., pp. 249-254.

Huang, Yifei et al., "Remodeling of the chronic severely failing ischemic sheep heart after coronary microembolization: functional, energetic, structural, and cellular responses," Jan. 8, 2004, Am J Physiol. 2004, vol. 286, © 2004 the American Physiological Society, pp. H2141-H2150.

Hughes, Gordon B., M.D. et al., "A Comparative Study of Neuropathologic Changes Following Pulsed and Direct Current Stimulation of the Mouse Sciatic Nerve," Jun. 27, 1980, American Journal of Otolaryngology, Nov. 1980, vol. 1, No. 5, pp. 378-384.

Israili, Z.H., "Clinical pharmacokinetics of angiotensin II (AT) receptor blockers in hypertension," Journal of Human Hypertension 2000, Macmillan Publishers Ltd., vol. 14, pp. S73-S86.

Janssen, Ben J.A. et al., "Effects of complete renal denervation and selective afferent renal denervation on the hypertension induced by intrarenal norepinephrine infusion on conscious rats," Jan. 4, 1989, Journal of Hypertension 1989, vol. 7, No. 6, © 1989 Current Science Ltd., pp. 447-455.

Johansson, Bjorn, "Electrical Membrane Breakdown, A Possible Mediator of the Actions of Electroconvulsive Therapy," Medical Hypotheses 1987, vol. 24, © 1987 Longman Group UK Ltd., pp. 313-324.

Jorgensen, William A. et al., "Electrochemical Therapy of Pelvic Pain: Effects of Pulsed Electromagnetic Fields (PEMF) on Tissue Trauma," Eur. J. Surg. 1994, vol. 160, Suppl. 574, © 1994 Scandinavian University Press, pp. 83-86.

Joshi, R.P. et al., "Improved energy model for membrane electroporation in biological cells subjected to electical pulses," Apr. 9, 2002, Physical Review E, vol. 65, 041920-1, © 2002 The American Physical Society, 8 pages.

Joshi, R.P. et al., "Self-consistent simulations of elctroporation dynamics in biological cells subjected to ultrashort electrical pulses," Jun. 21, 2001, Physical Review E, vol. 64, 011913, © 2001The American Physical Society, pp. 1-10.

Joshi, R.P., K.H. Schoenbach, "Mechanism for membrane electroporation irreversibility under high-intensity, ultrashort electrical pulse conditions," Nov. 11, 2002, Physical Review 2002, E 66, © 2002 The American Physical Society, pp. 052901-1-052901-4.

Kanduser, Masa et al., "Effect of surfactant polyoxyethylene glycol $(C_{12}E_8)$ on electroporation of cell line DC3F," Aug. 20, 2002, Colloids and Surfaces A: Physiochem. Eng. Aspects 2003, vol. 214, © 2002 Elsevier Science B.V., pp. 205-217.

Katholi, Richard E., "Renal nerves in the pathogenesis of hypertension in experimental animals and humans," Am J Physiol., vol. 245, © 1983 the American Physiological Society, pp. F1-F14.

Kelleher, Catherine L. et al., "Characteristics of Hypertension in Young Adults With Autosomal Dominant Polycystic Kidney Disease Compared With the General U.S. Population," Jun. 9, 2004, American Journal of Hypertension 2004, pp. 1029-1034.

King, Ronald W.P., "Nerves in a Human Body Exposed to Low-Frequency Electromagnetic Fields," Jun. 7, 1999, IEEE Transactions on Biomedical Engineering Dec. 1999, vol. 46, No. 12, © 1999 IEEE, pp. 1426-1431.

Kinney, Brian M., M.D., "High-Tech Healing—The evolution of therapeutic electromagnetic fields in plastic surgery," Plastic Surgery Products, Jun. 2004, pp. 32-36, 3 pages.

Kok, R.J. et al., "Specific Delivery of Captopril to the Kidney with the Prodrug Captopril-Lysozyme," Aug. 16, 1998, The Journal of Pharmacology and Experimental Therapeutics, vol. 288, No. 1, © 1999 by the American Society for Pharmacology and Experimental Therapeutics, pp. 281-285.

Kon, Valentina, "Neural Control of Renal Circulation," Miner Electrolyte Metab 1989, vol. 15, © 1989 S. Karger AG, pp. 33-43.

Koyama, Shozo et al., "Relative Contribution of Renal Nerve and Adrenal Gland to Renal Vascular Tone During Prolonged Canine Hemorrhagic Hypotension," Sep. 24, 1992, Circulatory Shock 1993, vol. 39, © 1993 Wiley-Liss Inc., pp. 269-274.

Kozak, Lola Jean, Ph.D. et al., "National Hospital Discharge Survey: 2001 Annual Summary with Detailed Diagnosis and Procedure Data," Vital Health Statistics, Series 13, No. 156, Jun. 2004, CDC, 206 pages.

Lafayette, Richard A., M.D., "How Does Knocking Out Angiotensin II Activity Reduce Renal Injury in Mice?" Jun. 14, 1999, Journal Club, American Journal of Kidney Diseases, vol. 35, No. 1, Jan. 2000, © 2000 National Kidney Foundation Inc., pp. 166-172.

Lavie, Peretz, Ph.D. and Victor Hoffstein, M.D., "Sleep Apnea Syndrome: A Possible Contributing Factor to Resistant Hypertension," Jun. 2001, Sleep 2001, vol. 24, No. 6, pp. 721-725.

Lee, Raphael C. and Jurgen Hannig, "Membrane Biology and Biophysics," Chapter 25, Surgical Research, © 2001 Academic Press, pp. 297-305.

Lee, Raphael C. et al., "Biophysical Injury Mechanisms in Electrical Shock Trauma," Annu. Rev. Biomed. Eng., 2000, vol. 02, Copyright © 2000 by Annual Reviews, pp. 477-509.

Lee, Raphael C. et al., "Clinical Sequelae Manifested in Electrical Shock Survivors," Presentation by the Electrical Trauma Research Program, The University of Chicago, 37 pages.

Lee, Raphael C., M.D., Sc.D. and Michael S. Kolodney, S.B., "Electrical Injury Mechanisms: Electrical Breakdown of Cell Membranes," Oct. 1, 1986, Plastic and Reconstructive Surgery Nov. 1987, vol. 80, No. 5, pp. 672-679.

Ligtenberg, Gerry, M.D. et al., "Reduction of Sympathetic Hyperactivity by Enalapril in Patients with Chronic Renal Failure," Apr. 29, 1999, New England Journal of Medicine 1999, vol. 340, No. 17, © 1999 Massachusetts Medical Society, pp. 1321-1328.

Lin, Vernon W. H. et al, "High intensity magnetic stimulation over the lumbosacral spine evokes antinociception in rats," Apr. 16, 2002, Clinical Neurophysiology, vol. 113, © 2002 Elsevier Science Ireland Ltd., pp. 1006-1012.

Lipfert, Peter, M.D. et al., "Tachyphylaxis to Local Anesthetics Does Not Result From Reduced Drug Effectiveness at the Nerve Itself," Aug. 3, 1988, Anesthesiology 1989, vol. 70, pp. 71-75.

Lohmeier Thomas E. et al, "Baroreflexes prevent neurally induced sodium retention in angiotensin hypertension," Am. J. Physiol. Regulatory Integrative Comp. Physiol., vol. 279, © 2000 the American Physiological Society, pp. R1437-R1448.

Lohmeier, Thomas E. and Drew A. Hildebrandt, "Renal Nerves Promote Sodium Excretion in Angiotensin-Induced Hypertension," Oct. 20, 1997, Hypertension 1998, vol. 31, Part 2, © 1998 American Heart Association, Inc., pp. 429-434.

Lohmeier, Thomas E. et al., "Prolonged Activation of the Baroflex Produces Sustained Hypotension," Harry Goldblatt Award, Nov. 26, 2003, Hypertension 2004, vol. 43, part 2, © 2004 American Heart Association, Inc., pp. 306-311.

Lohmeier, Thomas E. et al., "Renal Nerves Promote Sodium Excretion During Long-Term Increases in Salt Intake," Oct. 23, 1998, Hypertension 1999, vol. 33, part 2, © 1999 American Heart Association, pp. 487-492.

Lohmeier, Thomas E. et al., "Sustained influence of the renal nerves to attenuate sodium retention in angiotensin hypertension," Apr. 13, 2001, Am J Physiol Regulatory Integrative Comp. Physiol., vol. 281, © 2001 the American Physiological Society, pp. R434-R443.

Lohmeier, Thomas E., "Interactions Between Angiotensin II and Baroreflexes in Long-Term Regulation of Renal Sympathetic Nerve Activity," Circulation Research, Jun. 27, 2003, © 2003 American Heart Association Inc., pp. 1282-1284.

Luff, S.E. et al., "Two types of sympathetic axon innervating the juxtaglomerular arterioles of the rabbit and rat kidney differ structurally from those supplying other arteries," May 1, 1991, Journal of Neurocytology 1991, vol. 20, © 1991 Chapman and Hall Ltd., pp. 781-795.

Lundborg, C. et al., "Clinical experience using intrathecal (IT) bupivacaine infusion in three patients with complex regional pain syndrome type I (CRPS-I)," Acta Aneaesthesiol. Scand. 1999, vol. 43, pp. 667-678.

Macarthur, Dr. Alison, "Spinal Anesthesia and Severe Gestational Hypertension," presentation at Mount Sinai Hospital, 25 pages.

Maeder, Micha, M.D. et al., "Contrast Nephropathy: Review Focusing on Prevention," Jun. 22, 2004, Journal of the American College of Cardiology Nov. 2, 2004, vol. 44, No. 9, © 2004 by the American College of Cardiology Foundation, pp. 1763-1771.

Malpas, Simon C., "What sets the long-term level of sympathetic nerve activity: is there a role for arterial baroreceptors?" Invited Review, Am J Physiol Regul. Integr. Comp. Physiol. 2004, vol. 286, © 2004 the American Physiological Society, pp. R1-R12.

Marenzi, Giancarlo, M.D. et al., "The Prevention of Radiocontrast-Agent-Induced Nephropathy by Hemofiltration," New England Journal of Medicine, Oct. 2, 2003, vol. 349 (14), © 2003 Massachusetts Medical Society, pp. 1333-1340.

Martin, Jason B. et al., "Gene Transfer to Intact Mesenteric Arteries by Electroporation," Mar. 27, 2000, Journal of Vascular Research 2000, vol. 37, 2000 S. Karger AG, Basel, pp. 372-380.

McCreery, Douglas B. et al., "Charge Density and Charge Per Phase as Cofactors in Neural Injury Induced by Electrical Stimulation," IEEE Transactions on Biomedical Engineering, vol. 17, No. 10, Oct. 1990, pp. 996-1000.

McCullough, Peter A., M.D., MPH et al., "Acute Renal Failure after Coronary Intervention: Incidence, Risk Factors and Relationship to Mortality," Apr. 14, 1997, Am J Med. 1997, vol. 103, 1997 Excerpta Medica, Inc., pp. 368-375.

McMurray, John J.V., M.D. and Eileen O'Meara, M.D., "Treatment of Heart Failure with Spironolactone-Trial and Tribulations," Aug. 5, 2004, New England Journal of Medicine, vol. 351, No. 6, © 2004 Massachusetts Medical Society, pp. 526-528.

McRobbie, D. and M.A. Foster, "Thresholds for biological effects of time-varying magnetic fields," Dec. 16, 1983, Clin. Phys. Physiol. Meas. 1984, vol. 5, No. 2, © 1984, The Institute of Physics, pp. 67-78.

Medtronic Neurostimulation Systems, "Expanding the Array of Pain Control Solutions," informational pamphlet, 1999 Medtronic, Inc., 6 pages.

Medtronic, "Spinal Cord Stimulation," Patient Management Guidelines for Clinicians, Medtronic, Inc. 1999, 115 pages.

Medtronic, "SynchroMed Infusion System—Clinical Reference Guide for Pain Therapy," Medtronic, Inc. 1998, 198 pages.

Mess, Sarah A., M.D. et al., "Implantable Baclofen Pump as an Adjuvent in Treatment of Pressure Sores," Mar. 1, 2003, Annals of Plastic Surgery, vol. 51, No. 5, Nov. 2003, © 2003 Lippincott Williams & Wilkins, pp. 465-467.

Mihran, Richard T. et al., "Temporally-Specific Modification of Myelinated Axon Excitability in Vitro Following A Single Ultrasound Pulse," Sep. 25, 1989, Ultrasound in Med.& Biol. 1990, vol. 16, No. 3, pp. 297-309.

Miklavcic, D. et al, "A Validated Model of in Vivo Electric Field Distribution in Tissues for Electrochemotherapy and for DNA Electrotransfer for Gene Therapy," Biochimica et Biophysica Acta, 1523, 2000, pp. 73-83, www.elsevier.com/locate/bba.

Mitchell, G.A.G., "The Nerve Supply of the Kidneys," Aug. 20, 1949, Acta Anatomica, vol. 10, Fasc. 1/2, 1950, pp. 1-37.

Moss, Nicholas G., "Renal function and renal afferent and efferent nerve activity," Am J Physiol 1982, vol. 243, © 1982, the American Physiological Society, pp. F425-F433.

Munglani, Rajesh, "The longer term effect of pulsed radiofrequency for neuropathic pain," Jun. 8, 1998, Pain, vol. 80, © 1999 International Association for the Study of Pain, Published by Elsevier Science B.V., pp. 437-439.

Naropin (ropivacaine HCI) injection, Rx only description, AstraZeneca 2001, 3 pages.

National High Blood Pressure Education Program, "1995 Update of the Working Group Reports on Chronic Renal Failure and Renovascular Hypertension," presentation, 13 pages.

National Kidney Foundation, "Are You At Increased Risk for Chronic Kidney Disease?" © 2002 National Kidney Foundation, Inc., 14 pages.

Nelson, Lawrence D. and Jeffrey L. Osborn, "Neurogenic Control of Renal Function in Response to Graded Nonhypotensive Hemorrahage in Conscious Dogs," Sep. 13, 1992, Am. J. Physiol. 264, 1993, American Physiological Society 1993, pp. R661-R667.

Nikolsky, Eugenia, M.D. et al., "Radiocontrast Nephropathy: Identifying the High-Risk Patient and the Implications of Exacerbating Renal Function," Rev Cardiovasc Med. 2003, vol. 4, Supp. 1, © 2003 MedReviews, LLC, pp. S7-S14.

Nozawa, Takashi et al., "Effects of Long Term Renal Sympathetic Denervation on Heart Failure After Myocardial Infarction in Rats," Sep. 22, 2001, Heart Vessels 2002, vol. 16, Springer-Verlag 2002, pp. 51-56.

Palmer, Biff F., M.D., "Managing Hyperkalemia Caused by Inhibitors of the Renin-Angiotensin-Aldosterone System," Aug. 5, 2004, The New England Journal of Medicine 2004, vol. 351, No. 6, © 2004 Massachusetts Medical Society, pp. 585-592.

Peacock, J.M. and R. Orchardson, "Action potential conduction block of nerves in vitro by potassium citrate, potassium tartrate and potassium oxalate," May 6, 1998, Journal of Clinical Periodontology, © 1999 Munksgaard, vol. 26, pp. 33-37.

Pettersson, A. et al., "Renal interaction between sympathetic activity and ANP in rats with chronic ischaemic heart failure," Nov. 25, 1998, Acta Physiol. Scand. 1989, vol. 135, pp. 487-492.

Pliquett, U., "Joule heating during solid tissue electroporation," Oct. 22, 2002, Medical & Biological Engineering and Computing 2003, vol. 41, pp. 215-219.

Podhajsky, R. J., et al. "The Histologic Effects of Pulsed and Continuous Radiofrequency Lesions at 42° C to Rat Dorsal Root Ganglion and Sciatic Nerve," Spine, vol. 30, No. 9, 2005, Lippincott Williams & Wilkins Inc., pp. 1008-1013.

Popovic, Jennifer .R. and Margaret J. Hall,"1999 National Hospital Discharge Survey," Advance Data, No. 319, CDC, pp. 1-17 & 20.

Practice Guidelines Writing Committee and ESH/ESC Hypertension Guidelines Committee, "Practice Guidelines for Primary Care Physicians: 2003 ESH/ESC Hypertension Guidelines," Published in Journal of Hypertension 2003, vol. 21, No. 10: 1011-1053, © 2003 European Society of Hypertension, pp. 1779-1786.

Pucihar, Gorazd et al., "The influence of medium conductivity on electropermeabilization and survival of cells in vitro," May 31, 2001, Bioelectrochemistry, vol. 54, 2001, Elsevier Science B.V. 2001, pp. 107-115.

Raji, A. R. M. And R. E. M. Bowden, "Effects of High-Peak Pulsed Electromagnetic Field on the Degeneration and Regeneration of the Common Peroneal Nerve in Rats," The Journal of Bone and Joint Surgery Aug. 1983, vol. 65-B, No. 4, © 1983 British Editorial Society of Bone and Joint Surgery, pp. 478-492.

Ram, C. Venkata S., M.D., "Understanding refractory hypertension," May 15, 2004, Patient Care May 2004, vol. 38, pp. 12-16, 7 pages from http://www.patientcareonline.com/patcare/content/printContentPopup.jsp?id=108324.

Ravalia, A. et al., "Tachyphylaxis and epidural anesthesia," Edgware General Hospital, Correspondence, p. 529.

Ribstein, Jean and Michael H. Humphreys, "Renal nerves and cation excretion after acute reduction in functioning renal mass in the rat," Sep. 22, 1983, Am J Physiol, vol. 246, © 1984 the American Physiological Society, pp. F260-F265.

Richebe, Philippe, M.D. et al., "Immediate Early Genes after Pulsed Radiofrequency Treatment: Neurobiology in Need of Clinical Trials," Oct. 13, 2004, Anesthesiology Jan. 2005, vol. 102, No. 1, © 2004 American Society of Anesthesiologists, Inc. Lippincott Williams & Wilkins, Inc., pp. 1-3.

Rihal, Charanjit S. et al., "Incidence and Prognostic Importance of Acute Renal Failure After Percutaneous Coronary Intervention," Mar. 6, 2002, Circulation May 14, 2002, vol. 10, © 2002 American Heart Association, Inc., pp. 2259-2264.

Rosen, S.M. et al., "Relationship of Vascular Reactivity to Plasma Renin Concentration in Patients with Terminal Renal Failure," Proc. Dialysis Transplant Forum 1974, pp. 45-47.

Roth, Bradley J. and Peter J. Basser, "A Model of the Stimulation of a Nerve Fiber by Electromagnetic Induction," IEEE Transactions on Biomedical Engineering, vol. 37, No. 6, Jun. 1990, pp. 588-597.

Rudin, Asa, M.D. et al., "Postoperative Epidural or Intravenous Analgesia after Major Abdominal or Thoraco-Abdominal Surgery," The Journal of the American Society of Anesthesiologists, Inc., Anesthesiology 2001, vol. 95, A-970, 1 page.

Rudnick, Michael R. et al., "Contrast-induced nephropathy: How it develops, how to prevent it," Cleveland Clinic Journal of Medicine Jan. 2006, vol. 73, No. 1, pp. 75-87.

Rump, L.C., "The Role of Sympathetic Nervous Activity in Chronic Renal Failure," J Clinical Basic Cardiology 2001, vol. 4, pp. 179-182.

Ruohonen, Jarmo et al., "Modeling Peripheral Nerve Stimulation Using Magnetic Fields," Journal of the Peripheral Nervous System 1997, vol. 2, No. 1, © 1997 Woodland Publications, pp. 17-29.

Scheiner, Avram, Ph.D., "The design, development and implementation of electrodes used for functional electrical stimulation," Thesis paper, Case Western Reserve University, May 1992, 220 pages.

Schoenbach, Karl H. et al., "Intracellular Effect of Ultrashort Electrical Pulses," Dec. 26, 2000, Bioelectromagnetics 2001, vol. 22, © 2001 Wiley-Liss Inc., pp. 440-448.

Schrier, Robert et al., "Cardiac and Renal Effects of Standard Versus Rigorous Blood Pressure Control in Autosomal-Dominant Polycystic Kidney Disease," Mar. 23, 2002, Journal of the American Society of Nephrology, © 2002 American Society of Nephrology, pp. 1733-1739.

Scremin, Oscar U., M.D., Ph.D. and Danel P. Holschneider, M.D., "31. & 32. An Implantable Bolus Infusion Pump for the Neurosciences," FRP, 04-05, 3 pages.

Shu-Qing, Liu et al., "Old spinal cord injury treated by pulsed electric stimulation," General Hospital of Beijing Command, Beijing, 5 pages (full article in Chinese; abstract on last page).

Shupak, Naomi M., "Therapeutic Uses of Pulsed Magnetic-Field Exposure: A Review," Radio Science Bulletin Dec. 2003, No. 307, pp. 9-32.

Simpson, B. et al, "Implantable Spinal Infusion Devices for Chronic Pain and Spasticity: An Accelerated Systematic Review," ASERNIP-S Report No. 42, May 2003, 56 pages.

Sisken, B.F. et al., "229.17 Influence of Non-Thermal Pulsed Radiofrequency Fields (PRF) on Neurite Outgrowth," Society for Neuroscience, vol. 21, 1995, 2 pages.

Skeie, B. et al., "Effect of chronic bupivacaine infusion on seizure threshold to bupivacaine," Dec. 28, 1986, Acta Anaesthesiol. Scand. 1987, vol. 31, pp. 423-425.

Skopec, M., "A Primer on Medical Device Interactions with Magnetic Resonance Imaging Systems," Feb. 4, 1997, CDRH Magnetic Resonance Working Group, U.S. Department of Health and Human Services, Food and Drug Administration, Center for Devices and Radiological Health, Updated May 23, 1997, 17 pages, http://www.fde.gov/cdrh/ode/primerf6.html, (last accessed Jan. 23, 2006.

Slappendel, Robert et al., "The efficacy of radiofrequency lesioning of the cervical spinal dorsal root ganglion in a double blinded randomized study," Jun. 26, 1997, Pain, vol. 73, © 1997 International Association of the Study of Pain, Elsevier Science B.V., pp. 159-163.

Sluijter, M.D., Ph.D., "Pulsed Radiofrequency," May 17, 2005, Anesthesiology Dec. 2005, vol. 103, No. 6, © 2005 American Society of Anesthesiologists, Inc. Lippincott Williams & Wilkins, Inc., pp. 1313-1314.

Sluijter, M.D., Ph.D., "Radiofrequency Part 1: The Lumbosacral Region," Chapter 1 Mechanisms of Chronic Pain and part of Chapter 2 Spinal Pain, © 2001 FlivoPress SA, Meggen (LU), Switzerland, pp. 1-26.

Sluijter, M.D., Ph.D., "Radiofrequency Part 2: Thoracic and Cervical Region, Headache and Facial Pain," various pages from, FlivoPress SA, Meggen (LU), Switzerland, 13 pages.

Sluijter, M.D., Ph.D., "The Role of Radiofrequency in Failed Back Surgery Patients," Current Review of Pain 2000, vol. 4, © 2000 by Current Science Inc., pp. 49-53.

Souza, D.R.B. et al., "Chronic experimental myocardial infarction produces antinatriuresis by a renal nerve-dependent mechanism," Oct. 14, 2003, Brazilian Journal of Medical and Biological Research 2004, vol. 37, pp. 285-293.

Standl, Thomas, M.D., et al, "Patient-controlled epidural analgesia reduces analgesic requirements compared to continuous epidural infusion after major abdominal surgery," Aug. 29, 2002, Canada Journal of Anesthesia 2003, vol. 50, No. 3, pp. 258-264.

Stone, Gregg W., M.D. et al., "Fenoldopam Mesylate for the Prevention of Contrast-Induced Nephropathy," JAMA Nov. 5, 2003, vol. 290, No. 17, © 2003 American Medical Association, pp. 2284-2291.

Sung, Duk Hyun, M.D. et al., "Phenol Block of Peripheral Nerve Conduction: Titrating for Optimum Effect," Jun. 27, 2000, Arch. Phys. Med. Rehabil., vol. 82, May 2001, pp. 671-676.

Taler, Sandra J. et al., "Resistant Hypertension, Comparing Hemodynamic Management to Specialist Care," Mar. 12, 2002, Hypertension 2002, vol. 39, 2002 American Heart Association, Inc., pp. 982-988.

Tay, Victoria Km et al., "Computed tomography fluoroscopy-guided chemical lumbar sympathectomy: Simple, safe and effective," Oct. 31, 2001, Diagnositc Radiology, Australasian Radiolology, 2002, vol. 46, pp. 163-166.

Thompson, Gregory W. et al, "Bradycardia Induced by Intravascular Versus Direct Stimulation of the Vagus Nerve," Aug. 24, 1997, The Society of Thoracic Surgeons 1998, pp. 637-642.

Thrasher, Terry N., "Unloading arterial baroreceptors causes neurogenic hypertension," Dec. 4, 2001, Am J Physiol Regulatory Integrative Comp. Physiol., vol. 282, © 2002 the American Physiological Society, pp. R1044-R1053.

Tokuno, Hajime A. et al., "Local anesthetic effects of cocaethylene and isopropylcocaine on rat peripheral nerves," Oct. 7, 2003, Brain Research 996, 2004, © 2003 Elsevier B.V., pp. 159-167.

Trapani, Angelo J. et al., "Neurohumoral interactions in conscious dehydrated rabbit," Am J Physiol 1988, vol. 254, © 1988 the American Physiological Society, pp. R338-R347.

Trock, David H. et al., "The Effect of Pulsed Electromagnetic Fields in the Treatment of Osteoarthritis of the Knee and Cervical Spine. Report of Randomized, Double Blind, Placebo Controlled Trials," Mar. 22, 1994, The Journal of Rheumatology 1994, vol. 21, pp. 1903-1911.

Troiano, Gregory C. et al., "The Reduction in Electroporation Voltages by the Addition of a Surfactant to Planar Lipid Bilayers," May 12, 1998, Biophysical Journal, vol. 75, Aug. 1998, © the Biophysical Society, pp. 880-888.

Trumble, Dennis R., and James A. Magovern, "Comparison of Dog and Pig Models for Testing Substernal Cardiac Compression Devices," Nov. 2003, ASAIO Journal 2004, pp. 188-192.

Tsai, E., "Intrathecal drug delivery for pain indications, technique, results," Pain Lecture presentation, Jun. 8, 2001, 31 pages.

Uematsu, Toshihiko, M.D., Ph.D., F.I.C.A. et al., "Extrinsic Innervation of the Canine Superior Vena Cava, Pulmonary, Portal and Renal Veins," Angiology—Journal of Vascular Diseases, Aug. 1984, pp. 486-493.

United States Renal Data System, "USRDS 2003 Annual Data Report: Atlas of End-Stage Renal Disease in the United States," National Institutes of Health, National Institute of Diabetes and Digestive and Kidney Diseases, 2003, 593 pages.

Upadhyay, Pramod, "Electroporation of the skin to deliver antigen by using a piezo ceramic gas igniter," Jan. 27, 2001, International Journal of Pharmaceutics, vol. 217, © 2001 Elsevier Science B.V., pp. 249-253.

Valente, John F. et al., "Laparoscopic renal denervation for intractable ADPKD-related pain," Aug. 24, 2000, Nephrology Dialysis Transplantation 2001, vol. 16, European Renal Association—European Dialysis and Transplant Association, p. 160.

Van Antwerp, Bill and Poonam Gulati., "Protein Delivery from Mechanical Devices Challenges and Opportunities," Medtronic Presentation, 19 pages.

Velazquez, Eric J., "An international perspective on heart failure and left ventricular systolic dysfunction complicating myocardial infarction: the VALIANT registry," Aug. 5, 2004, European Heart Journal, vol. 25, © 2004 Elsevier Ltd., pp. 1911-1919.

Velez-Roa, Sonia, M.D., et al., "Peripheral Sympathetic Control During Dobutamine Infusion: Effects of Aging and Heart Failure," Jul. 7, 2003, Journal of the American College of Cardiology 2003, vol. 42, No. 9, © 2003 American College of Cardiology Foundation, pp. 1605-1610.

Vigilance, Deon W. et al., "A Novel Approach to Increase Total Urine Output in Acute Heart Failure: Unilateral Renal nerve Blockade," RNB Abstract AHA, 2 pages.

Villarreal, Daniel et al., "Effects of renal denervation on postprandial sodium excretion in experimental heart failure," Oct. 29, 1993, Am J Physiol 266, 1994, pp. R1599-R1604.

Villarreal, Daniel et al., "Neurohumoral modulators and sodium balance in experimental heart failure," Nov. 6, 1992, Am J Physiol, vol. 264, 1993, pp. H1187-H1193.

Wagner, C.D. et al, "Very low frequency oscillations in arterial blood pressure after autonomic blockade in conscious dogs," Feb. 5, 1997, Am J Physiol Regul Integr Comp Physiol 1997, vol. 272, © 1997 the American Physiological Society, pp. 2034-2039.

Wald, Jan D. Ph.D. et al., "Cardiology Update 2003," Sep. 11, 2003, © 2003 AG Edwards, 120 pages.

Wang, Xi et al., "Alterations of adenylyl cyclase and G proteins in aortocaval shut-induced heart failure," Jul. 2004, Am J Physiol Heart Circ Physiol., vol. 287, © 2004 the American Physiological Society, pp. H118-H125.

Weaver, James C., "Chapter 1: Electroporation Theory, Concepts and Mechanisms," Methods in Molecular Biology, vol. 55, Plant Cell Electroporation and Electrofusion Protocols, Edited by J.A. Nickoloff, © Humana Press Inc., pp. 3-28.

Weaver, James C., "Electroporation: A General Phenomenon for Manipulating Cells and Tissues," Oct. 22, 1992, Journal of Cellular Biochemistry, vol. 51, © 1993 Wiley-Liss, Inc., pp. 426-435.

Weiner, Richard L., M.D., "Peripheral nerve neurostimulation," Neurosurgery Clinics of North America 2003, vol. 14, © 2003 Elsevier Inc., pp. 401-408.

Weisbord, Steven D., M.D. and Paul M. Palevsky, M.D., "Radiocontrast-Induced Acute Renal Failure," Jul. 10, 2004, Journal of Intensive Care Medicine 2005, vol. 20 (2), © 2005 Sage Publications, pp. 63-75.

Wilson, D.H. et al., "The Effects of Pulsed Electromagnetic Energy on Peripheral Nerve Regeneration," Annals New York Academy of Sciences, pp. 575-585.

Wolinsky, Harvey, M.D., Ph.D. and Swan N. Thung, M.D., "Use of a Perforated Balloon Catheter to Deliver Concentrated Heparin Into the Wall of the Normal Canine Artery," Aug. 30, 1989, JACC 1990, vol. 15, © 1990 The American College of Cardiology, pp. 475-481.

Wyss, J.Michael et al., "Neuronal control of the kidney: Contribution to hypertension," Apr. 8, 1991, Can. J. Physiol. Pharmacol., vol. 70, 1992, pp. 759-770.

Yamaguchi, Jun-ichi et al., "Prognostic Significance of Serum Creatinine Concentration for In-Hospital Mortality in Patients With Acute Myocardial Infarction Who Underwent Successful Primary Percutaneous Coronary Intervention (from the Heart Institute of Japan Acute Myocardial Infarction [HIJAMI] Registry)," Feb. 24, 2004, The American Journal of Cardiology, vol. 93, Jun. 15, 2004, © 2004 by Excerpta Medica, Inc., pp. 1526-1528.

Ye, Richard D., M.D., Ph.D., "Pharmacology of the Peripheral Nervous System," E-425 MSB, 6 pages.

Ye, Shaohua et al., "Renal Injury Caused by Intrarenal Injection of Phenol Increases Afferent and Efferent Renal Sympathetic Nerve Activity," Mar. 12, 2002, American Journal of Hypertension Aug. 2002, vol. 15, No. 8, © 2002 the American Journal of Hypertension, Ltd. Published by Elsevier Science Inc., pp. 717-724.

Yong-Quan, Dong et al., "The therapeutic effect of pulsed electric field on experimental spinal cord injury," Beijing Army General Hospital of People's Liberation Army, Beijing, 5 (full article in Chinese; abstract on last page).

Young, James B., M.D., FACC, "Management of Chronic Heart Failure: What Do Recent Clinical Trials Teach Us?" Reviews in Cardiovascular Medicine 2004, vol. 5, Suppl. 1, © 2004 MedReviews, LLC, pp. S3-S9.

Zanchetti, A. et al., "Neural Control of the Kidney—Are There Reno-Renal Reflexes?" Clin. and Exper. Hyper. Theory and Practice, A6 (1&2), © 1984 Marcel Dekker Inc., pp. 275-286.

Zimmermann, Ulrich, "Electrical Breakdown, Electropermeabilization and Electrofusion," Rev. Physiol. Biochem. Pharmacol., vol. 105, © Springer-Verlag 1986, pp. 175-256.

Zucker, Irving H. et al., "The origin of sympathetic outflow in heart failure: the roles of angiotensin II and nitric oxide," Progress in Biophysics & Molecular Biology 2004, vol. 84, © 2003 Elsevier Ltd., pp. 217-232.

Zundert, Jan Van, M.D. Fipp and Alex Cahana, M.D. DAAPM, "Pulsed Radiofrequency in Chronic Pain Management: Looking for the Best Use of Electrical Current," Pain Practice 2005, vol. 5, Issue 2, © 2005 World Institute of Pain, pp. 74-76.

Cameron, Tracy. "Micromodular Implants to Provide Electrical Stimulation of Paralyzed Muslces and Limbs." IEEE Transactions on Biomedical Engineering, vol. 44, No. 9, Sep. 1997. pp. 781-790.

Guimaraes, Sarfim. "Vascular Adrenoceptors: An Update" pp. 319-356.

Hammer, Leah W. "Differential Inhibition of Functional Dilation of Small Arterioles by Indomethacin and Glibenclamide." Hypertension. Feb. 2001, Part II. pp. 599-603.

Hortobagyi, Gabriel N. "Randomized Trial of High-Dose Chemotherapy and Blood Cell Autografts for High-Risk Primary Breast Carcinoma" Journal of the National Cancer Institute, vol. 92, No. 3, Feb. 2, 2000 pp. 225-233.

Janda, J., "Impact of the electrical stimulation apparatus rebox on the course of ischemic renal damage in rats," British Library-"The world's knowledge" pp. 252-254 (translated and untranslated versions).

U.S. Appl. No. 60/236,420, Harrison et al.
U.S. Appl. No. 60/370,190.
U.S. Appl. No. 60/408,665.
U.S. Appl. No. 60/415,575.
U.S. Appl. No. 60/442,970.

"Atrial Fibrillation" Heart and Vascular Health on Yahoo! Health. 2 pages. <URL: http://health.yahoo.com/topic/heart/overview/article/healthwise/hw160872;_yit=AiBT43Ey74HQ 7ft3jAb4C.sPu7cF>.

"Heart Arrhythmia" Heart and Vascular Health on Yahoo! Health. 13 pages. <URL: http://health.yahoo.com/topic/heart/overview/article/mayoclinic/21BBE2B0-128D-4AA2-A5CE215065586678;_ylt= Aqd9M5rNyHD0sbPOmHXFhLcPu7cF>.

"Isovue: Data Sheet", Regional Health Limited. 8 pages. Mar. 11, 2003.

"Micro ETS Hyperhidrosis USA" Hyperhidrosis USA. 2 pages. <URL: http://www.hyperhidrosis-usa.com/Index.html>.

Amersham Health. "Hypaque-Cysto" 6 pages. 2003.

Arentz, Thomas et al. "Incidence of pulmonary vein stenosis 2 years after radiofrequency catheter ablation of refractory atrial fibrillation." European Heart Journal. 2003. 24; pp. 963-969.

Boehmer, John P. "Resynchronization Therapy for Chronic CHF: Indications, Devices and Outcomes". Penn State College of Medicine: Penn State Heart and Vascular Institute. Transcatheter Cardiovascular Therapeutics 2005. 31 slides.

Bourge, Robert C. "Heart Failure Monitoring Devices: Rationale and Status" 28 pages.

Bunch, Jared T. et al. "Mechanisms of Phrenic Nerve Injury During Radiofrequency Ablation at the Pulmonary Vein Orifice." Journal of Cardiovascular Electrophysiology. vol. 16, No. 12. pp. 1318-1325. Dec. 2005.

Burkhoff, Daniel. "Interventional Device-Based Therapy for CHF Will Redefine Current Treatment Paradigms". Columbia University. 2004. 32 slides.

Canbaz, Suat et al. "Electrophysiological evaluation of phrenic nerve injury during cardiac surgery—a prospective, controlled clinical study." BioMed Central. 5 pages. 2004.

Carson, Peter. "Device-based Treatment for Chronic Heart Failure: Electrical Modulation of Myocardial Contractility". Transcatheter Cardiovascular Therapeutics 2005. 21 slides.

Chiou, CW et al. "Efferent Vagal Innervation of the Canine Atria and Sinus and Atrioventricular Nodes". Circulation. Jun. 1997. 95(11):2573-2584. Abstract only. 2 pages.

Cryovascular Systems, Inc. "Pre-Clinical Testing Establishing Parameters". PowerPoint Presentation. 18 slides.

Daniel, Alan and Honig, Carl R. "Does Histamine Influence Vasodilation Caused by Prolonged Arterial Occlusion or Heavy Exercise?" The Journal of Pharmacology and Experimental Therapeutics. vol. 215 No. 2. Aug. 21, 1980. pp. 533-538.

Dong, Jun et al. "Incidence and Predictors of Pulmonary Vein Stenosis Following Catheter Ablation of Atrial Fibrillation Using the Anatomic Pulmonary Vein Ablation Approach: Results from Paired Magnetic Resonance Imaging." Journal of Cardiovascular Electrophysiology. vol. 16 No. 8, Aug. 2005, pp. 845-852.

Fava, M. "Clinical Testing Establishing Safety & Efficacy". PowerPoint Presentation. Cryovascular Systems, Inc. 14 slides.

Fava, M. et al. "Initial Human Experience with CryoPlasty™ in the Treatment of Infrainguinal Arterial Disease." Abstract. 1 page.

Fischell, Tim A. et al. "Ultrasonic Energy: Effects on Vascular Function and Integrity." Circulation: Journal of the American Heart Association. 1991. 84;pp. 1783-1795.

Hodgkin, Douglas D. et al. "Electrophysiologic Characteristics of a Pulsed Iontophoretic Drug-Delivery System in Coronary Arteries." Journal of Cardiovascular Pharmacology. 29(1):pp. 39-44, Jan. 1997. Abstract. 2 pages.

International Search Report, PCT/US04/38498, Mailed Feb. 18, 2005, Applicant: G & L Consulting, LLC (3 pages).

Jia, Jianping and Pollock, Martin. "The pathogenesis of non-freezing cold nerve injury: Observations in the rat." Brain. 120; pp. 631-646. 1997.

Jian, Jianping et al. "Cold injury to nerves is not due to ischaemia alone." Brain. 121; pp. 989-1001. 1998.

Jin, Yuanzhe. et al. "Pulmonary Vein Stenosis and Remodeling After Electrical Isolation for Treatment of Atrial Fibrillation: Short- and Medium-Term Follow-Up." PACE, vol. 27, pp. 1362-1370. Oct. 2004.

Joye, James D. and Tatsutani, Kristine. "In Vitro Studies of Arterial Freezing Injury". 4 pages.

Joye, James D. and Tatsutani, Kristine. "In Vivo Study of Endovascular Cryotherapy for the Prevention of Restenosis." 4 pages.

Knot, Harm J. and Nelson, Mark T. "Regulation of arterial diameter and wall [Ca2+] in cerebral arteries of rat by membrane potential and intravascular pressure." The Journal of Physiology. 1998. 508; pp. 199-209.

Kok, Lai Chow et al. "Effect of Heating on Pulmonary Veins: How to Avoid Pulmonary Vein Stenosis." Journal of Cardiovascular Electrophysiology. vol. 14, No. 3, Mar. 2003. pp. 250-254.

Kumagai, K. et al. "New Approach to Pulmonary Vein Isolation for Atrial Fibrillation Using a Multielectrode Basket Catheter". Circulation Journal. vol. 70, No. 1. Jan. 2006. Abstract only. 2 pages.
Lee, Michael A. (editor). SPORTSMed. Connecticut State Medical Society Committee on the Medical Aspects of Sports. Fall/Winter 2005. 10 pages.
Mathur, Vandana S. "Intra-Renal Drug Delivery for Fluid Overload". FlowMedica. Transcatheter Cardiovascular Therapeutics 2005. 31 slides.
Mehran, Roxana. "Renal insufficiency and contrast nephropathy: The most common, least understood risk factor". Cardiovascular Research Foundation. Columbia University Medical Center. 2005. 86 slides.
Packer, Douglas L. et al. "Clinical Presentation, Investigation, and Management of Pulmonary Vein Stenosis Complicating Ablation for Atrial Fibrillation." Circulation: Journal of the American Heart Association. Feb. 8, 2005. pp. 546-554.
Pappone, Carlo and Santinelli, Vincenzo. "[2005][P2-70] Safety Report of Circumferential Pulmonary Vein Ablation. A 9-Year Single-Center Experience on 6,442 Patients with Atrial Fibrillation." Abstract only. 1 page.
Pappone, Carlo et al, "[2004][759] Pulmonary Vein Denervation Benefits Paroxysmal Atrial Fibrillation Patients after Circumferential Ablation." Abstract only. 1 page.
Purerfellner, Helmut and Martinek, Martin. "Pulmonary vein stenosis following catheter ablation of atrial fibrillation." Current Opinion in Cardiology. 20; pp. 484-490. 2005.
Purerfellner, Helmut et al. "Pulmonary Vein Stenosis by Ostial Irrigated-Tip Ablation: Incidence, Time Course, and Prediction." Journal of Cardiovascular Electrophysiology. vol. 14, No. 2, Feb. 2003. pp. 158-164.
Saad, Eduardo B. et al. "Pulmonary Vein Stenosis After Radiofrequency Ablation of Atrial Fibrillation: Functional Characterization, Evolution, and Influence of the Ablation Strategy." Circulation. 108; pp. 3102-3107. 2003.
Sabbah, Hani N. "Animal Models for Heart Failure and Device Development". Henry Ford Health System. 24 slides.
Schauerte, P et al. "Catheter ablation of cardiac autonomic nerves for prevention of vagal atrial fibrillation." Circulation. 102(22). Nov. 28, 2000. Abstract only. 2 pages.
Schauerte, P et al. "Focal atrial fibrillation: experimental evidence for a pathophysiologic role of the autonomic nervous system." Journal of Cardiovascular Electrophysiology. 12(5). May 2001. Abstract only. 2 pages.
Schauerte, P et al. "Transvenous parasympathetic nerve stimulation in the inferior vena cava and atrioventricular conduction." Journal of Cardiovascular Electrophysiology. 11(1). Jan. 2000. Abstract only. 2 pages.
Scherlag, BJ and Po, S. "The intrinsic cardiac nervous system and atrial fibrillation." Current Opinion in Cardiology. 21(1):51-54, Jan. 2006. Abstract only. 2 pages.
Schmitt, Joseph et al. "Intravascular Optical Coherence Tomography—Opening a Window into Coronary Artery Disease". LightLab Imaging, Inc. Business Briefing: European Cardiology 2005.
Serrador, Jorge M. "Autonomic Regulation of the Cardiovascular System". MIT Lecture. 8 pages, 48 slides.
Siegel, RJ et al. "Clinical demonstration that catheter-delivered ultrasound energy reverses arterial vasoconstriction." Journal of the American College of Cardiology. 1992. 20; 732-735. Summary only. 2 pages.
Sobotka, Paul A. "Treatment Strategies for Fluid Overload, CHF Patients". CHF Solutions. Transcatheter Cardiovascular Therapeutics 2005. 20 slides.
Steffen, W. et al. "Catheter-delivered high intensity, low frequency ultrasound induces vasodilation in vivo." European Heart Journal. 1994. 15;pp. 369-376.
Steg, PG et al. "Pulsed ultraviolet laser irradiation produces endothelium-independent relaxation of vascular smooth muscle". Circulation: Journal of the American Heart Association. 1989. pp. 189-197.
Taka, Tomomi et al. "Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats", Pathophysiology of Haemostasis and Thrombosis. Dec. 23, 2002. pp. 184-189.
Tamborero, David et al. "Incidence of Pulmonary Vein Stenosis in Patients Submitted to Atrial Fibrillation Ablation: A Comparison of the Selective Segmental Ostial Ablation vs. the Circumferential Pulmonary Veins Ablation." Journal of Intervocational Cardiac Electrophysiology. 14;pp. 41-25. 2005.
Terashima, Mitsuyasu et al. "Feasibility and Safety of a Novel CryoPlasty™ System". Poster. 1 page.
Thomas, John R. and Oakley, E. Howard N. "Chapter 15: Nonfreezing Cold Injury" *Medical Aspects of Harsh Environments*, vol. 1. pp. 467-490.
Vince, D. Geoffrey. "Virtual Histology: A new technique for the assessment of plaque composition". The Cleveland Clinic Foundation. 28 pages.
Yu, Wen-Chung et al. "Acquired Pulmonary Vein Stenosis after Radiofrequency Catheter Ablation of Paroxysmal Atrial Fibrillation." Journal of Cardiovascular Electrophysiology. vol. 12, No. 8. Aug. 2001. pp. 887-892.
U.S. Appl. No. 12/910,631, filed Oct. 22, 2010, Wu et al.
U.S. Appl. No. 12/940,922, filed Nov. 5, 2010, Gelfand et al.
U.S. Appl. No. 13/007,370, filed Jan. 18, 2011, Gelfand et al.
U.S. Appl. No. 12/996,897, filed Dec. 13, 2010, Demarais.
U.S. Appl. No. 13/009,748, filed Jan. 19, 2011, Beetel et al.
European Search Report; European Patent Application No. 07868755.5; Applicant: Ardian, Inc.; Date of Mailing: Jul. 28, 2010, 7 pages.
U.S. Appl. No. 12/759,641, filed Apr. 13, 2010, Clark et al.
U.S. Appl. No. 61/296,417, filed Jan. 19, 2010, Beetel et al.
U.S. Appl. No. 61/307,633, filed Feb. 24, 2010, Sobotka et al.
U.S. Appl. No. 61/258,824, filed Nov. 6, 2009, Gelfand et al.
U.S. Appl. No. 61/328,105, filed Apr. 26, 2010, Wu et al.
U.S. Appl. No. 12/790,639, filed May 28, 2010, Wu et al.
U.S. Appl. No. 12/871,457, filed Apr. 30, 2010, Wu et al.
U.S. Appl. No. 61/371,110, filed Aug. 5, 2010, Gelfand et al.
European Search Report; European Patent Application No. 05806045.0; Applicant: Ardian, Inc.; Date of Mailing: Sep. 22, 2009, 8 pages.
European Search Report; European Patent Application No. 05811851.4; Applicant: Ardian, Inc.; Date of Mailing: Oct. 1, 2009, 7 pages.
European Search Report; European Patent Application No. 06847926.0; Applicant: Ardian, Inc.; Date of Mailing: Feb. 10, 2010, 6 pages.
European Search Report; European Patent Application No. 0775925.8; Applicant: Ardian, Inc.; Date of Mailing: Apr. 29, 2010, 9 pages.
European Search Report; European Patent Application No. 07799148.7; Applicant: Ardian, Inc.; Date of Mailing: Jul. 23, 2009, 6 pages.
European Examination Report; European Patent Application No. 07799148.7; Applicant: Ardian, Inc.; Date of Mailing: Jan. 19, 2010, 4 pages.
European Search Report; European Patent Application No. 09156661.2; Applicant: Ardian, Inc.; Date of Mailing: Jul. 23, 2009, 6 pages.
European Examination Report; European Patent Application No. 09156661.2; Applicant: Ardian, Inc.; Date of Mailing: Jan. 19, 2010, 6 pages.
European Search Report; European Patent Application No. 09167937.3; Applicant: Ardian, Inc.; Date of Mailing: Nov. 11, 2009, 6 pages.
European Search Report; European Patent Application No. 09168202.1; Applicant: Ardian, Inc.; Date of Mailing: Nov. 11, 2009, 5 pages.
European Search Report; European Patent Application No. 09168204.7; Applicant: Ardian, Inc.; Date of Mailing: Nov. 19, 2009, 6 pages.
*Ex parte Quayle* Office Action; U.S. Appl. No. 11/144,173; Mailed on May 28, 2009, 4 pages.
Final Office Action; U.S. Appl. No. 11/266,993; Mailed on Jan. 8, 2010, 7 pages.

Final Office Action; U.S. Appl. No. 11/363,867; Mailed on May 1, 2009, 8 pages.
Final Office Action; U.S. Appl. No. 11/599,723; Mailed on Apr. 5, 2010, 17 pages.
Final Office Action; U.S. Appl. No. 11/599,890; Mailed on Apr. 29, 2009, 9 pages.
International Search Report and Written Opinion for PCT/US2009/069334; Applicant: Ardian, Inc.; Mailing Date: Mar. 1, 2010, 10 pages.
Koomans, H.A., et al., "Sympathetic hyperactivity in chronic renal failure: a wake-up call." J Am Soc Nephrol. 2004;15:524-37.
Non-Final Office Action; U.S. Appl. No. 11/144,298; Mailed Oct. 29, 2009, 8 pages.
Non-Final Office Action; U.S. Appl. No. 11/189,563; Mailed on May 28, 2009, 5 pages.
Non-Final Office Action; U.S. Appl. No. 11/252,462; Mailed on Feb. 22, 2010, 6 pages.
Non-Final Office Action; U.S. Appl. No. 11/266,993; Mailed on Jul. 8, 2009, 6 pages.
Non-Final Office Action; U.S. Appl. No. 11/368,553; Mailed on Oct. 7, 2009, 5 pages.
Non-Final Office Action; U.S. Appl. No. 11/368,553; Mailed on May 18, 2010, 4 pages.
Non-Final Office Action; U.S. Appl. No. 11/368,809; Mailed on Dec. 3, 2009, 4 pages.
Non-Final Office Action; U.S. Appl. No. 11/368,949; Mailed on Jun. 11, 2010, 6 pages.
Non-Final Office Action; U.S. Appl. No. 11/368,971; Mailed on Aug. 24, 2010, 9 pages.
Non-Final Office Action; U.S. Appl. No. 11/451,728; Mailed on Jul. 2, 2009, 5 pages.
Non-Final Office Action; U.S. Appl. No. 11/451,728; Mailed on Dec. 28, 2009, 7 pages.
Non-Final Office Action; U.S. Appl. No. 11/504,117; Mailed on Mar. 31, 2009, 10 pages.
Non-Final Office Action; U.S. Appl. No. 11/599,649; Mailed on Mar. 30, 2009, 10 pages.
Non-Final Office Action; U.S. Appl. No. 11/599,723; Mailed on Jun. 26, 2009, 17 pages.
Non-Final Office Action; U.S. Appl. No. 11/599,882; Mailed on Jul. 6, 2009, 13 pages.
Non-Final Office Action; U.S. Appl. No. 11/688,178; Mailed on Jun. 28, 2010, 5 pages.
Non-Final Office Action; U.S. Appl. No. 11/840,142; Mailed on Apr. 3, 2009, 13 pages.
Non-Final Office Action; U.S. Appl. No. 12/567,521; Mailed on Sep. 3, 2010, 9 pages.
Non-Final Office Action; U.S. Appl. No. 12/616,708; Mailed Sep. 16, 2010, 10 pages.
Thatipelli et al., CT Angiography of Renal Artery Anatomy for Evaluating Embolic Protection Devices, Journal of Vascular and Interventional Radiology, Jul. 2007, pp. 842-846.
Allen, E.V., "Sympathectomy for essential hypertension," Circulation, 1952, 6:131-140.
Chen, S.A. et al., "Initiation of atrial fibrillation by ectopic beats originating from the pulmonary veins: electrophysiological characteristics, pharmacological responses, and effects of radiofrequency ablataion," Circulation, 1999, 100:1879-1886.
European Search Report; European Patent Application No. 07798341.9; Applicant: Ardian, Inc.; Date of Mailing Aug. 4, 2011; 6 pages.
Gottschalk, C.W., "Renal nerves and sodium excretion," Ann. Rev. Physiol., 1979, 41:229-240.
Haissaguerre, M. et al., "Spontaneous initiation of atrial fibrillation by ectopic beats orginating in the pulmonary veins," New England Journal of Medicine, 1998, 339: 659-666.
Heuer, G.J., "The surgical treatment of essential hypertension," Annals of Surgery, 1936; 104 (4): 771-786.
Mancia, G., Grassi, G., Giannattasio, C., Seravalle, G., "Sympathetic activration of pathogenesis of hypertension and progression of organ damage," Hypertension 1999, 34 (4 Pt 2): 724-728.
Non-Final Office Action; U.S. Appl. No. 12/725,375; Mailed on Oct. 12, 2010, 14 pages.

Non-Final Office Action; U.S. Appl. No. 11/599,723; Mailed on Oct. 15, 2010, 16 pages.
Shah, D.C., Haissaguerre, M., Jais, P., "Catheter ablation of pulmonary vein foci for atrial fibrillation: pulmonary vein foci ablation for atrial firbrillation," Thorac Cardiovasc Surg, 1999, 47 (suppl. 3): 352-356.
Smithwick, R.H., "Surgical treatment of hypertension," Am J Med 1948, 4:744-759.
Whitelaw, G.P., Kinsey, D., Smithwick, R.H., "Factors influencing the choice of treatment in essential hypertension: surgical, medical, or a combination of both," Am J Surg, 1964, 107:220-231.
Page, I.H., "Effect on renal efficiency of lowering BP in cases of essential hypertension and nephritis," J Clin Invest., 1934; 13:909-915.
Bello-Reuss, E. et al., "Actue unilateral renal denervation in rats with extracellular volume expansion," Departments of Medicine and Physiology, Univeristy of North Carolina School of Medicine. F26-F32, Jul. 1975.
"Advanced Neuromodulation Systems' Comparison Chart," 1 page, Dec. 16, 2008.
"Atrial Fibrillation" Heart and Vascular Health on Yahoo! Health. 2 pages. <URL:http://health.yahoo.com/topic/heart/overview/article/healthwise/hw160872;_ylt=AiBT43Ey74HQ7ft3jAb4C.sPu7cF> Feb. 21, 2006.
"Cardiac Glycosides," Heart Disease—A Textbook of Cardiovascular Medicine vol. 2, Edited by Eugene Braunwald, 5th edition, WB Saunders Company, pp. 480-481, 1997.
"Clinical Trials in Hypertension and Renal Diseases," Slide Source, www.hypertensiononline.org, 33 pages Aug. 13, 2001.
"Effects of Renal Failure on the Cardiovascular System," 5th Edition Heart Disease, A Textbook of Cardiovascular Medicine, vol. 2, Edited by Eugene Braunwald, W.B. Saunders Company, pp. 1923-1925 1997.
"Epidemiology of Renal Disease in Hypertension," slide presentation by hypertensiononline.org, 21 pages Mar. 30, 2001.
"Heart Arrhythmia" Heart and Vascular Health on Yahoo! Health. 13 pages. <URL:http://health.yahoo.com/topic/heart/overview/article/mayoclinic/21BBE2B0-128D-4AA2-A5CE215065586678;_ylt=Aqd9M5rNyHD0sbPOmHXFhLcPu7cF> Feb. 16, 2005.
"Hypertension and Renal Disease: Mechanisms," Slide Show by www.hypertensiononline.org, 22 pages Mar. 30, 2001.
"Implantable Neurostimulation Systems," Medtronic Neurological, http://medtronic.com/neuro/paintherapies/pain_treatment_ladder/pdf/implantable_brochure.pdf Jan. 18, 1999.
"Introduction to Autonomic Pharacology," Chapter 3, Part 2 Autonomic Pharmacology, pp. 18-26, May 24, 2002.
"Renal Parenchymal Disease," Ch. 26, 5th Edition Heart Disease, A Textbook of Cardiovascular Medicine vol. 2, Edited by Eugene Braunwald, WB Saunders Company, pp. 824-825 1997.
Bourge, R.C., "Heart Failure Monitoring Devices: Rationale and Status" 28 pages, Feb. 2001.
Dibona, Gerald F., "Peripheral and Central Interactions between the Renin-Angiotensin System and the Renal Sympathetic Nerves in Control of Renal Function," Annals New York Academy of Sciences, pp. 395-406 Jan. 25, 2006.
Dibona, Gerald F. and Ulla C. Kopp, "Role of the Renal Sympathetic Nerves in Pathophysiological States," Neural Control of Renal Function, vol. 77, pp. 142-197, Jan. 1997.
Gattone II, Vincent H. et al., "Contribution of Renal Innervation to Hypertension in Polycystic Kidney Disease in the Rat," University of Chicago Section of Urology, 16 pages, Mar. 17, 2008.
Guimaraes, Sarfim. "Vascular Adrenoceptors: An Update." pp. 319-356, Jun. 1, 2001.
Janda, J., "Impact of the electrical stimulation apparatus rebox on the course of ischemic renal damage in rats," British Library—"The World's knowledge" pp. 252-254 (translated and untranslated versions) 1996.
Lee, Raphael C. et al., "Clinical Sequelae Manifested in Electrical Shock Survivors," Presentation by the Electrical Trauma Research Program, The University of Chicago, 37 pages Dec. 24, 2004.

Pappone, Carlo et al., "[2005][P2-70] Safety Report of Circumferential Pulmonary Vein Ablation. A 9-Year Single-Center Experience on 6,442 Patients with Atrial Fibrillation," Abstract only. 1 page, May 2005.
Pappone, Carlo et al., "[2004][759] Pulmonary Vein Denervation Benefits Paroxysmal Atrial Fibrillation Patients after Circumferential Ablation," Abstract only. 1 page, Jan. 5, 2004.
Ravalia, A. et al., "Tachyphylaxis and epidural anaesthesia," Edgware General Hospital, Correspondence, p. 529, Jun. 1989.
Sabbah, Hani N., "Animal Models for Heart Failure and Device Development," Henry Ford Health System, 24 slides, Oct. 17, 2005.
Scremin, Oscar U., M.D., Ph.D. and Daniel P. Holschneider, M.D., "31 & 32.. An Implantable Bolus Infusion Pump for the Neurosciences," FRP, 04-05, 3 pages, Apr. 2005.
Shu-Qing, Liu et al., "Old spinal cord injury treated by pulsed electric stimulation," General Hospital of Beijing Command, Beijing, 5 pages (full article in Chinese; abstract on last page) Dec. 6, 1990.
Sluijter, M.D., Ph.D., "Radiofrequency Part 2: Thoracic and Cervical Region, Headache and Facial Pain," various pages from, FlivoPress SA, Meggen (LU), Switzerland, 13 pages 2002.
Terashima, Mitsuyasu et al. "Feasibility and Safety of a Novel CryoPlasty™ System". Poster. 1 page, Mar. 15, 2002.
Thomas, John R. and Oakley, E. Howard N. "Chapter 15: Nonfreezing Cold Injury" *Medical Aspects of Harsh Environments*, vol. 1. pp. 467-490, 2001.
Van Antwerp, Bill and Poonam Gulati, "Protein Delivery from Mechanical Devices Challenges and Opportunities," Medtronic presentation, 19 pages, Jul. 2003.
Weaver, James C., "Chapter 1 Electroporation Theory, Concepts and Mechanisms," Methods in Molecular Biology, vol. 55, Plant Cell Electroporation and Electrofusion Protocols, Edited by J.A. Nickoloff, Humana Press Inc., pp. 3-28, 1995.
Wilson, D.H. et al., "The Effects of Pulsed Electromagnetic Energy on Peripheral Nerve Regeneration," Annals New York Academy of Sciences, pp. 575-585, Oct. 1974.
Ye, Richard D., M.D., Ph.D., "Pharmacology of the Peripheral Nervous System," E-425 MSB, 6 pages, Jan. 2000.
Yong-Quan, Dong et al., "The therapeutic effect of pulsed electric field on experimental spinal cord injury," Beijing Army General Hospital of People's Liberation Army, Beijing, 5 pages (full article in Chinese; abstract on last page) Mar. 30, 1992.
"Micro ETS Hyperhidrosis USA" Hyperhidrosis USA. 2 pages. <URL: http://www.hyperhidrosis-usa.com/Index.html>. Nov. 6, 2006.
"Electrical Stimulation for the Treatment of Chronic Wounds," Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pages.
"Implantable Neurostimulation Systems," Medtronic Neurological, http://medtronic.com/neuro/paintherapies/pain_treatment_ladder/pdf/implantable_brochure.pdf.
Aggarwal, A. et al., Regional sympathetic effects of low-dose clonidine in heart failure. Hypertension. 2003;41:553-7.
Alexander, B.T. et al., "Renal denervation abolishes hypertension in low-birth-weight offspring from pregnant rats with reduced uterine perfusion," Hypertension, 2005; 45 (part 2): 754-758.
Barajas, L. "Innervation of the renal cortex." Fex Proc. 1978;37:1192-201.
Bello-Reuss, E. et al., "Acute unilateral renal denervation in rats with extracellular volume expansion," Departments of Medicine and Physiology, University of North Carolina School of Medicine. F26-F32, Jul. 1975.
Bello-Reuss, E. et al., "Effects of Acute Unilateral Renal Denervation in the Rat," J Clin Invest. 1975;56:208-217.
Bello-Reuss, E. et al., "Effect of renal sympathetic nerve stimualtion on proximal water and sodium reabsorption," J Clin Invest, 1976;57:1104-1107.
Bhandari, A. and Ellias, M., "Loin pain hematuria syndrome: Pain control with RFA to the Splanchanic plexus," The Pain Clinic, 2000, vol. 12, No. 4, pp. 323-327.

Bichet, D., et al., "Renal Intracortical blood flow and renin secretion after denervation by 6-hydroxydopamine." Can J Physiol Pharmacol. 1982;60:184-92.
Braunwald, E., Heart Disease, "A Textbook of Cardiovascular Medicine," 5th Ed., vol. 2, 1997, pp. 480-481, 824-825, 1184-1288 and 1923-1925, W.B. Saunders Company.
Burns, J. et al., "Relationship between central sympathetic drive and magnetic resonance imaging-determined left ventricular mass in essential hypertension." Circulation. 2007;115:1999-2005.
Campese, V.M. et al., "Renal afferent denervation prevents hypertension in rats with chronic renal failure." Hypertension. 1995; 25:878-82.
Campese, V.M., "Neurogenic factors and hypertension in renal disease." Kidney Int. 2000;57 Suppl 75:S2-3.
Chin, J.L. et al., "Renal autotransplantation for the loin pain-hematuria syndrome; long term follow up of 26 cases," J Urol, 1998, vol. 160, pp. 1232-1236.
Curtis, J.J. et al., "Surgical therapy for persistent hypertension after renal transplantation," Transplantation, 1981, 31(2):125-128.
Devereaux, R.B. et al., "Regression of Hypertensive Left Ventricular Hypertrophy by Losartan Compared With Atenolol: The Losartan Intervention for Endpoint Reduction in Hypertension (LIFE) Trial," Circulation, 2004, vol. 110, pp. 1456-1462.
Esler, M. et al., "Mechanism of elevated plasma noradrenaline in the course of essential hypertension." J Cardiovasc Pharmacol. 1986; 8:S39-43.
Esler, M. et al., "Noradrenaline release and the pathophysiology of primary human hypertension." Am J Hypertens. 1989; 2:140S-146S.
Esler, M et al., "Sympathetic nerve biology in essential hypertension," Clin and Exp Pharmacology and Physiology, 2001, 28: 986-989
Evelyn, K.A. et al., "Effect of thoracolumbar sympathectomy on the clinical course of primary (essential) hypertension," Am J Med, 1960;28:188-221.
Fajarco, J. et al., Effect of chemical sympathectomy on renal hydroelectrolytic handling in dogs with chronic caval constriction. Clin Physiol Biochem. 1986;4:252-6.
Final Office Action; U.S. Appl. No. 11/233,814; Mailed on Jan. 29, 2009, 11 pages.
Final Office Action; U.S. Appl. No. 11/451,728; Mailed on Jan. 13, 2009, 7 pages.
Final Office Action; U.S. Appl. No. 11/599,649; Mailed on Jan. 15, 2009, 10 pages.
Fuster, Valentin et al. "ACC/AHA/ESC Practice Guidelines: ACA/AHA/ESC 2006 Guidelines for the Management of Patients with Atrial Fibrillation." JACC vol. 48, No. 4, Aug. 15, 2006.
Gazdar, A.F. and G.J. Dammin, "Neural degeneration and regeneration in human renal trnasplants," NEJM, Jul. 30, 1970, 283:222-244.
Getts, R.T. et al., "Regression of left ventricular hypertrophy after bilateral nephrectomy," Nephrol Dial Transplant, 2006, vol. 21, pp. 1089-1091.
Hampers, C.L. et al., "A hemodynamic evaluation of bilateral nephrectomy and hemodialysis in hypertensive man," Circulation. 1967;35:272-288.
Hansen, J.M. et al., "The transplanted human kidney does not achieve functional reinnervation," Clin Science, 1994, vol. 87, pp. 13-20.
Hasking, G.J. et al., "Norepinephrine spillover to plasma in patients with congestive heart failure: evidence of increased overall and cardiorenal sympathetic nervous activity." Circulation. 1986;73:615-21.
Hausberg, M. et al., "Sympathetic nerve activity in end-stage renal disease," Circulation, 2002, 106: 1974-1979.
International Search Report, PCT/US02/0039, Mailed Sep. 11, 2002, Applicant: Advanced Neuromodulation Systems, Inc.
International Search Report, PCT/US02/25712, Mailed on Apr. 23, 2003, Applicant: Cyberonics, Inc.
International Search Report, PCT/US03/08014, Mailed on Sep. 23, 2003, Applicant: The General Hospital Corporation.
International Search Report, PCT/US03/09764, Mailed on Oct. 28, 2003, Applicant: CVRX, Inc.
International Search Report and Written Opinion, PCT/US05/35693, Mailed on Mar. 8, 2006, Applicant: Ardian, Inc., 29 pages.

International Search Report and Written Opinion, PCT/US05/35757, Mailed on Dec. 27, 2006, Applicant: Ardian, Inc., 8 pages.
International Search Report and Written Opinion, PCT/US06/36120, Mailed on Jun. 25, 2008, Applicant: Ardian, Inc., 10 pages.
International Search Report and Written Opinion, PCT/US06/41889, Mailed on Oct. 20, 2008, Applicant: Ardian, Inc., 7 pages.
International Search Report and Written Opinion, PCT/US06/48822, Mailed on Aug. 15, 2008, Applicant: Ardian, Inc., 12 pages.
International Search Report and Written Opinion, PCT/US07/63322, Mailed on Mar. 3, 2008, Applicant: Ardian, Inc., 13 pages.
International Search Report and Written Opinion, PCT/US07/63324, Mailed on Oct. 10, 2008, Applicant: Ardian, Inc., 13 pages.
International Search Report and Written Opinion, PCT/US07/66539, Mailed on Jan. 28, 2008, Applicant: Ardian, Inc., 8 pages.
International Search Report and Written Opinion, PCT/US07/70799, Mailed on Jul. 2, 2008, Applicant: Ardian, Inc., 7 pages.
International Search Report and Written Opinion, PCT/US07/72396, Mailed on Aug. 27, 2008, Applicant: Ardian, Inc., 9 pages.
International Search Report and Written Opinion, PCT/US07/84701, Mailed on Aug. 21, 2008, Applicant: Ardian, Inc., 11 pages.
International Search Report and Written Opinion, PCT/US07/84705, Mailed on Jul. 28, 2008, Applicant: Ardian, Inc., 12 pages.
International Search Report and Written Opinion, PCT/US07/84708, Mailed on Aug. 11, 2008, Applicant: Ardian, Inc., 9 pages.
Jones, J.A. et al., "Causes and Consequences of Increased Sympathetic Activity in Renal Disease." Hypertension. 2004;43:699-706.
Kassab, S. et al., "Renal denervation attenuates the sodium retention and hypertension associated with obesity," Hypertension, 1995, 25:893-897.
Katholi, R.E. et al., "Importance of the renal nerves in established two-kidney, one clip Goldblatt hypertension," Hypertension, 1982, 4 (suppl II): II-166-II-174.
Katholi, R.E. et al., "Role of the renal nerves in the pathogenesis of one-kidney renal hypertension in the rat," Hypertension, 1981, 3(4) 404-409.
Katholi, R.E., "Renal nerves and hypertension: an update," Fed Proc., 1985, 44:2846-2850.
Kaye, D.M. et al., "Functional and neurochemical evidence for partial cardiac sympathetic reinnervation after cardiac transplantation in humans," Circulation, 1993, vol. 88, pp. 1101-1109.
Kirchheim, H. et al., "Sympathetic modulation of renal hemodynamics, renin release and sodium excretion," Klin Wochenschr, 1989, 67:858-864.
Klein, K. et al., "Impaired autofeedback regulation of hypothalamic norepinephrine release in experimental uremia." J Am Soc Nephrol. 2005;16:2081-7.
Kopp, U. et al., "Dietary sodium loading increases arterial pressure in afferent renal-denervated rats," Hypertension, 2003, 42:968-973.
Kopp, U.C. et al., "Renal sympathetic nerve activity modulates afferent renal nerve activity by PGE2-dependent activation of alpha1- and alpha2-adrenoceptors on renal sensory nerve fibers." Am J Physiol Regul Integr Comp Physiol. 2007;293:R1561-72.
Le Noble, J.L. et al., "Pharmacological evidence for rapid destruction of efferent renal nerves in rats by intrarenal infusion of 6-hydoxydopamine." J Hypertens Suppl. 1985;3:S137-40.
Lenoble, L.M. et al., "Selective efferent chemical sympathectomy of rat kidneys." Am J Physiol. 1985;249:R496-501.
Luippold, G. et al., "Chronic renal denervation prevents glomerular hyperfiltration in diabetic rats," Nephrol Dial Transplant (2004) 19:342-347.
Medtronic Inc., MiniMed 2007, "Implantable Insulin Pump System" (Shoreview, MN) 4 pages.
Morrisey, D.M. et al., "Sympathectomy in the treatment of hypertension: Reivew of 122 cases,"Lancet. 1953;1:403-408.
Final Office Action; U.S. Appl. No. 10/408,665; Mailed on Mar. 21, 2006, 14 pages.
Non-Final Office Action; U.S. Appl. No. 11/129,765; Mailed on Oct. 6, 2006, 30 pages.
Non-Final Office Action; U.S. Appl. No. 11/129,765; Mailed on May 18, 2007, 10 pages.
Non-Final Office Action; U.S. Appl. No. 11/129,765; Mailed on Sep. 10, 2007, 5 pages.
Non-Final Office Action; U.S. Appl. No. 11/133,925; Mailed on Oct. 8, 2008, 41 pages.
Non-Final Office Action; U.S. Appl. No. 11/144,173; Mailed on Apr. 5, 2007, 33 pages.
Non-Final Office Action; U.S. Appl. No. 11/144,173; Mailed on Sep. 10, 2007, 5 pages.
Non-Final Office Action; U.S. Appl. No. 11/144,298; Mailed on Apr. 5, 2007, 33 pages.
Non-Final Office Action; U.S. Appl. No. 11/144,298; Mailed on Sep. 10, 2007, 5 pages.
Non-Final Office Action; U.S. Appl. No. 11/144,298; Mailed on Dec. 29, 2008, 7 pages.
Non-Final Office Action; U.S. Appl. No. 11/145,122; Mailed on Apr. 11, 2007, 33 pages.
Non-Final Office Action; U.S. Appl. No. 11/145,122; Mailed on Sep. 10, 2007, 5 pages.
Non-Final Office Action; U.S. Appl. No. 11/233,814; Mailed on Jun. 17, 2008, 12 pages.
Non-Final Office Action; U.S. Appl. No. 11/266,993; Mailed on Dec. 30, 2008, 7 pages.
Non-Final Office Action; U.S. Appl. No. 11/363,867; Mailed on Sep. 25, 2008, 10 pages.
Non-Final Office Action; U.S. Appl. No. 11/451,728; Mailed on Jun. 12, 2008, 41 pages.
Non-Final Office Action; U.S. Appl. No. 11/599,649; Mailed on Jun. 23, 2008, 9 pages.
O'Hagan, K.P. et al., "Renal denervation decreases blood pressure in DOCA-treated miniature swine with established hypertension," Am J Hypertens., 1990, 3:62-64.
Onesti, G. et al., "Blood pressure regulation in end-stage renal disease and anephric man," Circ Res Suppl., 1975, 36 & 37: 145-152.
Osborn, et al., "Effect of renal nerve stimulation on renal blood flow autoregulation and antinatriuresis during reductions in renal perfusion pressure," in Proceedings of the Society for Experimental Biology and Medicine, vol. 168, 77-81, 1981 (Abstract).
Paige, I.H. et al., "The Effect of Renal Denervation on the Level of Arterial Blood Pressure and Renal Function in Essential Hypertension." J Clin Invest. 1935;14:27-30.
Pappone, Carol and Santinelli, Vincenzo. "Multielectrode basket catheter: A new tool for curing atrial fibrillation?" Heart Rhythm, vol. 3, Issue 4, pp. 385-386. Apr. 2006.
Petersson, M. et al., "Long-term outcome in relation to renal sympathetic activity in patients with chronic heart failure," Eur Heart J. 2005;26:906-13.
Pitt, B. et al., "Effects of Eplerenone, Enalapril, and Eplerenone/Enalapril in Patients With Essential Hypertension and Left Ventricular Hypertrophy: The 4E-Left Ventricular Hypertrophy Study," Circulation, 2003, vol. 108, pp. 1831-1838.
Pope, Jill. "Fixing a Hole: Treating Injury by Repairing Cells." The New York Academy of Sciences. Jul. 6, 2006. 6 pages.
Schlaich, M.P. et al., Relation between cardiac sympathetic activity and hypertensive left ventricular hypertrophy. Circulation. 2003;108:560-5.
Schlaich, M.P. et al., "Sympathetic augmentation in hypertension: role of nerve firing, norepinephrine reuptake, and angiotensin neuromodulation," Hypertension, 2004, 43:169-175.
Shannon, J.L. et al., "Studies on the innervation of human renal allografts," J Pathol. 1998, vol. 186, pp. 109-115.
Shlipak, M.G. et al., "The clinical challenge of cardiorenal syndrome." Circulation. 2004; 110-1514-7.
Smithwick, R.H. et al., "Hypertension and associate cardiovascular disease: comparison of male and female mortality rates and their influence on selection of therapy," JAMA, 1956, 160:1023-1033.
Smithwick, R.H. et al., "Splanchnicectomy for essential hypertension," Journal Am Med Assn, 1953;152:1501-1504.
Solis-Herruzo, J.A. et al., "Effects of lumbar sympathetic block on kidney function in cirrhotic patients with hepatorenal syndrome," Journal of Hepatology, 1987; 5: 167-173.
Strojek, K. et al., "Lowering of microalbuminuria in diabetic patients by a sympathicoplegic agent: novel approach to prevent progression of diabetic nephropathy?" J Am Soc Nephrol. 2001;12:602-5.

Vonend, O. et al., "Moxonidine treatment of hypertensive patients with advanced renal failure." J Hypertens. 2003;21:1709-17.

Ye, S. et al., "A limited renal injury may cause a permanent form of neurogenic hypertension." Am J Hypertens. 1998;11:723-8.

Zanchetti, A. et al., "Practice Guidelines for Primary Care Physicians: 2003 ESH/ESC Hypertension Guidelines," Journal of Hypertension, vol. 21, No. 10, 2003, pp. 1779-1786.

Zanchetti, A.S., "Neural regulation of renin release: Experimental evidence and clinical implications in arterial hypertension," Circulation, 1977, 56(5) 691-698.

Zoccali, C. et al., "Plasma norepinephrine predicts survival and incident cardiovascular events in patients with end-stage renal disease." *Circulation*. 2002;105:1654-9.

Wittkampf et al., "Control of Radiofrequency lesion size by power regulation," AHA Journals 1989, 8 pages.

Avitall et al., "The creation of linear contiguous lesions in the atria with an expandable loop catheter," Journal Am. Coll. Cardiol. 1993, 15 pages.

Zheng et al., "Comparison of the Temperature Profile and Pathological Effect at Unipolar, Bipolar and Phased Radiofrequency Current Configurations," Journal of Interverventional Cardiac Electorphysiology, Jun. 19, 2001, 10 pages.

Opposition to European Patent No. EP2092957, Granted Jan. 5, 2011, Date of Opposition Oct. 5, 2011, 26 pages.

Opposition to European Patent No. EP1802370, Granted Jan. 5, 2011, Date of Opposition Oct. 5, 2011, 20 pages.

Bravo, E.L., et al., "Renal denervation for resistant hypertension," American Journal of Kidney Diseases, 2009, 3 pages.

Dibona, Gerald F., L.L. Sawin, Effect of renal nerve stimulation on NaCl and H2O transport in Henle's loop of the rat,: 1982, American Physiological Society, F576-F580, 5 pages.

* cited by examiner

*Primary Examiner* — Mark W Bockelman

(74) *Attorney, Agent, or Firm* — Perkins Coie LLP

(57) ABSTRACT

Methods and apparatus are provided for treating hypertension, e.g., via a pulsed electric field, via a stimulation electric field, via localized drug delivery, via high frequency ultrasound, via thermal techniques, etc. Such neuromodulation may effectuate irreversible electroporation or electrofusion, necrosis and/or inducement of apoptosis, alteration of gene expression, action potential attenuation or blockade, changes in cytokine up-regulation and other conditions in target neural fibers. In some embodiments, neuromodulation is applied to neural fibers that contribute to renal function. In some embodiments, such neuromodulation is performed in a bilateral fashion. Bilateral renal neuromodulation may provide enhanced therapeutic effect in some patients as compared to renal neuromodulation performed unilaterally, i.e., as compared to renal neuromodulation performed on neural tissue innervating a single kidney.

28 Claims, 10 Drawing Sheets

METHODS FOR RENAL NEUROMODULATION

CROSS-REFERENCE TO RELATED APPLICATIONS

The present application is a continuation-in-part of each of the following United States patent applications:

(1) U.S. patent application Ser. No. 10/408,665, filed on Apr. 8, 2003 now U.S. Pat. No. 7,162,303 (published as U.S. Patent Publication 2003/0216792 on Nov. 20, 2003), which claims the benefit of U.S. Provisional Patent Application Nos. 60/442,970, filed on Jan. 29, 2003; 60/415,575, filed on Oct. 3, 2002; and 60/370,190, filed on Apr. 8, 2002.

(2) U.S. patent application Ser. No. 11/133,925, filed on May 20, 2005, which is a continuation of U.S. patent application Ser. No. 10/900,199, filed on Jul. 28, 2004 (now U.S. Pat. No. 6,978,174), which is a continuation-in-part of U.S. patent application Ser. No. 10/408,665, filed on Apr. 8, 2003 now U.S. Pat. No. 7,162,303.

(3) U.S. patent application Ser. No. 11/189,563, filed on Jul. 25, 2005, which is a continuation-in-part of U.S. patent application Ser. No. 11/129,765, filed on May 13, 2005 now U.S. Pat. No. 7,653,438, which claims the benefit of U.S. Provisional Patent Application Nos. 60/616,254, filed on Oct. 5, 2004; and 60/624,793, filed on Nov. 2, 2004.

(4) U.S. patent application Ser. No. 11/266,993, filed on Nov. 4, 2005 now U.S. Pat. No. 7,756,583.

(5) U.S. patent application Ser. No. 11/363,867, filed on Feb. 27, 2006, which (a) claims the benefit of U.S. Provisional Application No. 60/813,589, filed on Dec. 29, 2005 and (b) is a continuation-in-part of each of U.S. patent application Ser. No. 11/189,563, filed on Jul. 25, 2005, and U.S. patent application Ser. No. 11/266,993, filed on Nov. 4, 2005 now U.S. Pat. No. 7,756,583.

All of the foregoing applications, publication and patent are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for neuromodulation. In some embodiments, the present invention relates to methods and apparatus for achieving bilateral renal neuromodulation.

BACKGROUND

Congestive Heart Failure ("CHF") is a condition that occurs when the heart becomes damaged and reduces blood flow to the organs of the body. If blood flow decreases sufficiently, kidney function becomes altered, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. Moreover, the fluid overload and associated clinical symptoms resulting from these physiologic changes result in additional hospital admissions, poor quality of life and additional costs to the health care system.

In addition to their role in the progression of CHF, the kidneys play a significant role in the progression of Chronic Renal Failure ("CRF"), End-Stage Renal Disease ("ESRD"), hypertension (pathologically high blood pressure) and other cardio-renal diseases. The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys.

It has been established in animal models that the heart failure condition results in abnormally high sympathetic activation of the kidneys. An increase in renal sympathetic nerve activity leads to decreased removal of water and sodium from the body, as well as increased renin secretion. Increased renin secretion leads to vasoconstriction of blood vessels supplying the kidneys which causes decreased renal blood flow. Reduction of sympathetic renal nerve activity, e.g., via denervation, may reverse these processes.

Applicants have previously described methods and apparatus for treating renal disorders by applying a pulsed electric field to neural fibers that contribute to renal function. See, for example, Applicants' co-pending U.S. patent applications Ser. No. 11/129,765, filed on May 13, 2005, and Ser. No. 11/189,563, filed on Jul. 25, 2005, both of which are incorporated herein by reference in their entireties. A pulsed electric field ("PEF") may initiate renal neuromodulation, e.g., denervation, for example, via irreversible electroporation or via electrofusion. The PEF may be delivered from apparatus positioned intravascularly, extravascularly, intra-to-extravascularly or a combination thereof. Additional methods and apparatus for achieving renal neuromodulation, e.g., via localized drug delivery (such as by a drug pump or infusion catheter) or via use of a stimulation electric field, etc, are described, for example, in co-owned and co-pending U.S. patent application Ser. No. 10/408,665, filed Apr. 8, 2003, and U.S. Pat. No. 6,978,174, both of which are incorporated herein by reference in their entireties.

As used herein, electrofusion comprises fusion of neighboring cells induced by exposure to an electric field. Contact between target neighboring cells for the purposes of electrofusion may be achieved in a variety of ways, including, for example, via dielectrophoresis. In tissue, the target cells may already be in contact, thus facilitating electrofusion.

As used herein, electroporation and electropermeabilization are methods of manipulating the cell membrane or intracellular apparatus. For example, the porosity of a cell membrane may be increased by inducing a sufficient voltage across the cell membrane through, e.g., short, high-voltage pulses. The extent of porosity in the cell membrane (e.g., size and number of pores) and the duration of effect (e.g., temporary or permanent) are a function of multiple variables, such as field strength, pulse width, duty cycle, electric field orientation, cell type or size and/or other parameters.

Cell membrane pores will generally close spontaneously upon termination of relatively lower strength -electric fields or relatively shorter pulse widths (herein defined -as "reversible electroporation"). However, each cell or cell type has a critical threshold above which pores do not close such that pore formation is no longer reversible; this result is defined as "irreversible electroporation," "irreversible breakdown" or "irreversible damage." At this point, the cell membrane ruptures and/or irreversible chemical imbalances caused by the high porosity occur. Such high porosity can be the result of a single large hole and/or a plurality of smaller holes.

A potential challenge of using intravascular PEF systems for treating renal disorders is to selectively electroporate target cells without affecting other cells. For example, it may be desirable to irreversibly electroporate renal nerve cells that travel along or in proximity to renal vasculature, but it may not be desirable to damage the smooth muscle cells of which the vasculature is composed. As a result, an overly aggressive course of PEF therapy may persistently injure the renal vasculature, but an overly conservative course of PEF therapy may not achieve the desired renal neuromodulation.

Applicants have previously described methods and apparatus for monitoring tissue impedance or conductivity to determine the effects of pulsed electric field therapy, e.g., to determine an extent of electroporation and/or its degree of irreversibility. See, for example, Applicant's co-pending U.S. patent application Ser. No. 11/233,814, filed Sep. 23, 2005, which is incorporated herein by reference in its entirety. Pulsed electric field electroporation of tissue causes a decrease in tissue impedance and an increase in tissue conductivity. If induced electroporation is reversible, tissue impedance and conductivity should approximate baseline levels upon cessation of the pulsed electric field. However, if electroporation is irreversible, impedance and conductivity changes should persist after terminating the pulsed electric field. Thus, monitoring the impedance or conductivity of target and/or non-target tissue may be utilized to determine the onset of electroporation and to determine the type or extent of electroporation. Furthermore, monitoring data may be used in one or more manual or automatic feedback loops to control the electroporation.

It would be desirable to provide methods and apparatus for achieving bilateral renal neuromodulation.

SUMMARY

The present invention provides methods and apparatus for neuromodulation, e.g., via a pulsed electric field ("PEF"), via a stimulation electric field, via localized drug delivery, via high frequency ultrasound, via thermal techniques, combinations thereof, etc. Such neuromodulation may, for example, effectuate irreversible electroporation or electrofusion, necrosis and/or inducement of apoptosis, alteration of gene expression, action potential blockade or attenuation, changes in cytokine up-regulation and other conditions in target neural fibers. In some patients, when the neuromodulatory methods and apparatus of the present invention are applied to renal nerves and/or other neural fibers that contribute to renal neural functions, applicants believe that the neuromodulatory effects induced by the neuromodulation might result in increased urine output, decreased plasma renin levels, decreased tissue (e.g., kidney) and/or urine catecholamines (e.g., norepinephrine), increased urinary sodium excretion, and/or controlled blood pressure. Furthermore, applicants believe that these or other changes might prevent or treat congestive heart failure, hypertension, acute myocardial infarction, end-stage renal disease, contrast nephropathy, other renal system diseases, and/or other renal or cardio-renal anomalies. The methods and apparatus described herein could be used to modulate efferent or afferent nerve signals, as well as combinations of efferent and afferent nerve signals.

Renal neuromodulation preferably is performed in a bilateral fashion, such that neural fibers contributing to renal function of both the right and left kidneys are modulated. Bilateral renal neuromodulation may provide enhanced therapeutic effect in some patients as compared to renal neuromodulation performed unilaterally, i.e., as compared to renal neuromodulation performed on neural tissue innervating a single kidney. In some embodiments, concurrent modulation of neural fibers that contribute to both right and left renal function may be achieved. In additional or alternative embodiments, such modulation of the right and left neural fibers may be sequential. Bilateral renal neuromodulation may be continuous or intermittent, as desired.

When utilizing an electric field, the electric field parameters may be altered and combined in any combination, as desired. Such parameters can include, but are not limited to, voltage, field strength, pulse width, pulse duration, the shape of the pulse, the number of pulses and/or the interval between pulses (e.g., duty cycle), etc. For example, when utilizing a pulsed electric field, suitable field strengths can be up to about 10,000 V/cm and suitable pulse widths can be up to about 1 second. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, or combinations. The field includes at least one pulse, and in many applications the field includes a plurality of pulses. Suitable pulse intervals include, for example, intervals less than about 10 seconds. These parameters are provided as suitable examples and in no way should be considered limiting.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which.

DETAILED DESCRIPTION

A. Overview

The present invention relates to methods and apparatus for neuromodulation, e.g., denervation. In some embodiments, the present invention provides methods and apparatus for achieving bilateral renal neuromodulation. Bilateral renal neuromodulation may provide enhanced therapeutic effect in some patients as compared to renal neuromodulation performed unilaterally, i.e., as compared to renal neuromodulation performed on neural tissue innervating a single kidney. In some embodiments, concurrent modulation of neural fibers that contribute to both right and left renal function may be achieved. In additional or alternative embodiments, such modulation of the right and left neural fibers may be sequential. Bilateral renal neuromodulation may be continuous or intermittent, as desired.

The methods and apparatus of the present invention may be used to modulate neural fibers that contribute to renal function and may exploit any suitable neuromodulatory techniques that will achieve the desired neuromodulation. For example, any suitable electrical signal or field parameters, e.g., any electric field that will achieve the desired neuromodulation (e.g., electroporative effect) may be utilized. Alternatively or additionally, neuromodulation may be achieved via localized delivery of a neuromodulatory agent or drug. To better understand the structures of devices of the present invention and the methods of using such devices for bilateral renal neuromodulation, it is instructive to examine the renal anatomy in humans.

B. Selected Embodiments of Methods for Neuromodulation

Figure 1:
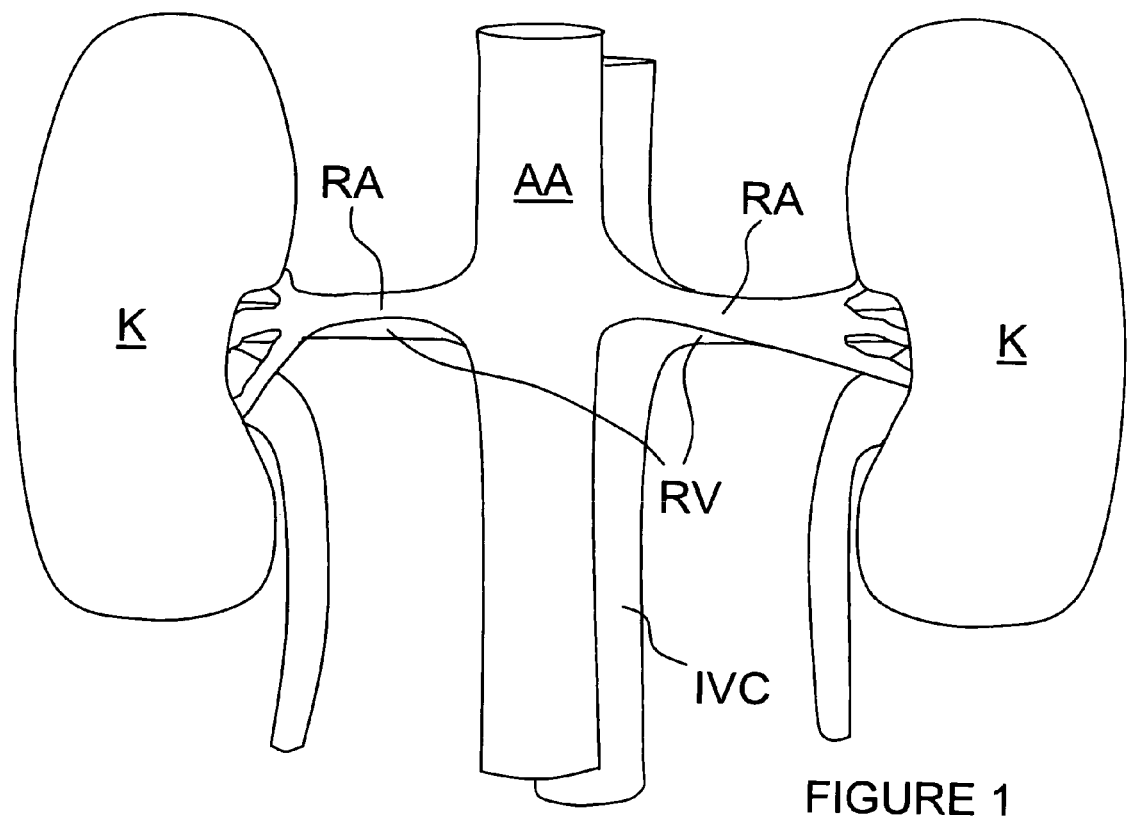
FIG. 1 is a schematic view illustrating human renal anatomy.
Figure 2:
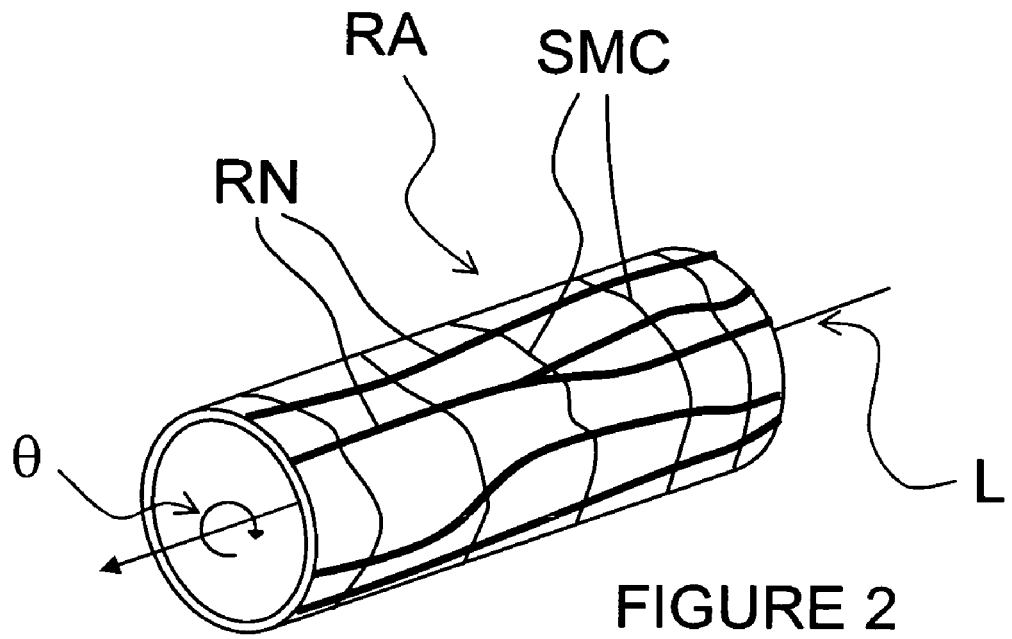
FIG. 2 is a schematic isometric detail view showing the location of the renal nerves relative to the renal artery.

With reference now to FIG. 1, the human renal anatomy includes kidneys K that are supplied with oxygenated blood by renal arteries RA, which are connected to the heart by the abdominal aorta AA. Deoxygenated blood flows from the kidneys to the heart via renal veins RV and the inferior vena cava IVC. FIG. 2 illustrates a portion of the renal anatomy in greater detail. More specifically, the renal anatomy also includes renal nerves RN extending longitudinally along the lengthwise dimension L of renal artery RA generally within the adventitia of the artery. The renal artery RA has smooth muscle cells SMC that surround the arterial circumference and spiral around the angular axis θ of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

Figure 3A:
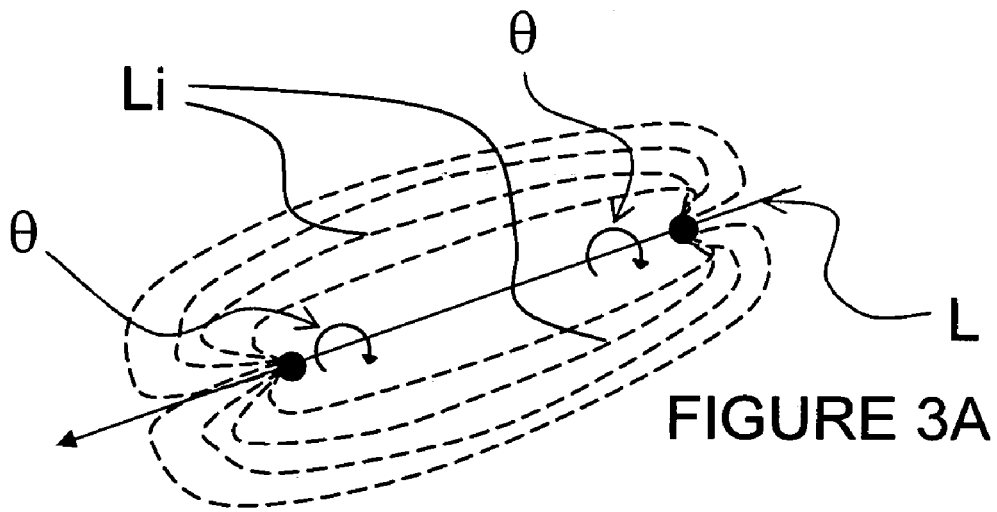
FIGS. 3A and 3B are schematic isometric and end views, respectively, illustrating orienting of an electric field for selectively affecting renal nerves.
Figure 3B:
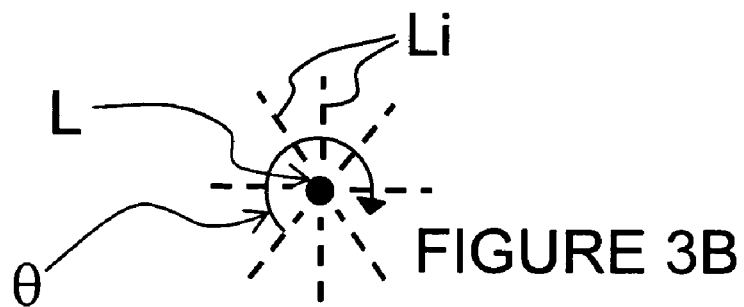

Referring to FIGS. 3A and 3B, the cellular misalignment of the renal nerves and the smooth muscle cells may be exploited to selectively affect renal nerve cells with reduced effect on smooth muscle cells. More specifically, because larger cells require a lower electric field strength to exceed the cell membrane irreversibility threshold voltage or energy for irreversible electroporation, embodiments of electrodes of the present invention may be configured to align at least a portion of an electric field generated by the electrodes with or near the longer dimensions of the cells to be affected. In specific embodiments, the device has electrodes configured to create an electrical field aligned with or near the lengthwise dimension L of the renal artery RA to affect renal nerves RN. By aligning an electric field so that the field preferentially aligns with the lengthwise aspect of the cell rather than the diametric or radial aspect of the cell, lower field strengths may be used to affect target neural cells, e.g., to necrose or fuse the target cells, to induce apoptosis, to alter gene expression, to attenuate or block action potentials, to change cytokine up-regulation and/or to induce other suitable processes. This is expected to reduce total energy delivered to the system and to mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning a pulsed electric field ("PEF") with the lengthwise or longer dimensions of the target cells, the PEF may propagate along the lateral or shorter dimensions of the non-target cells (i.e., such that the PEF propagates at least partially out of alignment with non-target smooth muscle cells SMC). Therefore, as seen in FIGS. 3A and 3B, applying a PEF with propagation lines Li generally aligned with the longitudinal dimension L of the renal artery RA is expected to preferentially cause electroporation (e.g., irreversible electroporation), electrofusion or other neuromodulation in cells of the target renal nerves RN without unduly affecting the non-target arterial smooth muscle cells SMC. The pulsed electric field may propagate in a single plane along the longitudinal axis of the renal artery, or may propagate in the longitudinal direction along any angular segment θ through a range of 0°-360°.

A PEF system placed within and/or in proximity to the wall of the renal artery may propagate an electric field having a longitudinal portion that is aligned to run with the longitudinal dimension of the artery in the region of the renal nerves RN and the smooth muscle cells SMC of the vessel wall so that the wall of the artery remains at least substantially intact while the outer nerve cells are destroyed, fused or otherwise affected. Monitoring elements may be utilized to assess an extent of, e.g., electroporation, induced in renal nerves and/or in smooth muscle cells, as well as to adjust PEF parameters to achieve a desired effect.

Figure 4:
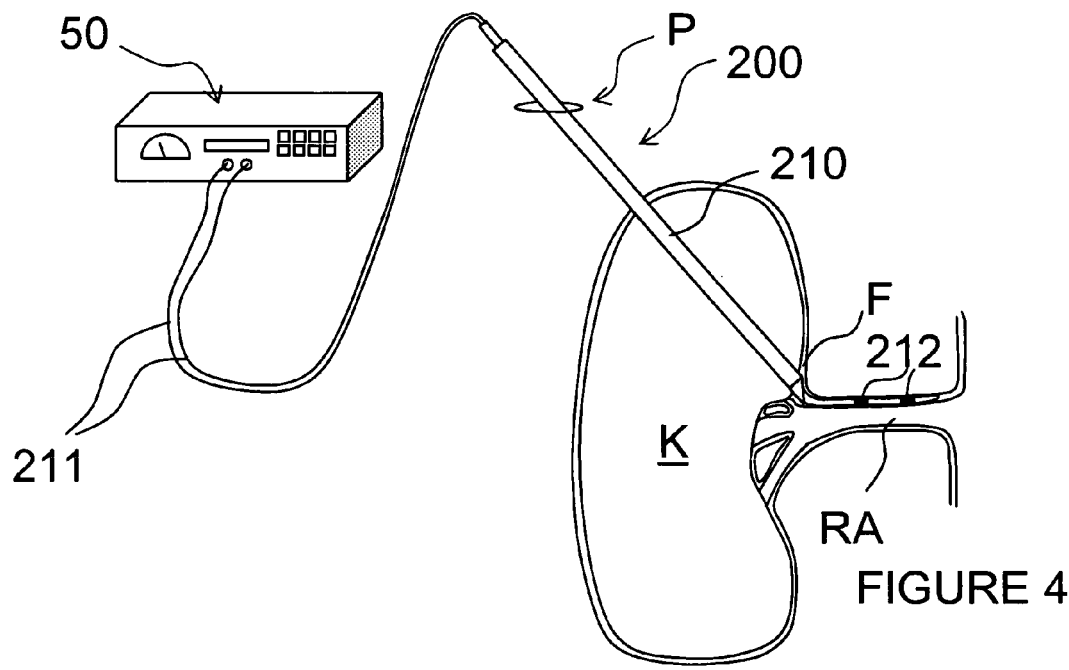
FIG. 4 is a schematic side view, partially in section, illustrating an example of an extravascular method and apparatus for renal neuromodulation.

C. Exemplary Embodiments of Systems and Additional Methods for Neuromodulation With reference to FIGS. 4 and 5, examples of PEF systems and methods are described. FIG. 4 shows one embodiment of an extravascular pulsed electric field apparatus 200 that includes one or more electrodes configured to deliver a pulsed electric field to renal neural fibers to achieve renal neuromodulation. The apparatus of FIG. 4 is configured for temporary extravascular placement; however, it should be understood that partially or completely implantable extravascular apparatus additionally or alternatively may be utilized. Applicants have previously described extravascular PEF systems, for example, in co-pending U.S. patent application Ser. No. 11/189,563, filed Jul. 25, 2005, which has been incorporated herein by reference in its entirety.

In FIG. 4, apparatus 200 comprises a laparoscopic or, percutaneous PEF system having a probe 210 configured for insertion in proximity to the track of the renal neural supply along the renal artery or vein or hilum and/or within Gerota's fascia under, e.g., CT or radiographic guidance. At least one electrode 212 is configured for delivery through the probe 210 to a treatment site for delivery of pulsed electric field therapy. The electrode(s) 212, for example, may be mounted on a catheter and electrically coupled to a pulse generator 50 via wires 211. In an alternative embodiment, a distal section of the probe 210 may have one electrode 212, and the probe may have an electrical connector to couple the probe to the pulse generator 50 for delivering a PEF to the electrode(s) 212.

The pulsed electric field generator 50 is located external to the patient. The generator, as well as any of the PEF-delivery electrode embodiments described herein, may be utilized with any embodiment of the present invention for delivery of a PEF with desired field parameters. It should be understood that PEF-delivery electrodes of embodiments described hereinafter may be electrically connected to the generator even though the generator is not explicitly shown or described with each embodiment.

The electrode(s) 212 can be individual electrodes that are electrically independent of each other, a segmented electrode with commonly connected contacts, or a continuous electrode. A segmented electrode may, for example, be formed by providing a slotted tube fitted onto the electrode, or by electrically connecting a series of individual electrodes. Individual electrodes or groups of electrodes 212 may be configured to provide a bipolar signal. The electrodes 212 may be dynamically assignable to facilitate monopolar and/or bipolar energy delivery between any of the electrodes and/or between any of the electrodes and an external ground pad. Such a ground pad may, for example, be attached externally to the patient's skin, e.g., to the patient's leg or flank. In FIG. 4, the electrodes 212 comprise a bipolar electrode pair. The probe 210 and the electrodes 212 may be similar to the standard needle or trocar-type used clinically for pulsed RF nerve block. Alternatively, the apparatus 200 may comprise a flexible and/or custom-designed probe for the renal application described herein.

In FIG. 4, the percutaneous probe 210 has been advanced through a percutaneous access site P into proximity with a patient's renal artery RA. The probe pierces the patient's Gerota's fascia F, and the electrodes 212 are advanced into position through the probe and along the annular space between the patient's artery and fascia. Once properly positioned, pulsed electric field therapy may be applied to target neural fibers across the bipolar electrodes 212. Such PEF therapy may, for example, at least partially denervate the kidney innervated by the target neural fibers through irreversible electroporation of cells of the target neural fibers. The electrodes 212 optionally also may be used to monitor the electroporative effects of the PEF therapy. After treatment, the apparatus 200 may be removed from the patient to conclude the procedure.

Figure 5A:
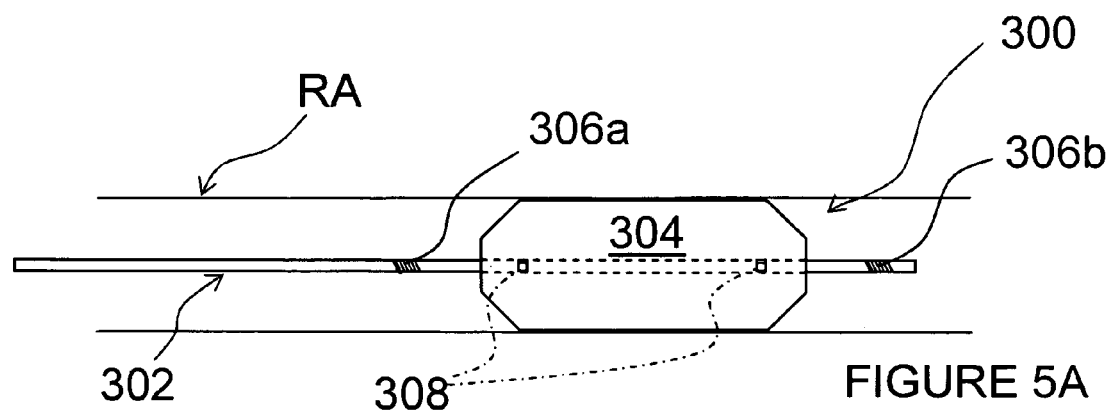
FIGS. 5A and 5B are schematic side views, partially in section, illustrating examples of, respectively, intravascular and intra-to-extravascular methods and apparatus for renal neurotmodulation.

Referring now to FIG. 5A, an embodiment of an intravascular PEF system is described. Applicants have previously described intravascular PEF systems, for example, in co-pending U.S. patent application Ser. No. 11/129,765, filed May 13, 2005, which has been incorporated herein by reference in its entirety. The embodiment of FIG. 5A includes an apparatus 300 comprising a catheter 302 having a centering element 304 (e.g., a balloon, an expandable wire basket, other mechanical expanders, etc.), shaft electrodes 306a and 306b disposed along the shaft of the catheter, and optional radiopaque markers 308 disposed along the shaft of the catheter in the region of the centering element 304. The electrodes 306a-b, for example, can be arranged such that the electrode 306a is near a proximal end of the centering element 304 and the electrode 306b is near the distal end of the centering element 304. The electrodes 306 are electrically coupled to the pulse generator 50 (see FIG. 4), which is disposed external to the patient, for delivery of the PEF therapy.

The centering element 304 may comprise an impedance-altering element that alters the impedance between electrodes 306a and 306b during the PEF therapy, for example, to better direct the PEF therapy across the vessel wall. This may reduce an applied voltage required to achieve desired renal neuromodulation. Applicants have previously described use of an impedance-altering element, for example, in co-pending U.S. patent application Ser. No. 11/266,993, filed Nov. 4, 2005, which is incorporated herein by reference in its entirety. When the centering element 304 comprises an inflatable balloon, the balloon may serve as both the centering element for the electrodes 306 and as an impedance-altering electrical insulator for directing an electric field delivered across the electrodes, e.g., for directing the electric field into or across the vessel wall for modulation of target neural fibers. Electrical insulation provided by the element 304 may reduce the magnitude of applied voltage or other parameters of the pulsed electric field necessary to achieve desired field strength at the target fibers.

The electrodes 306 can be individual electrodes (i.e., independent contacts), a segmented electrode with commonly connected contacts, or a single continuous electrode. Furthermore, the electrodes 306 may be configured to provide a bipolar signal, or the electrodes 306 may be used together or individually in conjunction with a separate patient ground pad for monopolar use. As an alternative or in addition to placement of the electrodes 306 along the central shaft of catheter 302, as in FIG. 5A, the electrodes 306 may be attached to the centering element 304 such that they contact the wall of the renal artery RA. In such a variation, the electrodes may, for example, be affixed to the inside surface, outside surface or at least partially embedded within the wall of the centering element. The electrodes optionally may be used to monitor the, effects of PEF therapy, as described hereinafter. As it may be desirable to reduce or minimize physical contact between the PEF-delivery electrodes and the vessel wall during delivery of PEF therapy, e.g., to reduce the potential for injuring the wall, the electrodes 306 may, for example, comprise a first set of electrodes attached to the shaft of the catheter for delivering the PEF therapy, and the device may further include a second set of electrodes optionally attached to the centering element 304 for monitoring the effects of PEF therapy delivered via the electrodes 306.

In use, the catheter 302 may be delivered to the renal artery RA as shown, or it may be delivered to a renal vein or to any other vessel in proximity to neural tissue contributing to renal function, in a low profile delivery configuration, for example, through a guide catheter. Once positioned within the renal vasculature, the optional centering element 304 may be expanded into contact with an interior wall of the vessel. A pulsed electric field then may be generated by the PEF generator 50, transferred through the catheter 302 to the electrodes 306, and delivered via the electrodes 306 across the wall of the artery. The PEF therapy modulates the activity along neural fibers that contribute to renal function, e.g., at least partially denervates the kidney innervated by the neural fibers. This may be achieved, for example, via irreversible electroporation, electrofusion and/or inducement of apoptosis in the nerve cells. In many applications, the electrodes are arranged so that the pulsed electric field is aligned with the longitudinal dimension of the renal artery to facilitate modulation of renal nerves with little effect on non-target smooth muscle cells or other cells.

In addition to extravascular and intravascular PEF systems, intra-to-extravascular PEF systems may be provided having electrode(s) that are delivered to an intravascular position, then at least partially passed through/across the vessel wall to an extravascular position prior to delivery of PEF therapy. Intra-to-extravascular positioning of the electrode(s) may place the electrode(s) in closer proximity to target neural fibers during the PEF therapy compared to fully intravascular positioning of the electrode(s). Applicants have previously described intra-to-extravascular PEF systems, for example, in co-pending U.S. patent application Ser. No. 11/324,188

(hereinafter, "the '188 application"), filed Dec. 29, 2005, which is incorporated herein by reference in its entirety.

Figure 5B:
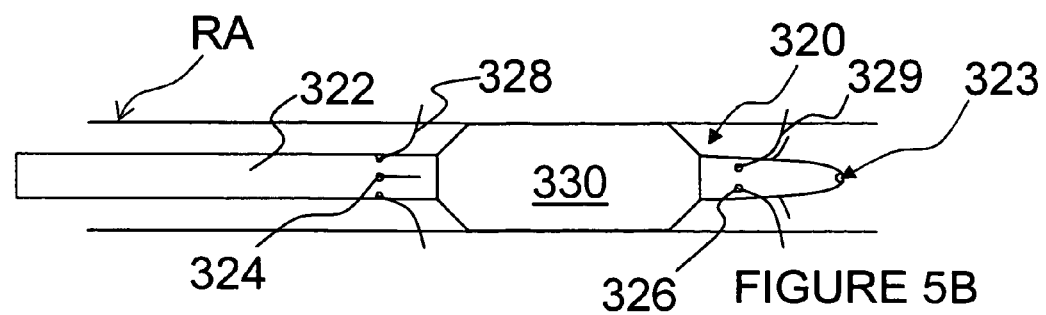

With reference to FIG. 5B, one embodiment of an intra-to-extravascular ("ITEV") PEF system, described previously in the '188 application, is shown. ITEV PEF system 320 comprises a catheter 322 having (a) a plurality of proximal electrode lumens terminating at proximal side-ports 324, (b) a plurality of distal electrode lumens terminating at distal side ports 326, and (c) a guidewire lumen 323. The catheter 322 preferably comprises an equal number of proximal and distal electrode lumens and side ports. The system 320 also includes proximal needle electrodes 328 that may be advanced through the proximal electrode lumens and the proximal side ports 324, as well as distal needle electrodes 329 that may be advanced through the distal electrode lumens and the distal side ports 326.

Catheter 322 comprises an optional expandable centering element 330, which may comprise an inflatable balloon or an expandable basket or cage. In use, the centering element 330 may be expanded prior to deployment of the needle electrodes 328 and 329 in order to center the catheter 322 within the patient's vessel (e.g., within renal artery RA). Centering the catheter 322 is expected to facilitate delivery of all needle electrodes to desired depths within/external to the patient's vessel (e.g., to deliver all of the needle electrodes approximately to the same depth). In FIG. 5B, the illustrated centering element 330 is positioned between the proximal side ports 324 and the distal side ports 326, i.e., between the delivery positions of the proximal and distal electrodes. However, it should be understood that centering element 330 additionally or alternatively may be positioned at a different location or at multiple locations along the length of the catheter 322 (e.g., at a location proximal of the side ports 324 and/or at a location distal of the side ports 326).

As illustrated in FIG. 5B, the catheter 322 may be advanced to a treatment site within the patient's vasculature (e.g., to a treatment site within the patient's renal artery RA) over a guidewire (not shown) via the lumen 323. During intravascular delivery, the electrodes 328 and 329 may be positioned such that their non-insulated and sharpened distal regions are positioned within the proximal and distal lumens, respectively. Once positioned at a treatment site, a medical practitioner may advance the electrodes via their proximal regions that are located external to the patient. Such advancement causes the distal regions of the electrodes 328 and 329 to exit side ports 324 and 326, respectively, and pierce the wall of the patient's vasculature such that the electrodes are positioned extravascularly via an ITEV approach.

The proximal electrodes 328 can be connected to PEF generator 50 as active electrodes and the distal electrodes 329 can serve as return electrodes. In this manner, the proximal and distal electrodes form bipolar electrode pairs that align PEF therapy with a longitudinal axis or direction of the patient's vasculature. As will be apparent, the distal electrodes 329 alternatively may comprise the active electrodes and the proximal electrodes 328 may comprise the return electrodes. Furthermore, the proximal and/or the distal electrodes may comprise both active and return electrodes. Any combination of active and distal electrodes may be utilized, as desired.

When the electrodes 328 and 329 are connected to PEF generator 50 and are positioned extravascularly, and with centering element 330 optionally expanded, PEF therapy may proceed to achieve desired neuromodulation. After completion of the PEF therapy, the electrodes may be retracted within the proximal and distal lumens, and centering element 330 may be collapsed for retrieval. ITEV PEF system 320 then may be removed from the patient to complete the procedure. Additionally or alternatively, the system may be repositioned to provide PEF therapy at another treatment site, for example, to provide bilateral renal neuromodulation.

It is expected that PEF therapy, as well as other methods and apparatus of the present invention for neuromodulation (e.g., stimulation electric fields, localized drug delivery, high frequency ultrasound, thermal techniques, etc.), whether delivered extravascularly, intravascularly, intra-to-extravascularly or a combination thereof, may, for example, effectuate irreversible electroporation or electrofusion, necrosis and/or inducement of apoptosis, alteration of gene expression, action potential blockade or attenuation, changes in cytokine up-regulation and other conditions in target neural fibers. In some patients, when such neuromodulatory methods and apparatus are applied to renal nerves and/or other neural fibers that contribute to renal neural functions, applicants believe that the neuromodulatory effects induced by the neuromodulation might result in increased urine output, decreased plasma renin levels, decreased tissue (e.g., kidney) and/or urine catecholamines (e.g., norepinephrine), increased urinary sodium excretion, and/or controlled blood pressure. Furthermore, applicants believe that these or other changes might prevent or treat congestive heart failure, hypertension, acute myocardial infarction, end-stage renal disease, contrast nephropathy, other renal system diseases, and/or other renal or cardio-renal anomalies for a period of months, potentially up to six months or more. This time period may be sufficient to allow the body to heal; for example, this period may reduce the risk of CHF onset after an acute myocardial infarction, thereby alleviating a need for subsequent re-treatment. Alternatively, as symptoms reoccur, or at regularly scheduled intervals, the patient may return to the physician for a repeat therapy. The methods and apparatus described herein could be used to modulate efferent or afferent nerve signals, as well as combinations of efferent and afferent nerve signals. Neuromodulation in accordance with the present invention preferably is achieved without completely physically severing, i.e., without fully cutting, the target neural fibers. However, it should be understood that such neuromodulation may functionally sever the neural fibers, even though the fibers may not be completely physically severed. Apparatus and methods described herein illustratively are configured for percutaneous use. Such percutaneous use may be endoluminal, laparoscopic, a combination thereof, etc.

The apparatus described above with respect to FIGS. 4 and 5 additionally may be used to quantify the efficacy, extent or cell selectivity of PEF therapy to monitor and/or control the therapy. When a pulsed electric field initiates electroporation, the impedance of the electroporated tissue begins to decrease and the conductivity of the tissue begins to increase. If the electroporation is reversible, the tissue electrical parameters will return or approximate baseline values upon cessation of the PEF. However, if the electroporation is irreversible, the changes in tissue parameters will persist after termination of the PEF. These phenomena may be utilized to monitor both the onset and the effects of PEF therapy. For example, electroporation may be monitored directly using, for example, conductivity measurements or impedance measurements, such as Electrical Impedance Tomography ("EIT") and/or other electrical impedance/conductivity measurements like an electrical impedance or conductivity index. Such electroporation monitoring data optionally may be used in one or more feedback loops to control delivery of PEF therapy.

In order to collect the desired monitoring data, additional monitoring electrodes optionally may be provided in proximity to the monitored tissue. The distance between such monitoring electrodes preferably would be specified prior to therapy delivery and used to determine conductivity from impedance or conductance measurements. For the purposes of the present invention, the imaginary part of impedance may be ignored such that impedance is defined as voltage divided by current, while conductance may be defined as the inverse of impedance (i.e., current divided by voltage), and conductivity may be defined as conductance per unit distance. Applicants have previously described methods and apparatus for monitoring PEF therapy, as well as exemplary PEF waveforms, in co-pending U.S. patent application Ser. No. 11/233, 814, filed Sep. 23, 2005, which has been incorporated herein by reference in its entirety.

Although the embodiments of FIGS. 4 and 5 illustratively comprise bipolar apparatus, it should be understood that monopolar apparatus alternatively may be utilized. For example, an active monopolar electrode may be positioned intravascularly, extravascularly or intra-to-extravascularly in proximity to target neural fibers that contribute to renal function. A return electrode ground pad may be attached to the exterior of the patient. Finally, PEF therapy may be delivered between to the in vivo monopolar electrode and the ground pad to effectuate desired renal neuromodulation. Monopolar apparatus additionally may be utilized for bilateral renal neuromodulation.

It may be desirable to achieve bilateral renal neuromodulation. Bilateral neuromodulation may enhance the therapeutic effect in some patients as compared to renal neuromodulation performed unilaterally, i.e., as compared to renal neuromodulation performed on neural tissue innervating a single kidney. For example, bilateral renal neuromodulation may further reduce clinical symptoms of CHF, hypertension, acute myocardial infarction, contrast nephropathy, renal disease and/or other cardio-renal diseases. FIGS. 6A-6H illustrate stages of a method for bilateral renal neuromodulation utilizing the intravascular apparatus of FIG. 5A. However, it should be understood that such bilateral neuromodulation alternatively may be achieved utilizing the extravascular apparatus of FIG. 4, utilizing the intra-to-extravascular apparatus of FIG. 5B, or utilizing any alternative intravascular apparatus, extravascular apparatus, intra-to-extravascular apparatus (including monopolar apparatus) or combination thereof.

Figure 6A:
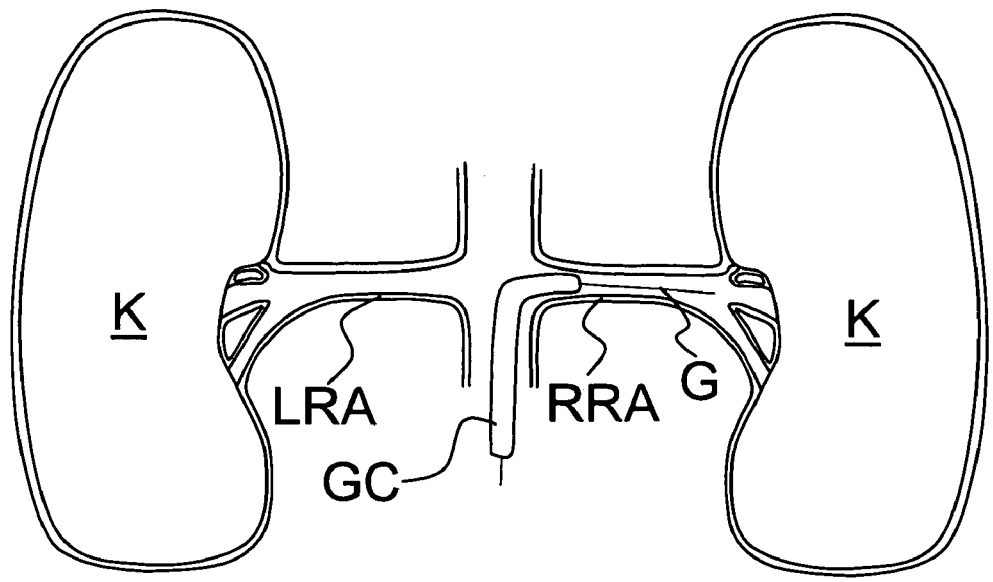
FIGS. 6A-6H are schematic side views, partially in section, illustrating methods of achieving bilateral renal neuromodulation utilizing apparatus of the present invention, illustratively utilizing the apparatus of FIG. 5A.
Figure 6B:
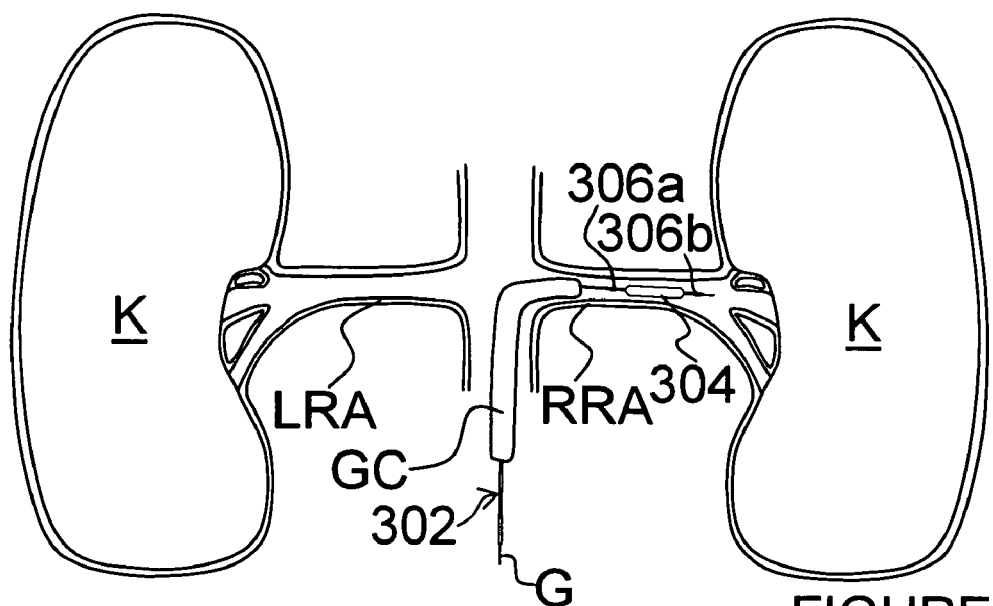
Figure 6C:
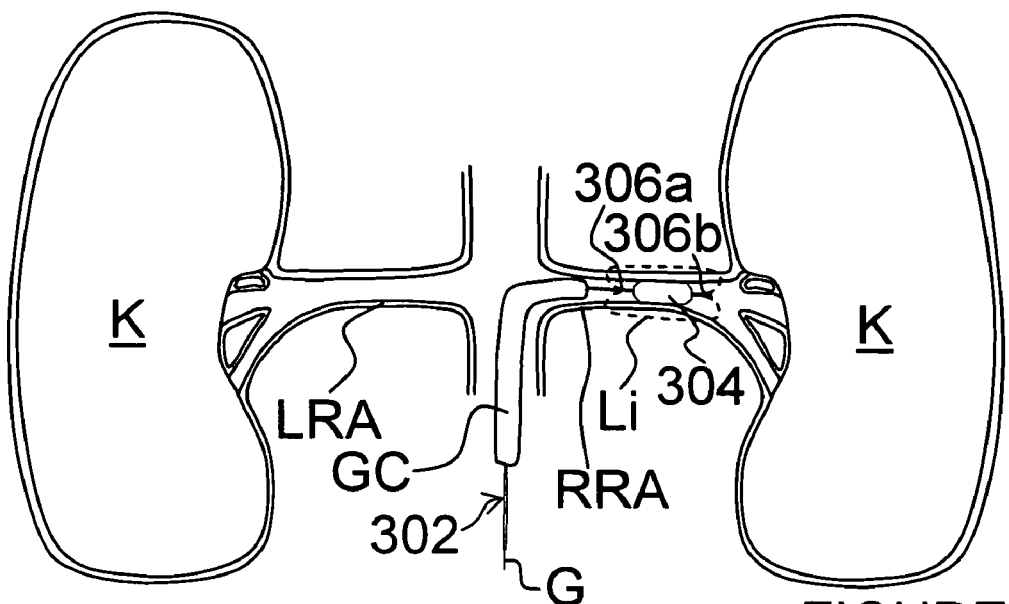
Figure 6D:
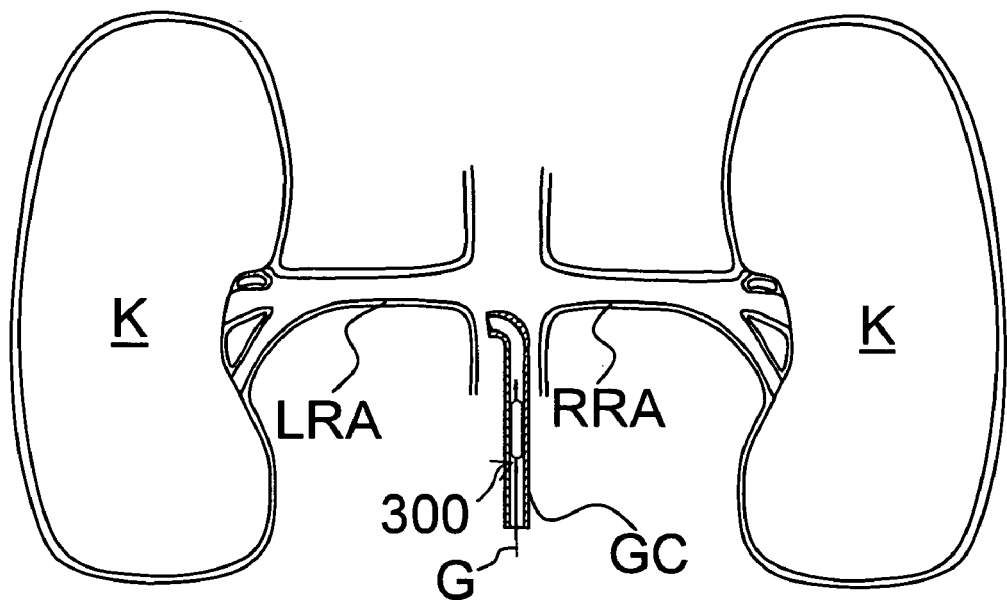
Figure 6E:
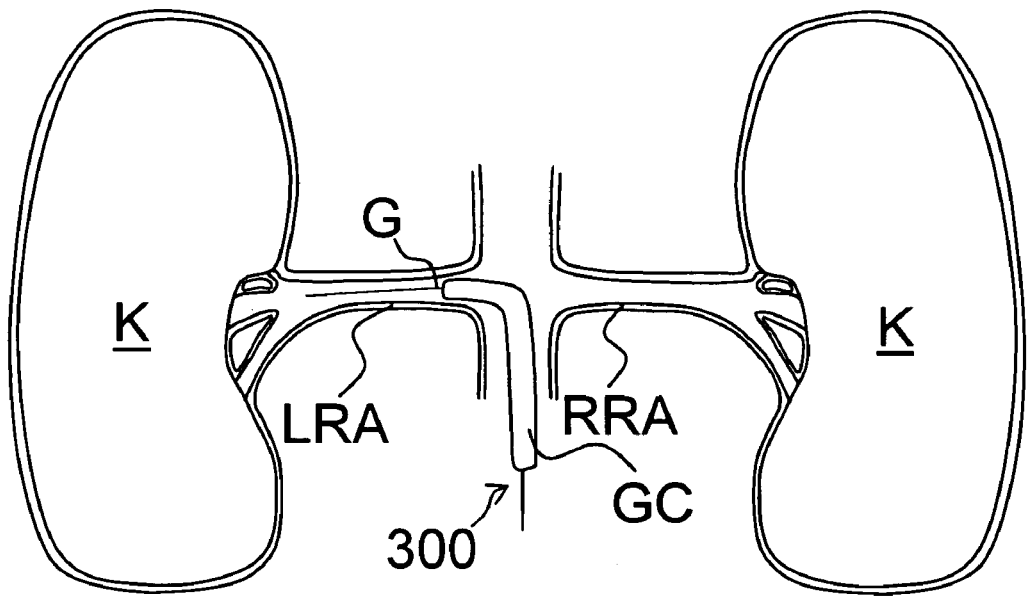

As seen in FIGS. 6A and 6E, a guide catheter GC and a guidewire G may be advanced into position within, or in proximity to, either the patient's left renal artery LRA or right renal artery RRA. In FIG. 6A, the guidewire illustratively has been positioned in the right renal artery RRA, but it should be understood that the order of bilateral renal neuromodulation illustrated in FIGS. 6A-6H alternatively may be reversed. Additionally or alternatively, bilateral renal neuromodulation may be performed concurrently on both right and left neural fibers that contribute to renal function, as in FIGS. 7-9, rather than sequentially, as in FIGS. 6.

With the guidewire and the guide catheter positioned in the right renal artery, the catheter 302 of the apparatus 300 may be advanced over the guidewire and through the guide catheter into position within the artery. As seen in FIG. 6B, the optional centering element 304 of the catheter 302 is in a reduced delivery configuration during delivery of the catheter to the renal artery. In FIG. 6C, once the catheter is properly positioned for PEF therapy, the element 304 optionally may be expanded into contact with the vessel wall, and the guidewire G may be retracted from the treatment zone, e.g., may be removed from the patient or may be positioned more proximally within the patient's aorta.

Expansion of element 304 may center the electrodes 306 within the vessel and/or may alter impedance between the electrodes. With apparatus 300 positioned and deployed as desired, PEF therapy may be delivered in a bipolar fashion across the electrodes 306 to achieve renal neuromodulation in neural fibers that contribute to right renal function, e.g., to at least partially achieve renal denervation of the right kidney. As illustrated by propagation lines Li, the pulsed electric field may be aligned with a longitudinal dimension of the renal artery RA and may pass across the vessel wall. The alignment and propagation path of the pulsed electric field is expected to preferentially modulate cells of the target renal nerves without unduly affecting non-target arterial smooth muscle cells.

As seen in FIG. 6D, after completion of the PEF therapy, the element 304 may be collapsed back to the reduced delivery profile, and the catheter 302 may be retracted from the right renal artery RRA, for example, to a position in the guide catheter GC within the patient's abdominal aorta. Likewise, the guide catheter GC may be retracted to a position within the patient's aorta. The retracted guide catheter may be repositioned, e.g., rotated, such that its distal outlet is generally aligned with the left renal artery LRA. The guidewire G then may be re-advanced through the catheter 302 and the guide catheter GC to a position within the left renal artery LRA, as shown in FIG. 6E (as will be apparent, the order of advancement of the guidewire and the guide catheter optionally may be reversed when accessing either renal artery).

Figure 6F:
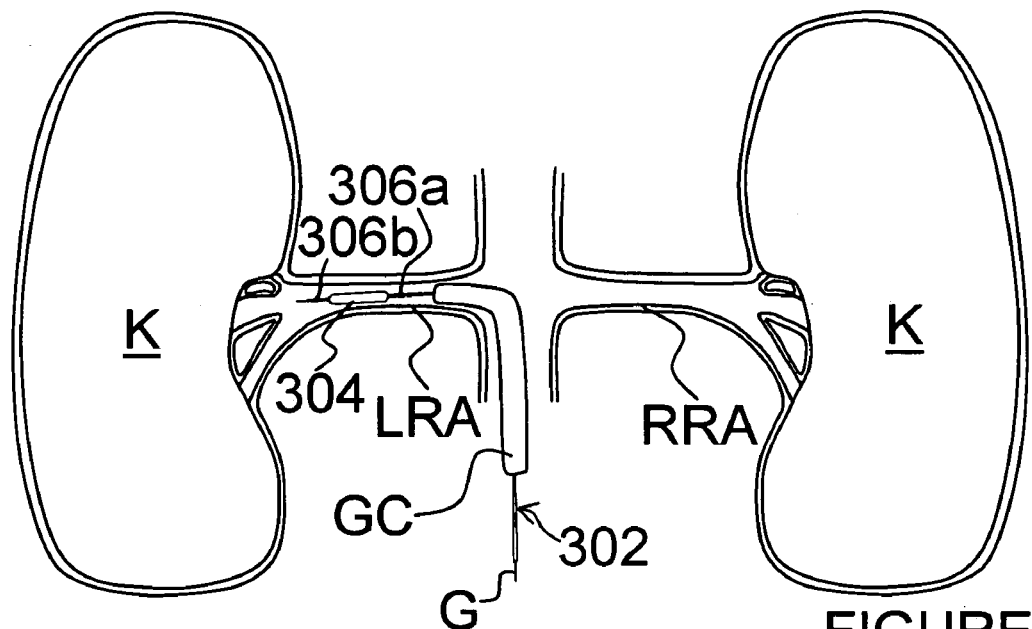
Figure 6G:
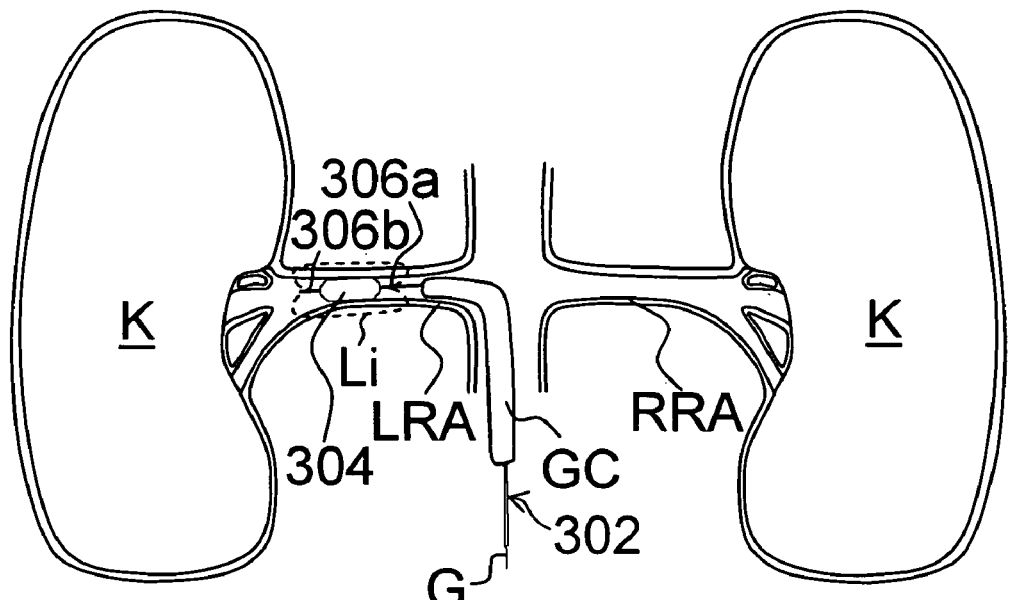
Figure 6H:
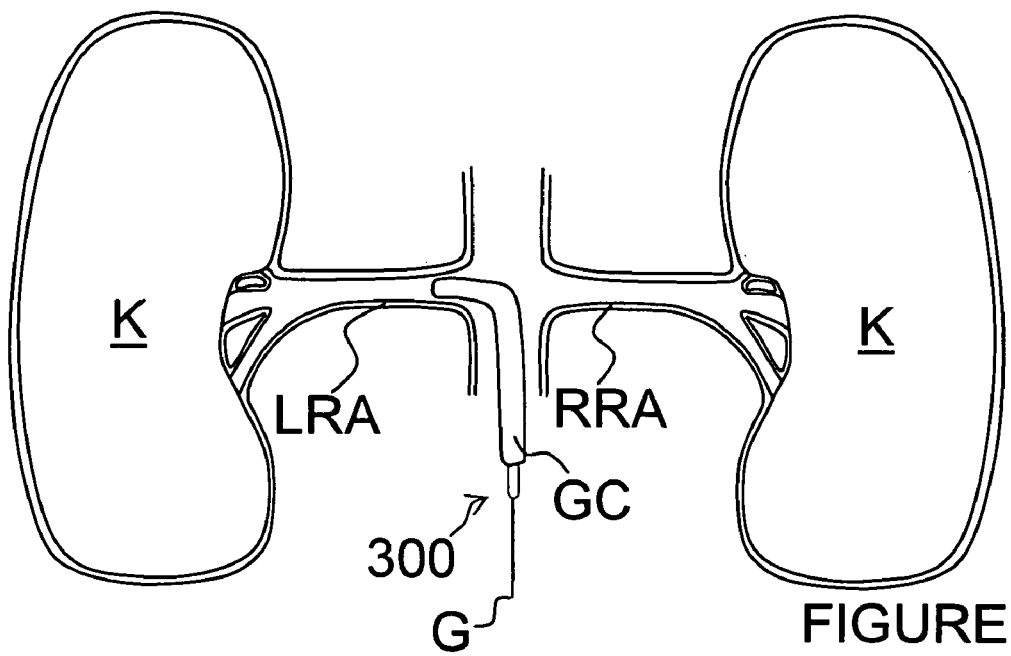

Next, the catheter 302 may be re-advanced over the guidewire and through the guide catheter into position within the left renal artery, as shown in FIG. 6F. In FIG. 6G, once the catheter is properly positioned for PEF therapy, the element 304 optionally may be expanded into contact with the vessel wall, and the guidewire G may be retracted to a position proximal of the treatment site. PEF therapy then may be delivered in a bipolar fashion across the electrodes 306, for example, along propagation lines Li, to achieve renal neuromodulation in neural fibers that contribute to left renal function, e.g., to at least partially achieve renal denervation of the left kidney. As seen in FIG. 6H, after completion of the bilateral PEF therapy, the element 304 may be collapsed back to the reduced delivery profile, and the catheter 302, as well as the guidewire G and the guide catheter GC, may be removed from the patient to complete the bilateral renal neuromodulation procedure.

Figure 7A:
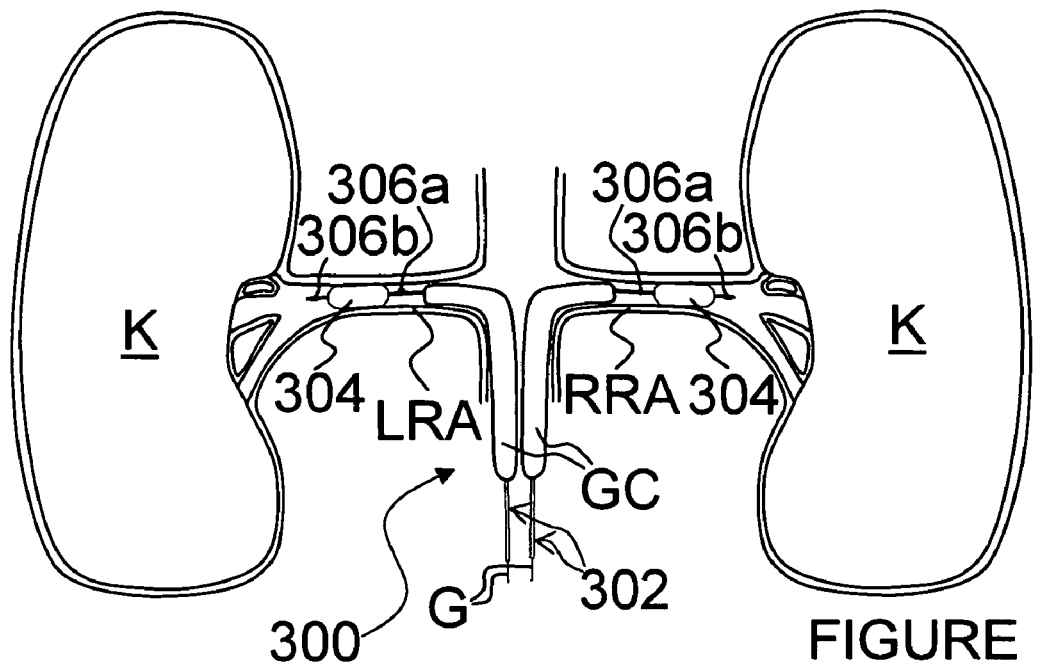
FIGS. 7A and 7B are schematic side views, partially in section, illustrating methods of achieving concurrent bilateral renal neuromodulation utilizing embodiments of the apparatus of FIG. 5A.
Figure 7B:
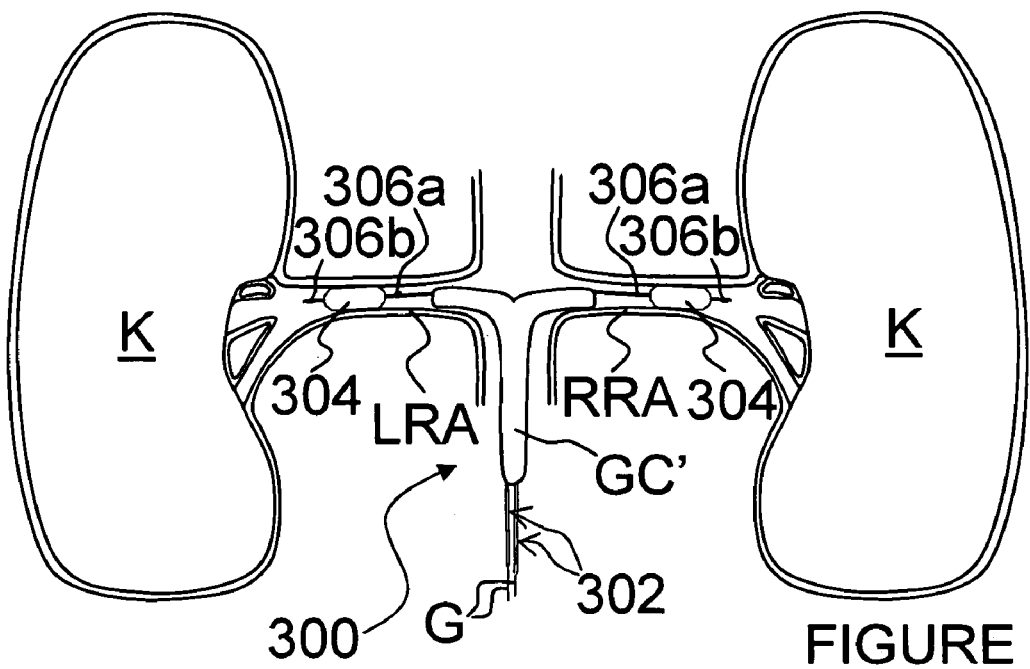

As discussed previously, bilateral renal neuromodulation optionally may be performed concurrently on fibers that contribute to both right and left renal function. FIGS. 7A and 7B illustrate embodiments of apparatus 300 for performing concurrent bilateral renal neuromodulation. In the embodiment of FIG. 7A, apparatus 300 comprises dual PEF therapy catheters 302, as well as dual guidewires G and guide catheters GC. One catheter 302 is positioned within the right renal artery RRA, and the other catheter 302 is positioned within the left renal artery LRA. With catheters 302 positioned in both the right and left renal arteries, PEF therapy may be delivered concurrently by the catheters 302 to achieve concurrent bilateral renal neuromodulation, illustratively via an intravascular approach.

In one example, separate arteriotomy sites may be made in the patient's right and left-femoral arteries for percutaneous delivery of the two catheters 302. Alternatively, both catheters 302 may be delivered through a single femoral access site, either through dual guide catheters or through a single guide catheter. FIG. 7B illustrates an example of apparatus 300 for concurrent bilateral renal neuromodulation utilizing a single arteriotomy access site. In the example of FIG. 7B, both catheters 302 are delivered through a custom bifurcated guide catheter GC' having a bifurcated distal region for concurrently delivering the catheters 302 to the right and left renal arteries. Concurrent (or sequential) bilateral PEF therapy then may proceed.

Figure 8:
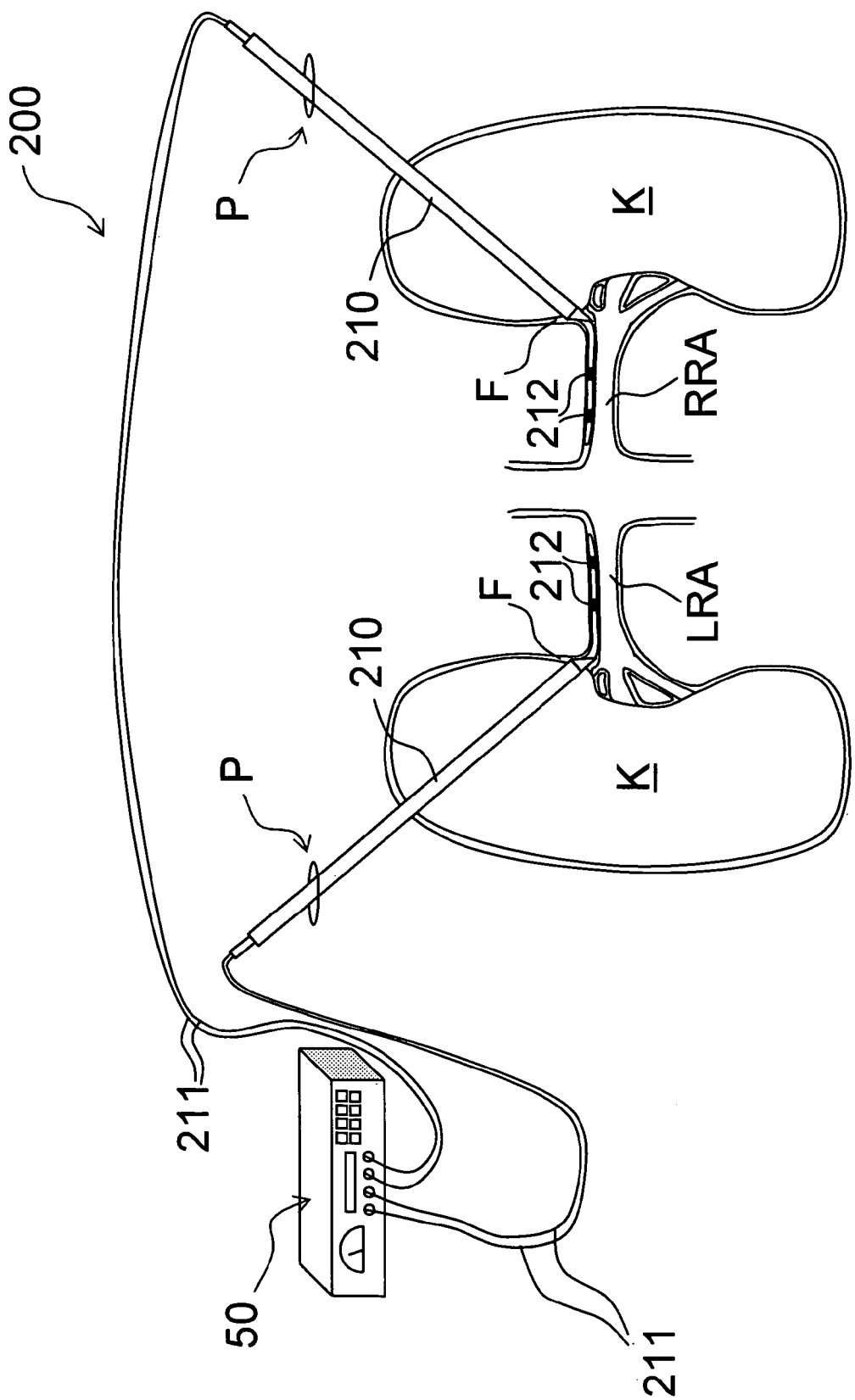
FIG. 8 is a schematic side view, partially in section, illustrating methods of achieving concurrent bilateral renal neuromodulation utilizing an alternative embodiment of the apparatus of FIG. 4.

FIG. 8 illustrates additional methods and apparatus for concurrent bilateral renal neuromodulation. In FIG. 8, an embodiment of extravascular apparatus 200 comprising dual probes 210 and electrodes 212. The electrodes have been positioned in the vicinity of both the left renal artery LRA and the right renal artery RRA. PEF therapy may be delivered concurrently by the electrodes 212 to achieve concurrent bilateral renal neuromodulation, illustratively via an extravascular approach.

As will be apparent, intra-to-extravascular apparatus alternatively may be utilized for bilateral renal neuromodulation. Such bilateral renal neuromodulation may be performed sequentially, concurrently or a combination thereof. For example, ITEV PEF system 320 of FIG. 5B may be utilized for bilateral renal neuromodulation.

Additional methods and apparatus for achieving renal neuromodulation, e.g., via localized drug delivery (such as by a drug pump or infusion catheter) or via use of a stimulation electric field, etc, also may utilized. Examples of such methods and apparatus have been described previously, for example, in co-owned and co-pending U.S. patent application Ser. No. 10/408,665, filed Apr. 8, 2003, and in U.S. Pat. No. 6,978,174, both of which have been incorporated herein by reference in their entireties.

Figure 9:
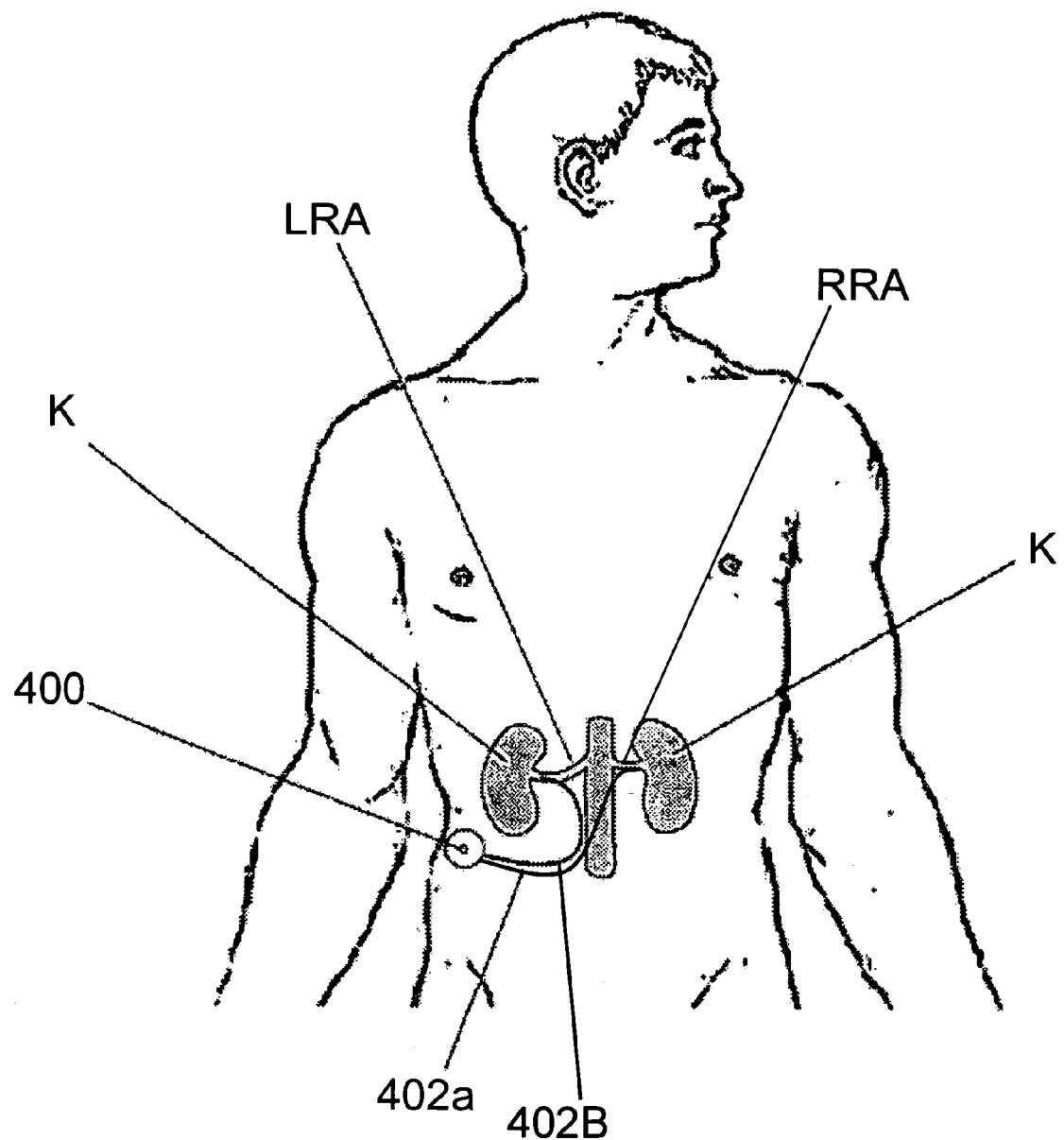
FIG. 9 is a schematic view illustrating an example of methods and apparatus for achieving bilateral renal neuromodulation via localized drug delivery.

FIG. 9 shows one example of methods and apparatus for achieving bilateral renal neuromodulation via localized drug delivery. In FIG. 9, drug reservoir 400, illustratively an implantable drug pump, has been implanted within the patient. Drug delivery catheters 402a and 402b are connected to the drug reservoir and extend to the vicinity of the right renal artery RRA and the left-renal artery LRA, respectively, for delivery of one or more neuromodulatory agents or drugs capable of modulating neural fibers that contribute renal function. Delivering the agent(s) through catheters 402a and 402b may achieve bilateral renal neuromodulation. Such drug delivery through catheters 402a and 402b may be conducted concurrently or sequentially, as well as continuously or intermittently, as desired, in order to provide concurrent or sequential, continuous or intermittent, renal neuromodulation, respectively.

In an alternative embodiment of the apparatus of FIG. 9, catheters 402a and 402b may only temporarily be positioned at a desired location, e.g., for acute delivery of the neuromodulatory agent(s) from an external drug reservoir, such as a syringe. Such temporary positioning may comprise, for example, intravascular, extravascular and/or intra-to-extravascular placement of the catheters. In another alternative embodiment, the drug reservoir 400 may be replaced with an implantable neurostimulator or a pacemaker-type device, and catheters 402 may be replaced with electrical leads coupled to the neurostimulator for delivery of an electric field, such as a pulsed electric field or a stimulation electric field, to the target neural fibers. In yet another alternative embodiment, electrical techniques may be combined with delivery of neuromodulatory agent(s) to achieve desired bilateral renal neuromodulation.

Although preferred illustrative variations of the present invention are described above, it will be apparent to those skilled in the art that various changes and modifications may be made thereto without departing from the invention. For example, although the variations primarily have been described for use in combination with pulsed electric fields, it should be understood that any other electric field may be delivered as desired, including stimulation or nerve block electric fields, and any other alternative neuromodulatory techniques, such as localized delivery of a neuromodulatory agent or drug, may be utilized. It is intended in the appended claims to cover all such changes and modifications that fall within the true spirit and scope of the invention.

We claim:

1. A method for treating a human patient with a diagnosed condition or disease associated with cardio-renal function, the method comprising:
    positioning a nerve modulation device in a vicinity of post-ganglionic neural fibers that innervate a kidney of the patient; and
    reducing neural communication to and from the kidney by at least partially ablating the neural fibers of the patient via the nerve modulation device,
    wherein the kidney continues to secrete renin in the patient after reducing neural communication with the nerve modulation device,
    wherein reducing neural communication to and from the kidney results in improved cardio-renal function of the patient.

2. The method of claim 1 wherein positioning a nerve modulation device in a vicinity of post-ganglionic neural fibers comprises positioning the nerve modulation device within a renal vasculature the patient.

3. The method of claim 2 wherein positioning the nerve modulation device within a renal vasculature comprises positioning the nerve modulation device within a renal artery of the patient.

4. The method of claim 1 wherein positioning the nerve modulation device in a vicinity of post-ganglionic neural fibers comprises percutaneously advancing the nerve modulation device within a renal blood vessel of the patient proximate to the renal nerve.

5. The method of claim 1 wherein positioning a nerve modulation device comprises positioning a thermal transfer device in a vicinity of the post-ganglionic neural fibers of the patient.

6. The method of claim 5 wherein reducing neural communication to and from the kidney by at least partially ablating a renal nerve comprises cooling afferent and efferent nerves of the patient via the thermal transfer device.

7. The method of claim 6 wherein cooling afferent and efferent nerves of the patient comprises delivering a chilled fluid to a target region at least proximate to the afferent and efferent nerves.

8. The method of claim 6 wherein positioning a thermal transfer device in a vicinity of the post-ganglionic neural fibers of the patient comprises positioning a Peltier device in a vicinity of the post-ganglionic neural fibers.

9. The method of claim 5 wherein reducing neural communication to and from the kidney by at least partially ablating a renal nerve comprises heating afferent and efferent nerves of the patient via the thermal transfer device.

10. The method of claim 9 wherein heating afferent and efferent nerves comprises heating the nerves with RF energy.

11. The method of claim 1 wherein reducing neural communication to and from the kidney by at least partially ablating a renal nerve comprises delivering an electric field via the nerve modulation device to afferent and efferent nerves of the patient.

12. The method of claim 1 wherein reducing neural communication to and from the kidney by at least partially ablating a renal nerve comprises delivering a chemical agent to afferent and efferent nerves proximate the nerve modulation device.

13. The method of claim 12 wherein delivering a chemical agent comprises delivering alcohol.

14. The method of claim 12 wherein delivering a chemical agent comprises delivering phenol.

15. The method of claim 1 wherein reducing neural communication to and from the kidney by at least partially ablating a renal nerve comprises irreversibly ablating afferent and efferent nerves of the patient.

16. The method of claim 1, further comprising removing the nerve modulation device from the patient after at least partially ablating the renal nerve.

17. A method for treating a human patient with a diagnosed condition or disease associated with cardio-renal function, the method comprising:
   positioning an energy element in a renal vasculature of the patient and in a vicinity of post-ganglionic neural fibers that innervate a kidney of the patient; and
   at least partially ablating a renal nerve of the patient via the energy element,
   wherein at least partially ablating the renal nerve results in a therapeutically beneficial reduction in blood pressure of the patient.

18. The method of claim 17 wherein positioning an energy element in a renal vasculature of the patient comprises positioning a thermal transfer device in the renal vasculature of the patient and in a vicinity of the neural fibers.

19. The method of claim 18 wherein at least partially ablating a renal plexus of the patient comprises cooling afferent and efferent nerves of the patient via the thermal transfer device.

20. A method for therapeutic renal denervation of a human patient having a diagnosed condition or disease associated with central sympathetic overactivity, the method comprising:
   positioning a thermal element in a renal vasculature of the patient and in a vicinity of post-ganglionic neural fibers that innervate a kidney of the patient; and
   at least partially ablating the neural fibers of the patient via the thermal element,
   wherein at least partially ablating the neural fibers results in a therapeutically beneficial reduction in central sympathetic overactivity of the patient.

21. The method of claim 20 wherein positioning a thermal element in a renal vasculature of the patient comprises positioning a renal denervation catheter having an energy element in the renal vasculature of the patient.

22. The method of claim 21 wherein positioning a renal denervation catheter having an energy element in the renal vasculature of the patient comprises positioning a renal denervation catheter having an electrode in the renal vasculature of the patient.

23. The method of claim 20 wherein at least partially ablating the neural fibers of the patient via the thermal element comprises at least partially ablating the neural fibers via cold.

24. The method of claim 20 wherein the therapeutically beneficial reduction in central sympathetic overactivity comprises a reduction in clinical symptoms of hypertension in the patient.

25. The method of claim 20 wherein the therapeutically beneficial reduction in central sympathetic overactivity comprises a reduction in clinical symptoms of heart failure in the patient.

26. The method of claim 20 wherein the therapeutically beneficial reduction in central sympathetic overactivity comprises a reduction in clinical symptoms of chronic renal failure in the patient.

27. The method of claim 20 wherein the therapeutically beneficial reduction in central sympathetic overactivity comprises a reduction in clinical symptoms of impaired renal function in the patient.

28. The method of claim 20 wherein the therapeutically beneficial reduction in central sympathetic overactivity comprises a reduction in clinical symptoms of acute myocardial infarction in the patient.

* * * * *

US 8,145,317 C1

(12) INTER PARTES REEXAMINATION CERTIFICATE (1277th)
United States Patent
Demarais et al.

(10) Number: US 8,145,317 C1
(45) Certificate Issued: *Jun. 2, 2016

(54) METHODS FOR RENAL NEUROMODULATION

(75) Inventors: Denise Demarais, Los Gatos, CA (US); Hanson Gifford, III, Woodside, CA (US); Mark Deem, Mountain View, CA (US); Douglas Sutton, Pacifica, CA (US); Howard R. Levin, Teaneck, NJ (US); Mark Gelfand, New York, NY (US)

(73) Assignee: ARDIAN, INC., Menlo Park, CA (US)

Reexamination Request:
No. 95/002,327, Sep. 14, 2012

Reexamination Certificate for:
Patent No.: 8,145,317
Issued: Mar. 27, 2012
Appl. No.: 11/368,577
Filed: Mar. 6, 2006

( * ) Notice: This patent is subject to a terminal disclaimer.

Related U.S. Application Data

(63) Continuation-in-part of application No. 11/133,925, filed on May 20, 2005, now Pat. No. 8,771,252, which is a continuation of application No. 10/900,199, filed on Jul. 28, 2004, now Pat. No. 6,978,174, which is a continuation-in-part of application No. 10/408,665, filed on Apr. 8, 2003, now Pat. No. 7,162,303, application No. 11/368,577, which is a continuation-in-part of application No. 10/408,665, filed on Apr. 8, 2003, now Pat. No. 7,162,303, said application No. 11/368,577 is a continuation-in-part of application No. 11/189,563, filed on Jul. 25, 2005, now Pat. No. 8,145,316, which is a continuation-in-part of application No. 11/129,765, filed on May 13, 2005, now Pat. No. 7,653,438, application No. 11/368,577, which is a continuation-in-part of application No. 11/266,993, filed on Nov. 4, 2005, now Pat. No.

(Continued)

(51) Int. Cl.
*A61N 1/00* (2006.01)
*A61F 7/00* (2006.01)
(Continued)

(52) U.S. Cl.
CPC .............. *A61N 1/05* (2013.01); *A61M 5/14276* (2013.01); *A61N 1/326* (2013.01); *A61N 1/327* (2013.01); *A61N 1/36017* (2013.01); *A61N 1/40* (2013.01); *A61M 5/1723* (2013.01); *A61M 2210/1082* (2013.01); *A61N 1/0551* (2013.01); *A61N 1/3627* (2013.01); *A61N 1/36117* (2013.01)

(58) Field of Classification Search
None
See application file for complete search history.

(56) References Cited

To view the complete listing of prior art documents cited during the proceeding for Reexamination Control Number 95/002,327, please refer to the USPTO's public Patent Application Information Retrieval (PAIR) system under the Display References tab.

*Primary Examiner* — Cary Wehner

(57) ABSTRACT

Methods and apparatus are provided for treating hypertension, e.g., via a pulsed electric field, via a stimulation electric field, via localized drug delivery, via high frequency ultrasound, via thermal techniques, etc. Such neuromodulation may effectuate irreversible electroporation or electrofusion, necrosis and/or inducement of apoptosis, alteration of gene expression, action potential attenuation or blockade, changes in cytokine up-regulation and other conditions in target neural fibers. In some embodiments, neuromodulation is applied to neural fibers that contribute to renal function. In some embodiments, such neuromodulation is performed in a bilateral fashion. Bilateral renal neuromodulation may provide enhanced therapeutic effect in some patients as compared to renal neuromodulation performed unilaterally, i.e., as compared to renal neuromodulation performed on neural tissue innervating a single kidney.

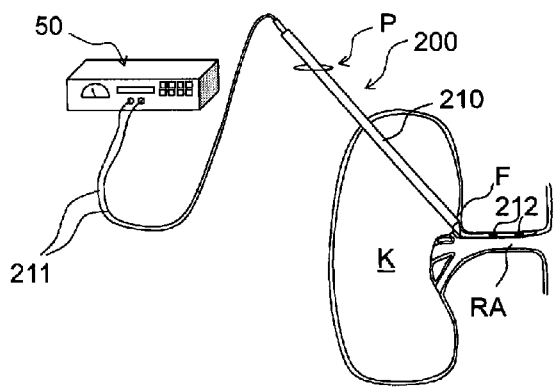

Related U.S. Application Data 7,756,583, and a continuation-in-part of application No. 11/363,867, filed on Feb. 27, 2006, now Pat. No. 7,620,451, and a continuation-in-part of application No. 11/189,563, filed on Jul. 25, 2005, now Pat. No. 8,145,316.

(60) Provisional application No. 60/442,970, filed on Jan. 29, 2003, provisional application No. 60/415,575, filed on Oct. 3, 2002, provisional application No. 60/370,190, filed on Apr. 8, 2002, provisional application No. 60/616,254, filed on Oct. 5, 2004, provisional application No. 60/624,793, filed on Nov. 2, 2004, provisional application No. 60/813,589, filed on Dec. 29, 2005.

(51) Int. Cl.
| | | |
|---|---|---|
| (51) *A61N 1/05* | (2006.01) |
| *A61N 1/32* | (2006.01) |
| *A61N 1/40* | (2006.01) |
| *A61M 5/142* | (2006.01) |
| *A61M 5/172* | (2006.01) |
| *A61N 1/36* | (2006.01) |
| *A61N 1/362* | (2006.01) |

INTER PARTES REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-3, 5, 9, 10, 17, 20 and 24 are cancelled.

Claims 4, 6-8, 11-16, 18, 19, 21-23, and 25-28 were not reexamined.

\* \* \* \* \*